(12) United States Patent
Huang et al.

(10) Patent No.: US 11,498,909 B2
(45) Date of Patent: Nov. 15, 2022

(54) COMPOUND ACTING AS ANTIBIOTICS

(71) Applicant: KBP BIOSCIENCES CO., LTD., Jinan (CN)

(72) Inventors: Zhenhua Huang, Shandong (CN); Li Li, Shandong (CN); Min Zhang, Shandong (CN)

(73) Assignee: KBP BIOSCIENCES CO., LTD., Jinan (CN)

( * ) Notice: Subject to any disclaimer, the term of this patent is extended or adjusted under 35 U.S.C. 154(b) by 0 days.

(21) Appl. No.: 16/968,390

(22) PCT Filed: Feb. 11, 2019

(86) PCT No.: PCT/CN2019/074771
§ 371 (c)(1),
(2) Date: Aug. 7, 2020

(87) PCT Pub. No.: WO2019/154412
PCT Pub. Date: Aug. 15, 2019

(65) Prior Publication Data
US 2020/0392096 A1    Dec. 17, 2020

(30) Foreign Application Priority Data

Feb. 10, 2018 (CN) .......... 201810138645.X
Apr. 11, 2018 (CN) .......... 201810320980.1

(51) Int. Cl.
| | | |
|---|---|---|
| *C07D 307/16* | (2006.01) | |
| *C07D 231/12* | (2006.01) | |
| *C07D 333/24* | (2006.01) | |
| *C07D 401/04* | (2006.01) | |

(52) U.S. Cl.
CPC ......... *C07D 307/16* (2013.01); *C07D 231/12* (2013.01); *C07D 333/24* (2013.01); *C07D 401/04* (2013.01)

(58) Field of Classification Search
CPC .. C07D 307/16; C07D 231/12; C07D 333/24; C07D 401/04
See application file for complete search history.

(56) References Cited

U.S. PATENT DOCUMENTS 9,073,821 B2 * 7/2015 Takashima .......... C07D 209/52
2012/0258948 A1   10/2012 Brown et al.

FOREIGN PATENT DOCUMENTS

| CN | 101765585 A | 6/2010 |
|---|---|---|
| CN | 102267924 A | 12/2011 |
| CN | 103003233 A | 3/2013 |
| CN | 105777464 A | 7/2016 |
| WO | 2004/062601 A2 | 7/2004 |
| WO | 2008/154642 A2 | 12/2008 |
| WO | 2011/132712 A1 | 10/2011 |
| WO | 2012/031298 A2 | 3/2012 |

OTHER PUBLICATIONS

Huff, Joel R., "HIV Protease: A Novel Chemotherapeutic Target for AIDS," Journal of Medicinal Chemistry, vol. 34, No. 8, Aug. 1991, pp. 2305-2314.*
International Search Report and Written Opinion for Application No. PCT/CN2019/074771, dated May 6, 2019, 19 pages.

* cited by examiner

*Primary Examiner* — Rebecca L Anderson
(74) *Attorney, Agent, or Firm* — McCarter & English, LLP; Wei Song; Paul M. Zagar

(57) ABSTRACT

The present invention provides a novel antibiotic compound represented by the following formula (I), a pharmaceutically acceptable salt thereof, an ester thereof, a prodrug thereof, a solvate thereof, or a deuterated analog thereof, or a stereoisomer thereof. The compound of the present invention exhibits excellent antibacterial activity, especially against Gram bacteria.

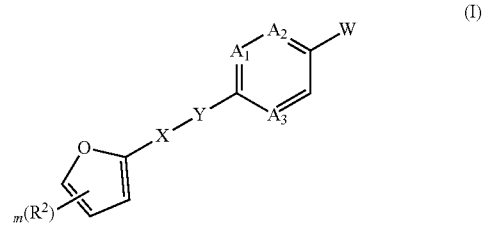

wherein each group is defined as in the description.

13 Claims, No Drawings

COMPOUND ACTING AS ANTIBIOTICS

CROSS-REFERENCE TO RELATED APPLICATIONS

This application is a U.S. national stage filing, under 35 U.S.C. § 371(c), of International Application No. PCT/CN2019/074771, filed on Feb. 11, 2019, which claims priority to Chinese Patent Application No. 201810320980.1, filed on Apr. 11, 2018; and Chinese Patent Application No. 201810138645.X, filed on Feb. 10, 2018.

TECHNICAL FIELD

The present invention belongs to the technical field of medicine, and relates to compounds as antibiotics, a pharmaceutically acceptable salt thereof, an ester thereof, a prodrug thereof, a solvate thereof, or a deuterated analog thereof, or a stereoisomer thereof, a process for preparing these compounds, and a pharmaceutical composition comprising these compounds; the present invention also relates to the use of the compound for the treatment and/or prevention of infectious diseases, especially for the treatment and/or prevention of infectious diseases caused by Gram-negative bacteria.

BACKGROUND

In recent years, due to the widespread use of high-efficiency and broad-spectrum antibacterial drugs, the bacteria selectivity caused great pressure, so that the drug resistance of common Gram-negative bacilli and the number of the drug-resistant strains increased continuously, and the Enterobacteriaceae bacteria of the extended-spectrum β-lactamase (ESBLs), and the multi-drug resistant *Pseudomonas aeruginosa* and *acinetobacter* that are resistant to all β-lactams and quinolones antibacterial drugs even appeared clinically.

Lipid A is the membrane binding region of the outer membrane lipopolysaccharide (LPS) of Gram-negative bacteria (such as *Pseudomonas aeruginosa* and *Acinetobacter baumannii*), which is an important part for protecting bacteria from external factors (such as antibiotics). In addition, it is also a powerful endotoxin, which can cross the intestinal mucosal barrier and enter the blood, causing fatal septic shock, and therefore is an important inducement of gram-negative bacteria infection. Therefore, it is generally believed that by inhibiting lipid A biosynthesis, diseases caused by the Gram-negative bacteria can be controlled. UDP-3-O—(R-hydroxytetradecanoyl)-N-acetylglucosamine deacetylase (LpxC) is a zinc metalloenzyme that catalyzes the second step of lipid A biosynthesis in the Gram-negative bacteria, and it is a necessary enzyme for the survival of the Gram-negative bacteria. Therefore, by inhibiting the LpxC, the growth of the bacteria can be inhibited, thereby exerting an effect on diseases caused by the gram-negative bacteria.

Patent WO2004062601A2 and the like disclose a series of LpxC inhibitors such as CHIR-090, and WO2008154642A2 also discloses some LpxC inhibitors such as ACHN-975. Patent WO2011132712A1 and the like also disclose a series of LpxC inhibitor, wherein some of the LpxC inhibitors have the following structures:

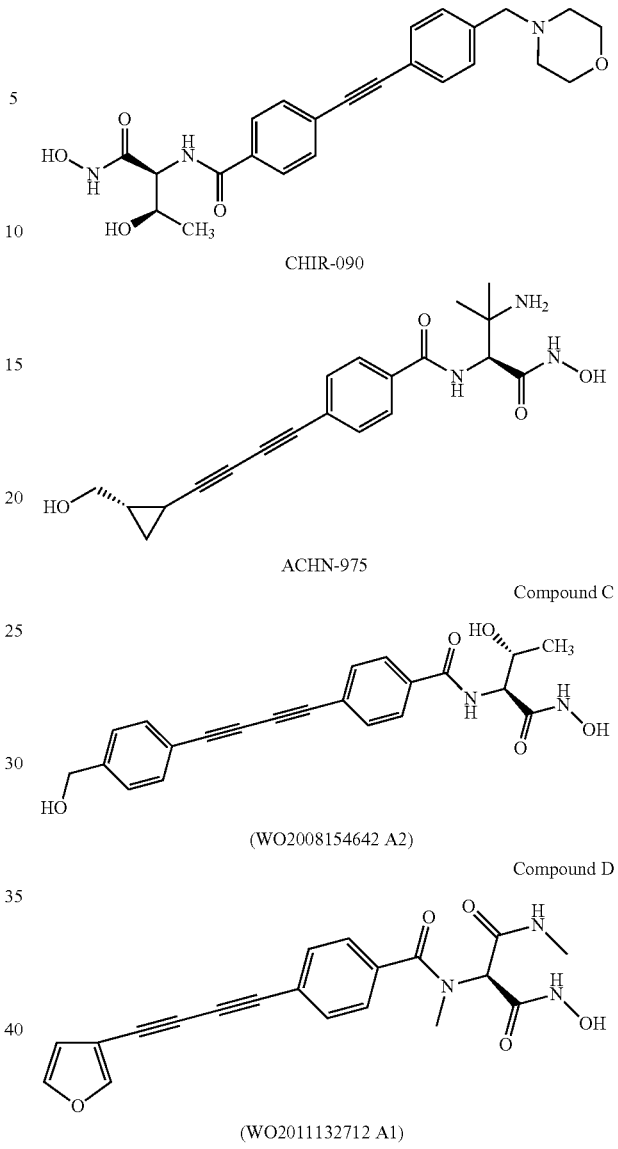

These compounds in the prior art show certain antibacterial activity against bacteria, especially Gram-negative bacteria, but there is still room for improvement in their antibacterial activity.

SUMMARY OF THE INVENTION

After in-depth and diligent research, the present inventors have found a novel antibacterial compound, a pharmaceutically acceptable salt thereof, an ester thereof, a prodrug thereof, a solvate thereof, or a deuterated analog thereof, or a stereoisomer thereof (hereinafter, also known as the compound of the present invention), which is a compound that is an inhibitor of UDP-3-O—(R-hydroxytetradecanoyl)-N-acetylglucosamine deacetylase (LpxC). The compound of the present invention can achieve the excellent antibacterial activity, especially showing excellent antibacterial activity against Gram bacteria.

Specifically, the present invention provides a compound represented by the general formula (I), a pharmaceutically acceptable salt thereof, an ester thereof, a prodrug thereof, a solvate thereof, or a deuterated analog thereof, or a stereoisomer thereof:

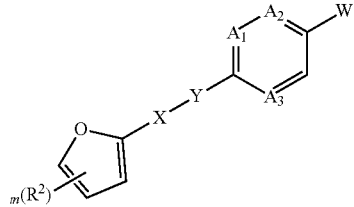

wherein,
W represents

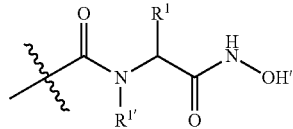

$R^1$ is selected from a group consisting of —$(CH_2)_{0-4}C(R^{1a},R^{1b})(CH_2)_{0-4}OR^3$, —$(CH_2)_{0-4}C(O)NR^4R^5$, —$(CH_2)_{0-4}C(R^{1a},R^{1b})NR^4R^5$, —$(CH_2)_{0-4}C(R^{1a},R^{1b})(CH_2)_{0-4}S(O)_{0-2}R^6$ and —$(CH_2)_{0-4}C(R^{1a},R^{1b})(CH_2)_{0-4}SC(O)R^7$, wherein, $R^{1a}$, $R^{1b}$, $R^3$, $R^4$, $R^5$, $R^6$ and $R^7$ are each independently selected from a group consisting of H, $C_{1-6}$alkyl and OH;

$R^{1'}$ is selected from a group consisting of hydrogen and $C_{1-6}$alkyl;

$A_1$, $A_2$ and $A_3$ are each independently selected from a group consisting of CH and a heteroatom;

X and Y are each independently selected from a group consisting of a benzene ring group, a 3-8 membered unsaturated heterocyclic group, an alkenyl group, an alkynyl group and

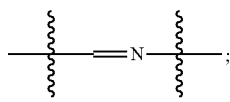 [SMILES: *C=N*]

$R^2$ is

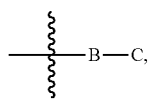

B is absent or represents —($C_{1-8}$alkyl)-, wherein 0-2 carbon atoms in said —($C_{1-8}$alkyl)- are optionally replaced with O or $NR^8$, C is selected from a group consisting of $C_{1-6}$alkyl, —$OR^9$, —$NR^9R^{9'}$, phenyl and 3-8 membered saturated and/or unsaturated heterocyclyl, $R^8$, $R^9$ and $R^{9'}$ are each independently selected from hydrogen atom, $C_{1-6}$alkyl and $C_{3-6}$cycloalkyl;

m is 0, 1, 2 or 3.

In another embodiment of the present invention, there is provided a compound represented by the general formula (I), a pharmaceutically acceptable salt thereof, an ester thereof, a prodrug thereof, a solvate thereof, or a deuterated analog thereof, or a stereoisomer thereof, wherein, W represents

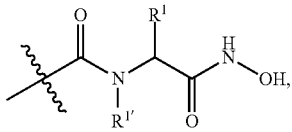

$R^1$ is selected from a group consisting of —$(CH_2)_{0-4}C(R^{1a},R^{1b})(CH_2)_{0-4}OR^3$, —$(CH_2)_{0-4}C(O)NR^4R^5$ and —$(CH_2)_{0-4}C(R^{1a},R^{1b})NR^4R^5$, wherein, $R^{1a}$, $R^{1b}$, $R^3$, $R^4$ and $R^5$ are each independently selected from a group consisting of H, $C_{1-4}$alkyl and OH;

$R^{1'}$ is selected from a group consisting of hydrogen and $C_{1-6}$alkyl;

$A_1$, $A_2$ and $A_3$ are each independently selected from a group consisting of CH and a heteroatom;

X and Y are each independently selected from a group consisting of a benzene ring group, 5-8 membered unsaturated heterocyclic group, an alkenyl group, an alkynyl group and

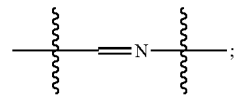

$R^2$ is

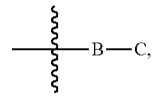

B is absent or represents —($C_{1-8}$alkyl)-, wherein β-2 carbon atoms in said —($C_{1-8}$alkyl)- are optionally replaced with 0 or $NR^8$, C is selected from a group consisting of $C_{1-6}$alkyl, —$OR^9$, —$NR^9R^{9'}$, phenyl and 3-8 membered saturated and/or unsaturated heterocyclyl, $R^8$, $R^9$ and $R^{9'}$ are each independently selected from hydrogen atom, $C_{1-6}$alkyl and $C_{3-6}$cycloalkyl;

m is 0, 1 or 2.

In another embodiment of the present invention, there is provided a compound represented by the general formula (I), a pharmaceutically acceptable salt thereof, an ester thereof, a prodrug thereof, a solvate thereof, or a deuterated analog thereof, or a stereoisomer thereof, wherein, W represents

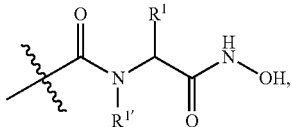

$R^1$ is selected from a group consisting of —$C(R^{1a},R^{1b})OR^3$ and —$C(O)NR^4R^5$, wherein, $R^{1a}$, $R^{1b}$, $R^3$, $R^4$ and $R^5$ are each independently selected from a group consisting of hydrogen atom, methyl and hydroxyl;

R$^{1'}$ is selected from a group consisting of hydrogen and C$_{1-4}$alkyl;

A$_1$, A$_2$, and A$_3$ are each independently selected from a group consisting of CH and N; X and Y are each independently selected from a group consisting of a benzene ring group, 5-6 membered unsaturated heterocyclic group, an alkenyl group, an alkynyl group and

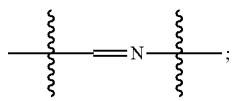 [SMILES: *C=N*]

R$^2$ is

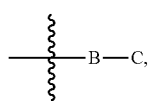

B is absent or represents —(C$_{1-4}$alkyl)-,

C is selected from a group consisting of —OR$^9$ and —NR$^9$R$^{9'}$,

R$^9$ and R$^{9'}$ are each independently selected from hydrogen atom, methyl, ethyl and isopropyl;

m is 0, 1 or 2.

In another embodiment of the present invention, there is provided a compound represented by the general formula (I), a pharmaceutically acceptable salt thereof, an ester thereof, a prodrug thereof, a solvate thereof, or a deuterated analog thereof, or a stereoisomer thereof, wherein, W represents

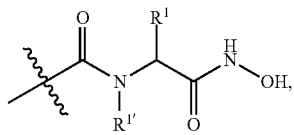

R$^1$ is selected from a group consisting of —C(R$^{1a}$,R$^{1b}$)OR$^3$ and —C(O)NR$^4$R$^5$, wherein, R$^{1a}$, R$^{1b}$, R$^3$, R$^4$ and R$^5$ are each independently selected from a group consisting of hydrogen atom, methyl and hydroxyl;

R$^{1'}$ is selected from a group consisting of hydrogen and C$_{1-4}$alkyl;

A$_1$, A$_2$, and A$_3$ are each independently selected from a group consisting of CH and N;

X and Y are each independently selected from a group consisting of a benzene ring group, pyrrole ring group, imidazole ring group, pyrazole ring group, 1,2,3-triazole ring group, 1,2,4-triazole ring group, tetrazole ring group, thiophene ring group, thiazole ring group, isothiazole ring group, 1,2,4-thiadiazole ring group, furan ring group, oxazole ring group, isoxazole ring group, 1,2,4-oxadiazole ring group, pyridine ring group, an alkenyl group, an alkynyl group,

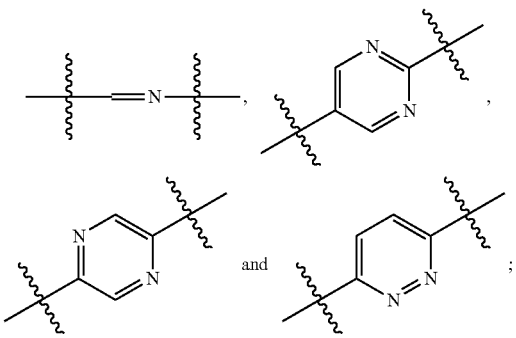

R$^2$ is (CH$_2$)$_{1-4}$OH;

m is 0, 1 or 2.

In another embodiment of the present invention, there is provided a compound represented by the general formula (I), a pharmaceutically acceptable salt thereof, an ester thereof, a prodrug thereof, a solvate thereof, or a deuterated analog thereof, or a stereoisomer thereof, wherein, W represents

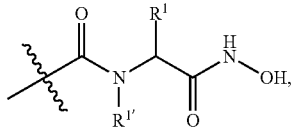

R$^1$ is selected from a group consisting of —C(H,CH$_3$)OH and —C(O)NHCH$_3$;

R$^{1'}$ is selected from a group consisting of hydrogen, methyl and ethyl;

A$_1$, A$_2$, and A$_3$ are each independently selected from a group consisting of CH and N;

X and Y are each independently selected from a group consisting of a benzene ring group, pyrrole ring group, imidazole ring group, pyrazole ring group, 1,2,3-triazole ring group, 1,2,4-triazole ring group, tetrazole ring group, furan ring group, oxazole ring group, isoxazole ring group, 1,2,4-oxadiazole ring group, pyridine ring group, an alkenyl group, an alkynyl group,

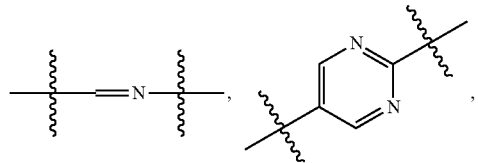

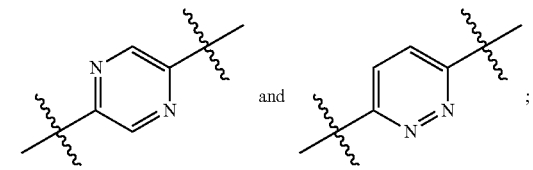

R$^2$ is -CH$_2$OH;

m is 0 or 1.

In another embodiment of the present invention, there is provided a compound represented by general formula (II), a pharmaceutically acceptable salt thereof, an ester thereof, a prodrug thereof, a solvate thereof, or a deuterated analog thereof, or a stereoisomer thereof:

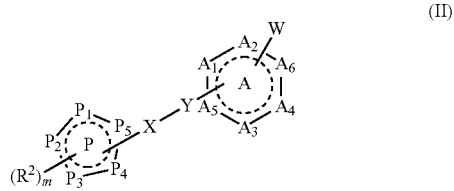
(II)

wherein, W represents —($C_{0-8}$alkyl optionally substituted by a substituent group)-C(O)—N($R^{1'}$)—($C_{1-8}$alkyl optionally substituted by $R^1$)—C(O)—N(H)—OH;

$R^1$ are each independently selected from a group consisting of $C_{1-8}$alkyl optionally substituted by a substituent group, —($C_{0-8}$alkyl optionally substituted by a substituent group)C(O)$NR^4R^5$, —($C_{0-8}$alkyl optionally substituted by a substituent group)S(O)$_{1-2}R^3$ and —($C_{0-8}$alkyl optionally substituted by a substituent group)S(O)$_{1-2}NR^4R^5$, wherein, $R^3$, $R^4$ and $R^5$ are each independently selected from a group consisting of hydrogen atom, halogen atom, $C_{1-8}$alkyl optionally substituted by a substituent group, $C_{2-8}$alkenyl optionally substituted by a substituent group and $C_{2-8}$alkynyl optionally substituted by a substituent group;

$R^{1'}$ is selected from a group consisting of hydrogen atom, hydroxyl, halogen atom, carboxyl, $C_{1-8}$alkyl optionally substituted by a substituent group, $C_{2-8}$alkenyl optionally substituted by a substituent group and $C_{2-8}$alkynyl optionally substituted by a substituent group, or $R^{1'}$ and the carbon atom in the $C_{0-8}$alkyl optionally substituted by a substituent group in the group W, together with the groups N and C(O), form 5-6 membered heterocyclic group;

$A_1$, $A_2$, $A_3$, $A_4$, $A_5$ and $A_6$ are each independently selected from a group consisting of $CR^aR^a$, $NR^c$, O and S;

X and Y are each independently selected from a group consisting of a bond, 5-14 membered heteroaryl group optionally substituted by a substituent group, 6-14 membered aryl group optionally substituted by a substituent group, —(C=C)—, —(C≡C)—, =N—, —C(O)—$NR^c$—, wherein at least one of X and Y is not a bond;

$P_1$, $P_2$, $P_3$, $P_4$ and $P_5$ are each independently selected from a group consisting of $CR^aR^a$, $NR^c$, O and S;

m represents an integer of 0-4;

in each occurrence, $R^2$ each independently represents

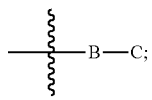

in each occurrence, B independently represents a bond, or is each independently selected from a group consisting of $C_{1-8}$alkyl optionally in which at least one carbon atom is replaced with at least one group of S, O and $NR^c$ and/or optionally substituted by a substituent group, $C_{2-8}$alkenyl optionally in which at least one carbon atom is replaced with at least one group of S, O and $NR^c$ and/or optionally substituted by a substituent group and $C_{2-8}$alkynyl optionally in which at least one carbon atom is replaced with at least one group of S, O and $NR^c$ and/or optionally substituted by a substituent group; in each occurrence, C independently represents hydrogen atom, cyano, mercapto, halogen atom, carboxyl, nitro, $C_{1-8}$alkyl optionally substituted by a substituent group, $C_{1-8}$alkyloxy optionally substituted by a substituent group, —$OR^c$, —$NR^cR^c$, 3-12 membered cycloalkyl optionally substituted by a substituent group, 3-12 membered heterocyclyl optionally substituted by a substituent group, 5-14 membered heteroaryl optionally substituted by a substituent group and 6-14 membered aryl optionally substituted by a substituent group;

$R^a$ either is absent, or in each occurrence are each independently selected from a group consisting of hydrogen atom, cyano, mercapto, halogen atom, carboxyl, nitro, —$OR^c$, —$NR^cR^c$, —N(OH)$R^c$, —C(O)$R^d$, —C(O)$OR^c$, —C(O)$NR^cR^c$, —OC(O)$NR^cR^c$, —$NR^c$C(O)$OR^c$, —$NR^c$C(O)$R^d$, —S(O)$_{1-2}$—$NR^cR^c$, —S(O)$_{1-2}R^d$, —$NR^c$S(O)$_{1-2}R^d$, —S(O)$_{1-2}$—$OR^c$, $C_{1-8}$alkyl optionally substituted by a substituent group, —($C_{1-8}$alkyl optionally substituted by a substituent group)$OR^c$, —($C_{1-8}$alkyl optionally substituted by a substituent group)$NR^cR^c$, $C_{1-8}$alkyloxy optionally substituted by a substituent group, $C_{2-8}$alkenyl optionally substituted by a substituent group, $C_{2-8}$alkynyl optionally substituted by a substituent group, 3-12 membered cycloalkyl optionally substituted by a substituent group, 3-12 membered heterocyclyl optionally substituted by a substituent group, 6-14 membered aryl optionally substituted by a substituent group and 5-14 membered heteroaryl optionally substituted by a substituent group;

$R^c$ either is absent, or in each occurrence are each independently selected from a group consisting of hydrogen atom, halogen atom, carboxyl, —C(O)$R^d$, —C(O)$OR^b$, —C(O)$NR^bR^b$, —S(O)$_{1-2}$—$NR^bR^b$, —S(O)$_{1-2}R^d$, —S(O)$_{1-2}$—$OR^b$, $C_{1-8}$alkyl optionally substituted by a substituent group, —($C_{1-8}$alkyl optionally substituted by a substituent group)$OR^b$, —($C_{1-8}$alkyl optionally substituted by a substituent group)$NR^bR^b$, $C_{2-8}$alkenyl optionally substituted by a substituent group, $C_{2-8}$alkynyl optionally substituted by a substituent group, 3-12 membered cycloalkyl optionally substituted by a substituent group, 3-12 membered heterocyclyl optionally substituted by a substituent group, 6-14 membered aryl optionally substituted by a substituent group and 5-14 membered heteroaryl optionally substituted by a substituent group; or in case that two $R^c$ groups are attached to the same atom, two $R^c$ groups, together with the atom attached thereto, form 3-12 membered heterocycle optionally substituted by a substituent group;

$R^b$, in each occurrence, is each independently selected from a group consisting of hydrogen atom, halogen atom, carboxyl, sulfonic acid group, $C_{1-8}$alkyl optionally substituted by a substituent group, $C_{1-8}$alkylsulfonyl optionally substituted by a substituent group, $C_{1-8}$alkylsulfinyl optionally substituted by a substituent group, 3-12 membered cycloalkyl optionally substituted by a substituent group, 3-12 membered heterocyclyl optionally substituted by a substituent group, 6-14 membered aryl optionally substituted by a substituent group and 5-14 membered heteroaryl optionally substituted by a substituent group; or in case that two $R^b$ groups are attached to the same atom, two $R^b$ groups, together with the atom attached thereto, form 3-12 membered heterocycle optionally substituted by a substituent group;

$R^d$, in each occurrence, is each independently selected from a group consisting of hydrogen atom, hydroxyl, mercapto, halogen atom, carboxyl, nitro, amino, $C_{1-8}$alkylamino optionally substituted by a substituent group, ($C_{1-8}$alkyl optionally substituted by a substituent group)$_2$amino, sulfonic acid group, $C_{1-8}$alkyl optionally substituted by a substituent group, $C_{1-8}$alkyloxy optionally substituted by a substituent group, $C_{1-8}$alkylsulfonyl optionally substituted by a substituent group, $C_{1-8}$alkylsulfinyl optionally substituted by a substituent group, 3-12 membered cycloalkyl optionally substituted by a substituent group, 3-12 membered heterocyclyl optionally substituted by a substituent group, 6-14 membered aryl optionally substituted by a substituent group and 5-14 membered heteroaryl optionally substituted by a substituent group;

the substituent group in said "optionally substituted by a substituent group" is each independently selected from a group consisting of hydroxyl, mercapto, carboxyl, cyano, nitro, amino, halogen atom, sulfonic acid group, $C_{1-8}$alkyl, $C_{1-8}$alkoxy$C_{1-8}$alkyl, hydroxy$C_{1-8}$alkyl, amino$C_{1-8}$alkyl, carboxy$C_{1-8}$alkyl, ester group-$C_{1-8}$alkyl, $C_{1-8}$alkyloxy, hydroxy$C_{1-8}$alkyloxy, amino$C_{1-8}$alkyloxy, carboxy$C_{1-8}$alkyloxy, $C_{1-8}$alkyl$C_{1-8}$alkyloxy, $C_{1-8}$alkoxy$C_{1-8}$alkyloxy, ester group-$C_{1-8}$alkyloxy, $C_{1-8}$alkylamino, $(C_{1-8}$alkyl$)_2$amino, amino$C_{1-8}$alkylamino, (amino$C_{1-8}$alkyl$)_2$amino, $C_{1-8}$alkylester group, aminocarbonyl, $C_{1-8}$alkylaminocarbonyl, $(C_{1-8}$alkyl$)_2$aminocarbonyl, $C_{1-8}$alkylcarbonyl, $C_{1-8}$alkylcarbonyloxy, $C_{1-8}$alkylcarbonylamino, $C_{1-8}$alkylsulfamido, halo$C_{1-8}$alkyl, halo$C_{1-8}$alkyloxy, $C_{1-8}$alkylsulfonyl, $C_{1-8}$alkylsulfinyl, $C_{1-8}$alkylthio, 3-12 membered cycloalkyl, 6-14 membered aryl, 3-12 membered heterocyclyl, 5-14 membered heteroaryl and oxo,

in the five-membered ring (the ring denoted by P in the general formula (II), which is denoted by the same symbol below) and the six-membered ring (the ring denoted by A in the general formula (II), which is denoted by the same symbol below) represents a double bond optionally present in the ring;

provided that when $R^1$ represents the $C_{1-8}$alkyl substituted by a substituent, and the substituent contains hydroxyl, each carbon atom of the $C_{1-8}$alkyl carries at least one hydrogen;

when $R^1$ represents the $C_{1-8}$alkyl substituted by a substituent, and the substituent contains hydroxyl, the five-membered ring does not represent the imidazole ring group; when $R^1$ represents the $C_{1-8}$alkyl substituted by a substituent, and the substituent contains amino, $C_{1-8}$alkylamino or $(C_{1-8}$alkyl$)_2$amino, at least one of X and Y represents 6-14 membered aryl group optionally substituted by a substituent group;

when the five-membered ring is the thiophene ring group, m is not 0;

when the five-membered ring contains one nitrogen atom, the five-membered ring is bonded to X through a non-nitrogen atom;

when $R^1$ represents —($C_{0-8}$alkyl optionally substituted by a substituent group)C(O)NR$^4$R$^5$, neither X nor Y is a bond, the five-membered ring represents the furan ring group, and m is not 0.

In another embodiment of the present invention, there is provided a compound represented by the general formula (II), a pharmaceutically acceptable salt thereof, an ester thereof, a prodrug thereof, a solvate thereof, or a deuterated analog thereof, or a stereoisomer thereof, wherein said compound is a compound represented by the following general formula (III):

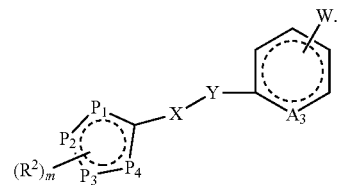

In another embodiment of the present invention, there is provided a compound represented by the general formula (II), a pharmaceutically acceptable salt thereof, an ester thereof, a prodrug thereof, a solvate thereof, or a deuterated analog thereof, or a stereoisomer thereof, wherein said compound is a compound represented by the following general formula (IV):

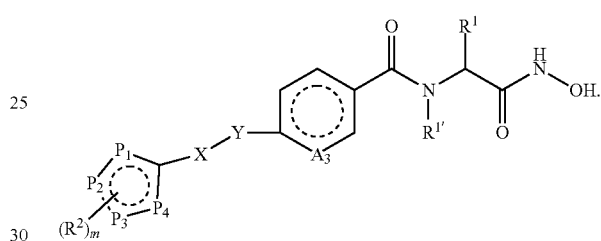

In another embodiment of the present invention, there is provided a compound represented by the general formula (II), a pharmaceutically acceptable salt thereof, an ester thereof, a prodrug thereof, a solvate thereof, or a deuterated analog thereof, or a stereoisomer thereof, wherein said compound is a compound represented by the following general formula (V) or (VI):

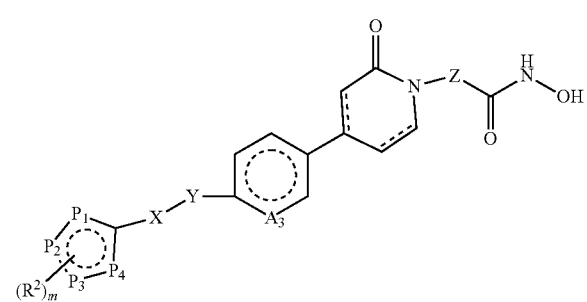

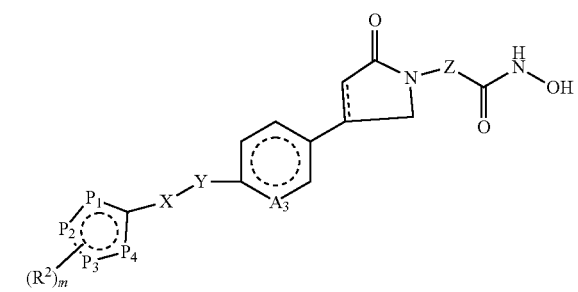

wherein, Z represents $C_{1-8}$alkyl optionally substituted by $R^1$, === represents a single bond or a double bond.

In another embodiment of the present invention,

in the ring P in the general formula (II) represents the presence of at least one double bond in the ring.

In another embodiment of the present invention, the ring P in the general formula (II) is a heteroaryl ring.

In another embodiment of the present invention,

in the ring A in the general formula (II) represents the presence of at least one double bond in the ring.

In another embodiment of the present invention, A in the general formula (II) is the benzene ring or the heteroaryl ring.

In another embodiment of the present invention, W represents ($C_{0-8}$alkyl optionally substituted by a substituent group)

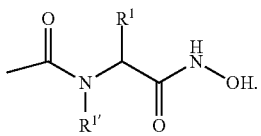

In another embodiment of the present invention, $R^1$ in the general formula (II) is each independently selected from a group consisting of $C_{1-8}$alkyl optionally substituted by a substituent group, —$(CH_2)_{0-4}C(R^{1a},R^{1b})(CH_2)_{0-4}OR^3$, —$(CH_2)_{0-4}C(R^{1a},R^{1b})(CH_2)_{0-4}NR^3R^3$, —$(CH_2)_{0-4}C(O)NR^4R^5$ and —$(CH_2)_{0-4}S(O)_{1-2}R^3$.

In another embodiment of the present invention, $R^1$ in the general formula (II) is each independently selected from a group consisting of $C_{1-4}$alkyl optionally substituted by a substituent group, —($C_{1-4}$alkyl optionally substituted by a substituent group)$OR^3$, —($C_{1-4}$alkyl optionally substituted by a substituent group)$NR^4R^5$ and —($C_{0-4}$alkyl optionally substituted by a substituent group)$C(O)NR^4R^5$ and —($C_{1-4}$alkyl optionally substituted by a substituent group)$S(O)_{1-2}R^3$.

In another embodiment of the present invention, $R^1$ in the general formula (II) is each independently selected from a group consisting of methyl, ethyl, propyl, isopropyl, butyl, sec-butyl, tert-butyl, hydroxymethyl, hydroxyethyl, hydroxypropyl, isohydroxypropyl, hydroxybutyl, hydroxy-sec-butyl, hydroxytert-butyl, aminomethyl, aminoethyl, aminopropyl, isoaminopropyl, aminobutyl, aminosec-butyl, aminotert-butyl, —$(CH_2)_{0-4}C(O)NH_2$ and —$(CH_2)_{0-4}S(O)_2C_{1-4}$alkyl.

In another embodiment of the present invention, $R^{1a}$ and $R^{1b}$ in the general formula (II) are each independently selected from a group consisting of hydrogen atom, amino, hydroxyl and $C_{1-8}$alkyl optionally substituted by a substituent group. Preferably, $R^{1a}$ and $R^{1b}$ in the general formula (II) are each independently selected from a group consisting of hydrogen atom, amino, hydroxyl, methyl, ethyl, propyl, isopropyl, butyl, sec-butyl and tert-butyl.

In another embodiment of the present invention, $R^3$, $R^4$ and $R^5$ in the general formula (II) are each independently selected from a group consisting of hydrogen atom and $C_{1-8}$alkyl optionally substituted by a substituent group. Preferably, $R^3$, $R^4$ and $R^5$ in the general formula (II) are each independently selected from a group consisting of hydrogen atom, methyl, ethyl, propyl, isopropyl, butyl, sec-butyl and tert-butyl.

In another embodiment of the present invention, $R^{1'}$ in the general formula (II) is selected from a group consisting of hydrogen atom, hydroxyl, halogen atom and $C_{1-8}$alkyl.

In another embodiment of the present invention, $R^{1'}$ in the general formula (II) and the carbon atom in the $C_{0-8}$alkyl optionally substituted by a substituent group in the group W, together with the groups N and C(O), form 5-6 membered unsaturated heterocyclic group.

In another embodiment of the present invention, $R^{1'}$ in the general formula (II) is selected from a group consisting of hydrogen atom, methyl, ethyl, propyl, isopropyl, butyl, sec-butyl and tert-butyl.

In another embodiment of the present invention, $R^{1'}$ in the general formula (II) and the carbon atom in the $C_{0-8}$alkyl optionally substituted by a substituent group in the group W, in with the groups N and C(O), form 6 membered unsaturated heterocyclic group.

In another embodiment of the present invention, in the ring A in the general formula (II), the group attached to the group W is a carbon atom.

In another embodiment of the present invention, the ring A in the general formula (II) is selected from a group consisting of a benzene ring, a pyridine ring, a pyrimidine ring, a pyridazine ring, a pyrazine ring and a triazine ring.

In another embodiment of the present invention, in the general formula (II), X and Y are each independently selected from a group consisting of a bond, a benzene ring group optionally substituted by a substituent group, a pyrrole ring group optionally substituted by a substituent group, a pyrazole ring group optionally substituted by a substituent group, a 1,2,3-triazole ring group optionally substituted by a substituent group, a 1,2,4-triazole ring group optionally substituted by a substituent group, a tetrazole ring group optionally substituted by a substituent group, a furan ring group optionally substituted by a substituent group, a thiophene ring group optionally substituted by a substituent group, an oxazole ring group optionally substituted by a substituent group, an isoxazole ring group optionally substituted by a substituent group, a 1,2,4-oxadiazole ring group optionally substituted by a substituent group, a pyridine ring group optionally substituted by a substituent group, an indole ring group optionally substituted by a substituent group, —(C=C)—, —(C≡C)—, =N—, —C(O)—$NR^c$—,

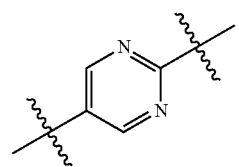 [SMILES: *c1cnc(*)nc1]

optionally substituted by a substituent group,

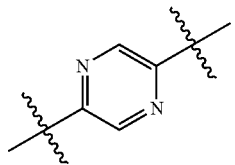 [SMILES: *c1cnc(*)cn1]

optionally substituted by a substituent group and

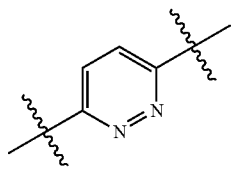 [SMILES: *c1ccc(*)nn1]

optionally substituted by a substituent group, wherein at least one of X and Y is not a bond.

In another embodiment of the present invention, X and Y in the general formula (II) are not simultaneously the 6-14 membered aryl group optionally substituted by a substituent group. Preferably, X and Y in the general formula (II) are not simultaneously the benzene ring group optionally substituted by a substituent group.

In another embodiment of the present invention, in the general formula (II), when one of X and Y represents a bond, the other does not represent the 6-14 membered aryl group optionally substituted by a substituent group. Preferably, in the general formula (II), when one of X and Y represents a bond, the other does not represent the benzene ring group optionally substituted by a substituent group.

In another embodiment of the present invention, when one of X and Y represents a bond, the other represents —(C≡C)—.

In another embodiment of the present invention, in the general formula (II), at least one of X and Y is —(C=C)— or —(C≡C)—.

In another embodiment of the present invention, neither X nor Y represents a bond.

In another embodiment of the present invention, in the ring P in the general formula (II), the group attached to the group X is a carbon atom.

In another embodiment of the present invention, at least one of $P_1$, $P_2$, $P_3$, $P_4$ and $P_5$ is a group selected from a group consisting of $NR^c$, O and S.

In another embodiment of the present invention, the ring P in the general formula (II) is selected from a group consisting of a pyrroline ring group, a pyrrolidine ring group, an imidazoline ring group, an imidazolidine ring group, a pyrazoline ring group, a pyrazolidine ring group, a pyrrole ring group, a pyrazole ring group, a 1,2,3-triazole ring group, a 1,2,4-triazole ring group, a thiophene ring group, a thiazole ring group, an isothiazole ring group, a 1,2,4-thiadiazole ring group, an oxazole ring group, an isoxazole ring group and a 1,2,4-oxadiazole ring group.

In another embodiment of the present invention, the ring P in the general formula (II) is selected from a group consisting of a furan group, a pyrrole group, a pyrazole group, a triazole group and a thiophene group.

In another embodiment of the present invention, B in the general formula (II), in each occurrence, is each independently selected from a group consisting of a bond, $C_{1-8}$alkyl optionally substituted by a substituent group and $C_{1-8}$alkyl in which at least one carbon atom is replaced with at least one group from O and $NR^c$ and optionally substituted by a substituent group.

In another embodiment of the present invention, C in the general formula (II), in each occurrence, each independently represents hydrogen atom, $C_{1-8}$alkyl optionally substituted by a substituent group, —$OR^c$, —$NR^cR^c$, 3-10 membered cycloalkyl optionally substituted by a substituent group, 3-10 membered heterocyclyl optionally substituted by a substituent group, 5-10 membered heteroaryl optionally substituted by a substituent group and 6-10 membered aryl optionally substituted by a substituent group.

In another embodiment of the present invention, C in the general formula (II), in each occurrence, is each independently selected from a group consisting of hydrogen atom, $C_{1-4}$alkyl optionally substituted by a substituent group, —$OR^c$, —$NR^cR^c$, 3-8 membered cycloalkyl optionally substituted by a substituent group, 3-8 membered heterocyclyl optionally substituted by a substituent group, 5-6 membered heteroaryl optionally substituted by a substituent group and 6-10 membered aryl optionally substituted by a substituent group.

In another embodiment of the present invention, C in the general formula (II) can be the following groups optionally substituted by a substituent group:

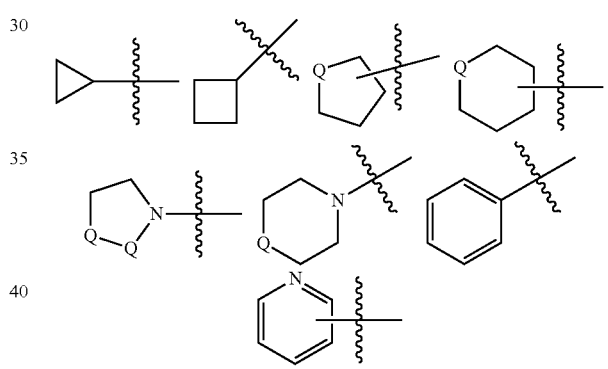

wherein, Q is a group selected from a group consisting of $CR^aR^a$, $NR^c$, O and S.

In another embodiment of the present invention, m in the general formula (II) is 0, 1, 2 or 3.

In another embodiment of the present invention, when $R^1$ in the general formula (II) represents —($C_{0-8}$alkyl optionally substituted by a substituent group)C(O)$NR^4R^5$, both X and Y represent —(C≡C)—, P represents a furan ring group, and m is not 0.

In another embodiment of the present invention, when $R^1$ in the general formula (II) represents $C_{1-8}$alkyl substituted by a substituent group, and the substituent group contains amino, $C_{1-8}$alkylamino or $(C_{1-8}alkyl)_2$amino, at least one of X and Y represents 6-14 membered aryl group optionally substituted by a substituent group, and the ring P represents a pyrazole ring group.

In another embodiment of the present invention, the ring P does not represent an imidazole ring group.

In another embodiment of the present invention, when X is selected from a group consisting of —(C=C)—, —(C≡C)—, 5-10 membered heteroaryl group optionally substituted by a substituent group and 6-10 membered aryl group optionally substituted by a substituent group, Y is selected from a group consisting of a bond, —(C═C)— and —(C≡C)—, and Y represents a bond, X does not represent 6-10 membered aryl group optionally substituted by a substituent group.

In another embodiment of the present invention, either $R^a$ in the general formula (II) is absent, or in each occurrence is each independently selected from a group consisting of hydrogen atom, cyano, mercapto, halogen atom, carboxyl, nitro, —$OR^c$, —$NR^cR^c$, —$C(O)OR^c$, —$S(O)_{1-2}$—$OR^c$, $C_{1-4}$alkyl optionally substituted by a substituent group, —($C_{1-4}$alkyl optionally substituted by a substituent group) $OR^c$, —($C_{1-4}$alkyl optionally substituted by a substituent group)$NR^cR^c$, $C_{1-4}$alkyloxy optionally substituted by a substituent group, $C_{2-4}$alkenyl optionally substituted by a substituent group, $C_{2-4}$alkynyl optionally substituted by a substituent group, 3-10 membered cycloalkyl optionally substituted by a substituent group, 3-10 membered heterocyclyl optionally substituted by a substituent group, 6-10 membered aryl optionally substituted by a substituent group and 5-10 membered heteroaryl optionally substituted by a substituent group.

In another embodiment of the present invention, either $R^a$ in the general formula (II) is absent, or in each occurrence is each independently selected from a group consisting of hydrogen atom, halogen atom, carboxyl, nitro, hydroxyl, amino, methyl, ethyl, propyl, isopropyl, butyl, sec-butyl, tert-butyl, hydroxymethyl, hydroxyethyl, hydroxypropyl, isohydroxypropyl, hydroxybutyl, hydroxysec-butyl, hydroxytert-butyl, aminomethyl, aminoethyl, aminopropyl, isoaminopropyl, aminobutyl, aminosec-butyl, aminotert-butyl, methoxy, ethoxy, propoxy, isopropoxy, butoxy, sec-butoxy, tert-butoxy, 3-6 membered cycloalkyl optionally substituted by a substituent group, 3-6 membered heterocyclyl optionally substituted by a substituent group, 6-10 membered aryl optionally substituted by a substituent group and 5-6 membered heteroaryl optionally substituted by a substituent group.

In another embodiment of the present invention, either $R^c$ in the general formula (II) is absent, or in each occurrence is each independently selected from a group consisting of hydrogen atom, halogen atom, carboxyl, $C_{1-4}$alkyl optionally substituted by a substituent group, —($C_{1-4}$alkyl optionally substituted by a substituent group)$OR^b$, —($C_{1-4}$alkyl optionally substituted by a substituent group)$NR^bR^b$, $C_{2-4}$alkenyl optionally substituted by a substituent group, $C_{2-4}$alkynyl optionally substituted by a substituent group, 3-10 membered cycloalkyl optionally substituted by a substituent group, 3-10 membered heterocyclyl optionally substituted by a substituent group, 6-10 membered aryl optionally substituted by a substituent group and 5-10 membered heteroaryl optionally substituted by a substituent group, or in case that two $R^c$ groups are attached to the same atom, two $R^c$ groups, together with the atom attached thereto, form 3-10 membered heterocycle optionally substituted by a substituent group.

In another embodiment of the present invention, either $R^c$ in the general formula (II) is absent, or in each occurrence is each independently selected from a group consisting of hydrogen atom, methyl, ethyl, propyl, isopropyl, butyl, sec-butyl, tert-butyl, hydroxymethyl, hydroxyethyl, hydroxypropyl, isohydroxypropyl, hydroxybutyl, hydroxysec-butyl, hydroxytert-butyl, aminomethyl, aminoethyl, aminopropyl, isoaminopropyl, aminobutyl, aminosec-butyl, aminotert-butyl, 3-6 membered cycloalkyl optionally substituted by a substituent group, 3-6 membered heterocyclyl optionally substituted by a substituent group, 6-10 membered aryl optionally substituted by a substituent group and 5-6 membered heteroaryl optionally substituted by a substituent group, or in case that two $R^c$ groups are attached to the same atom, two $R^c$ groups, together with the atom attached thereto, form 3-6 membered heterocycle optionally substituted by a substituent group.

In another embodiment of the present invention, $R^b$ in the general formula (II), in each occurrence, is each independently selected from a group consisting of hydrogen atom, halogen atom, carboxyl, sulfonic acid group, $C_{1-4}$alkyl optionally substituted by a substituent group, $C_{1-4}$alkylsulfonyl optionally substituted by a substituent group, 3-10 membered cycloalkyl optionally substituted by a substituent group, 3-10 membered heterocyclyl optionally substituted by a substituent group, 6-10 membered aryl optionally substituted by a substituent group and 5-10 membered heteroaryl optionally substituted by a substituent group.

In another embodiment of the present invention, $R^b$ in the general formula (II), in each occurrence, is each independently selected from a group consisting of hydrogen atom, halogen atom, carboxyl, methyl, ethyl, propyl, isopropyl, butyl, sec-butyl, tert-butyl, 3-6 membered cycloalkyl optionally substituted by a substituent group, 3-6 membered heterocyclyl optionally substituted by a substituent group, 6-10 membered aryl optionally substituted by a substituent group and 5-6 membered heteroaryl optionally substituted by a substituent group.

In another embodiment of the present invention, $R^d$ in the general formula (II), in each occurrence, is each independently selected from a group consisting of hydrogen atom, hydroxyl, mercapto, halogen atom, carboxyl, nitro, amino, $C_{1-4}$alkylamino optionally substituted by a substituent group, ($C_{1-4}$alkyl optionally substituted by a substituent group)$_2$amino, sulfonic acid group, $C_{1-4}$alkyl optionally substituted by a substituent group, $C_{1-4}$alkyloxy optionally substituted by a substituent group, $C_{1-4}$alkylsulfonyl optionally substituted by a substituent group, 3-10 membered cycloalkyl optionally substituted by a substituent group, 3-10 membered heterocyclyl optionally substituted by a substituent group, 6-10 membered aryl optionally substituted by a substituent group and 5-10 membered heteroaryl optionally substituted by a substituent group.

In another embodiment of the present invention, $R^d$ in the general formula (II), in each occurrence, is each independently selected from a group consisting of hydrogen atom, hydroxyl, mercapto, halogen atom, amino, sulfonic acid group, methyl, ethyl, propyl, isopropyl, butyl, sec-butyl, tert-butyl, methoxy, ethoxy, propoxy, isopropoxy, butoxy, sec-butoxy, tert-butoxy, 3-6 membered cycloalkyl optionally substituted by a substituent group, 3-6 membered heterocyclyl optionally substituted by a substituent group, 6-10 membered aryl optionally substituted by a substituent group and 5-6 membered heteroaryl optionally substituted by a substituent group.

In another embodiment of the present invention, the substituent group in "optionally substituted by a substituent group" is each independently selected from a group consisting of hydroxyl, mercapto, carboxyl, cyano, nitro, amino, halogen atom, sulfonic acid group, $C_{1-4}$alkyl, $C_{1-4}$alkoxy$C_{1-4}$alkyl, hydroxy$C_{1-4}$alkyl, amino$C_{1-4}$alkyl, carboxy$C_{1-4}$alkyl, ester group-$C_{1-4}$alkyl, $C_{1-4}$alkyloxy, hydroxy$C_{1-4}$alkyloxy, amino$C_{1-4}$alkyloxy, carboxy$C_{1-4}$alkyloxy, $C_{1-4}$alkyl$C_{1-4}$alkyloxy, $C_{1-4}$alkoxy$C_{1-4}$alkyloxy, ester group-$C_{1-4}$alkyloxy, $C_{1-4}$alkylamino, ($C_{1-4}$alkyl)$_2$amino, amino$C_{1-4}$alkylamino, (amino$C_{1-4}$alkyl)$_2$amino, $C_{1-4}$alkyl-ester group, aminocarbonyl, $C_{1-4}$alkylaminocarbonyl, ($C_{1-4}$alkyl)$_2$aminocarbonyl, $C_{1-4}$alkylcarbonyl, $C_{1-4}$alkylcarbonyloxy, $C_{1-4}$alkylcarbonylamino, $C_{1-4}$alkylcarbonylamino, $C_{1-4}$alkylsulfamido, halo$C_{1-4}$alkyl, halo$C_{1-4}$alkyloxy, $C_{1-4}$alkylsulfonyl, $C_{1-4}$alkylsulfinyl, $C_{1-4}$alkylthio, 3-10 membered cycloalkyl, 6-10 membered aryl, 3-10 membered heterocyclyl, 5-10 membered heteroaryl and oxo.

In another embodiment of the present invention, the substituent group in "optionally substituted by a substituent group" is each independently selected from a group consisting of hydroxyl, mercapto, carboxyl, cyano, nitro, amino, halogen atom, sulfonic acid group, methyl, ethyl, propyl, isopropyl, butyl, sec-butyl, tert-butyl, hydroxymethyl, hydroxyethyl, hydroxypropyl, isohydroxypropyl, hydroxybutyl, hydroxysec-butyl, hydroxytert-butyl, aminomethyl, aminoethyl, aminopropyl, isoaminopropyl, aminobutyl, aminosec-butyl, aminotert-butyl, methoxy, ethoxy, propoxy, isopropoxy, butoxy, sec-butoxy, tert-butoxy, halomethyl, haloethyl, halopropyl, haloisopropyl, halobutyl, halosec-butyl, halotert-butyl, halomethoxy, haloethoxy, halopropoxy, haloisopropoxy, halobutoxy, halosec-butoxy, halotert-butoxy, 3-6 membered cycloalkyl, 6-10 membered aryl, 3-6 membered heterocyclyl, 5-6 membered heteroaryl and oxo.

Effects of the Invention

The compound of the present invention is an inhibitor compound of UDP-3-O—(R-hydroxytetradecanoyl)-N-acetylglucosamine deacetylase (LpxC). The compound of the present invention can achieve the excellent antibacterial activity, and especially show excellent antibacterial activity against Gram bacteria.

In addition, compared with the closest prior art, the compound of the present invention has the following advantages:

(1) The compound of the present invention, a pharmaceutically acceptable salt thereof, an ester thereof, a prodrug thereof, a solvate thereof, or a deuterated analog thereof, or a stereoisomer thereof has good anti-Gram-negative bacteria activity;

(2) The compound of the present invention, a pharmaceutically acceptable salt thereof, an ester thereof, a prodrug thereof, a solvate thereof, or a deuterated analog thereof, or a stereoisomer thereof shows good biological stability and has excellent metabolic stability in vivo;

(3) The compound of the present invention, a pharmaceutically acceptable salt thereof, an ester thereof, a prodrug thereof, a solvate thereof, or a deuterated analog thereof, or a stereoisomer thereof can be easily prepared and has stable quality.

DETAILED DESCRIPTION OF THE INVENTION

The embodiments of the present invention will be described in more detail below with reference to the specific embodiments, but those skilled in the art will understand that the specific embodiments described below are only used to illustrate the invention, and should not be regarded as the limit to the protection scope of the present invention. Rather, the invention is intended to cover all alternatives, modifications and equivalents, which are included in the scope of the invention as defined by the appended claims.

Embodiments of the invention may be combined in any manner, unless otherwise stated. Conversions, variations, and modifications of the technical solutions thus obtained are also included in the scope of the present invention and do not depart from the scope of the present invention.

All publications, patent applications, patents and other references mentioned in this specification are hereby incorporated by reference. Unless otherwise defined, all technical and scientific terms used in the specification have the meaning conventionally understood by those skilled in the art. In case of conflict, the definition of this specification shall prevail.

In the context of the present specification, unless otherwise explicitly defined, any features or technical means not discussed specifically will be understood with the meanings known in the art without any substantive modification. Moreover, any embodiment described in the specification can be associated freely with one or more other embodiments described in the specification, and the technical solution or idea formed therefrom is deemed as a part of the original disclosure or original record, but cannot be considered as a new content not disclosed or expected by the specification, unless those skilled in the art believe that the combination is obviously unfeasible.

In the present invention, the expression "$C_{a-b}$ group" (a and b represent integers of zero or more, a<b) means that the "group" has a-b carbon atoms, for example, $C_{1-4}$alkyl represents an alkyl having 1-4 carbon atoms, $C_{1-4}$alkoxy represents an alkoxy having 1-4 carbon atoms, $C_{3-10}$cycloalkyl represents a cycloalkyl having 3-10 carbon atoms, and $C_{1-4}$alkoxy$C_{1-4}$alkyl represents a group formed by attaching an alkoxy having 1-4 carbon atoms to an alkyl having 1-4 carbon atoms. When the subscript of C is 0, it means that the $C_0$ group does not exist. For example, in "—$C_a$alkylNH$_2$", when a is 0, it means "—NH$_2$". In the present invention, "(group)$_{a-b}$" (a and b represent an integer of zero or more, a<b) means there are a-b "groups", when the subscript is 0, it means that the group does not exist, for example —S(O)$_{0-2}$ means that 0, 1 or 2 oxygen atoms can be bonded to S, that is, —S—, —S(O)—, —S(O)$_2$—. For example, —(CH$_2$)$_{0-2}$OH means —OH, —CH$_2$OH, —(CH$_2$)$_2$OH.

In the present invention, "C(R$^{1a}$, R$^{1b}$)" means that R$^{1a}$ and R$^{1b}$ are each bonded to the carbon atom. For example, "—C(H,CH$_3$)OH" means that the H atom and —CH$_3$ are each bonded to the carbon atom, i.e., the group

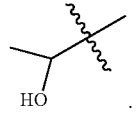 [SMILES: *C(C)O]

In the following explanation, the meaning of the group with the subscript of 0 is not explained, and the explanation starts with the meaning of the group with the subscript of 1. For example, for the explanation of the group $C_{0-8}$alkyl, since the group $C_0$ means that the alkyl group does not exist, the explanation starts from the group $C_1$alkyl.

In the present invention, "yl" and "group" mean a monovalent group or a divalent or higher valent group which conforms to the valence rule as required, for example, "cycloalkyl (also expressed as cycloalkyl group)" includes a monovalent group obtained by removing one hydrogen atom from a cycloalkane, or a divalent or higher group obtained by removing two or more hydrogen atoms from the same carbon atom or two or more different carbon atoms of a cycloalkane. For example, when "cycloalkyl" is used as a terminal group, if it does not carry a substituent, it is connected to the rest of the structural formula in the form of a monovalent group; and if it carries one or more substituents, according to the number of the carried substituent(s), the cycloalkyl exhibits a corresponding number of valences (the number of the substituent(s)+1). Those skilled in the art can unambiguously determine the number of valences represented by "yl" and "group".

As used herein, the term "halogen atom" refers to a fluorine atom, a chlorine atom, a bromine atom, or an iodine atom. It is preferably a fluorine atom, a chlorine atom or a bromine atom.

As used herein, the term "halo" means one or more hydrogen atoms on any carbon atom in a substituent group can be substituted by one or more same or different halogen atoms, and the substitution can be a monohalogenation, a polyhalogenation, or a perhalogenation, i.e., all positions in the group that can be substituted are substituted with halogen atoms. As used herein, the term "$C_{1-8}$alkyl" refers to a linear or branched alkyl having one valence or two or higher valence as needed obtained derivatively by removing one or more hydrogen atoms from an alkane containing 1-8 carbon atoms. As an example of the alkyl group, for example, the following can be exemplified: methyl, ethyl, n-propyl, iso-propyl, n-butyl, isobutyl, sec-butyl, tert-butyl, n-pentyl, iso-pentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like. "$C_{1-8}$alkyl" can comprise $C_{1-6}$alkyl, $C_{1-4}$alkyl, and $C_{1-3}$alkyl. The "$C_{1-6}$alkyl" according to the present invention refers to the above examples having 1-6 carbon atoms; the "$C_{1-4}$alkyl" according to the present invention refers to the above examples having 1-4 carbon atoms; and the "$C_{1-3}$alkyl" according to the present invention refers to the above examples having 1-3 carbon atoms.

As used herein, the term "$C_{2-8}$alkenyl" refers to an alkenyl having one valence or two or higher valence as needed obtained derivatively by removing one or more hydrogen atoms from a linear or branched alkene containing at least one carbon-carbon double bond and 2-8 carbon atoms. For example, the following can be exemplified: ethenyl, 1-propenyl, 2-propenyl, 1-butenyl, 2-butenyl, 1,3-butadien-1-yl, 1-penten-3-yl, 2-penten-1-yl, 3-penten-1-yl, 3-penten-2-yl, 1,3-pentadien-1-yl, 1,4-pentadien-3-yl, 1-hexen-3-yl, 1,4-hexadien-1-yl. Preferably, "$C_{2-8}$alkenyl" contains one carbon-carbon double bond. "$C_{2-4}$alkenyl" refers to the above examples having 2-4 carbon atoms.

As used herein, the term "$C_{2-8}$alkynyl" refers to an alkynyl having one valence or two or higher valence as needed obtained derivatively by removing one or more hydrogen atoms from a linear or branched alkyne containing at least one carbon-carbon triple bond and 2-8 carbon atoms. For example, the following can be exemplified: ethynyl, propynyl, 2-butyn-1-yl, 2-pentyn-1-yl, 3-pentyn-1-yl, 4-methyl-2-pentyn-1-yl, 2-hexyn-1-yl, 3-hexyn-1-yl, 3-hexyn-2-yl and the like. Preferably, "$C_{2-8}$alkynyl" contains one carbon-carbon triple bond. "$C_{2-4}$alkynyl" refers to the above examples having 2-4 carbon atoms. As used herein, the term "$C_{1-8}$alkoxy" refers to the group obtained from the above-defined "$C_{1-8}$alkyl" by attaching to the parent group via an oxygen atom, i.e. the group "$C_{1-8}$alkyl-O—". For example, the following can be exemplified: methoxy, ethoxy, n-propoxy, isopropoxy, n-butoxy, tert-butoxy, n-pentyloxy, neo-pentyloxy and n-hexyloxy, heptyloxy and the like. "$C_{1-4}$alkoxy" refers to the above examples having 1-4 carbon atoms, i.e., the group "$C_{1-4}$alkyl-O—".

As used herein, the groups "$C_{1-8}$alkyl" contained in the terms "$C_{1-8}$alkyl$C_{1-8}$alkoxy", "$C_{1-8}$alkylamino", "($C_{1-8}$alkyl)$_2$amino", "$C_{1-8}$alkyl-ester group", "$C_{1-8}$alkylaminocarbonyl", "halo$C_{1-8}$alkyl" and the like refer to the groups obtained by attaching the above-mentioned "$C_{1-8}$alkyl" of the present invention to the corresponding groups such as "$C_{1-8}$alkoxy", "amino", "ester group", "aminocarbonyl", and "halogen atom" respectively. Similarly, the expressions containing the group "$C_{1-4}$alkyl" refer to the groups obtained by attaching the above-mentioned "$C_{1-4}$alkyl" of the present invention to the corresponding groups. Similarly, the expressions containing the groups "$C_{1-8}$alkoxy" and "$C_{1-4}$alkoxy" refer to the groups obtained by attaching the above-mentioned "$C_{1-8}$alkoxy" and "$C_{1-4}$alkoxy" of the present invention to the corresponding groups.

In the present invention, the cyclic group may be a monocyclic ring system or a polycyclic ring system. In the case of the polycyclic ring system, two or more rings are connected by means of a bridged ring, a spiro ring, and a fused ring. Said bridged ring refers to a polycyclic ring structure formed from two or more cyclic structures by sharing two non-adjacent ring atoms with each other. Said spiro ring refers to a polycyclic ring structure formed from two or more cyclic structures by sharing one ring atom with each other. Said fused ring refers to a polycyclic ring structure formed from two or more cyclic structures by sharing two adjacent ring atoms with each other (i.e. commonly using one same bond). As used herein, the term "3-12 membered cycloalkyl" refers to a saturated cyclic alkane group having 3, 4, 5, 6, 7, 8, 9, 10, 11 or 12 ring-forming carbon atoms, which can be a monovalent group or a divalent or higher valent group (as needed) and can be a monocyclic system, or a polycyclic system. "3-12 membered cycloalkyl" of the present invention can comprise 3-12 membered cycloalkyl, 3-10 membered cycloalkyl, 3-8 membered cycloalkyl, 3-6 membered cycloalkyl. The example of cycloalkyl of the present invention includes but is not limited to cyclopropyl, cyclobutyl, cyclopentyl, cyclohexyl, cycloheptyl, cyclooctylyl, cyclopent-1,3-diyl, cyclohex-1,4-diyl, cyclohex-1,4-diyl, norbornyl, adamantyl; a monovalent group or a divalent or higher valent group derivatives obtained from bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane, a monovalent group or a divalent or higher valent group derived by removing one hydrogen atom or two or more hydrogen atoms as needed from the following spiro rings:

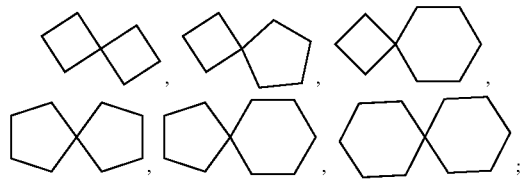

a monovalent group or a divalent or higher valent group derived by removing one hydrogen atom or two or more hydrogen atoms as needed from the following bridged rings:

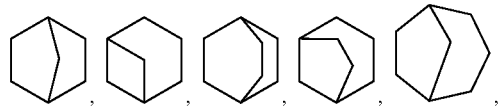

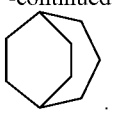

As used herein, the term "3-12 membered heterocycle" refers to a non-aromatic cyclic hydrocarbon containing at least one (for example, 1-5, 1-4, 1-3, 1-2 or 1) group(s) selected from a group consisting of O, S, and N as the ring-forming atom in the ring, provided that the ring(s) of said group does not contain two adjacent O or S atoms. It can be a heterocycle having 3, 4, 5, 6, 7, 8, 9, 10, 11 or 12 ring-forming atoms. Optionally, at least one double bond can be present in the ring to form an unsaturated heterocyclyl. In addition, in the heterocycle of the present invention, the ring-forming atoms can be optionally oxidized, that is, C and S as the ring-forming atoms can form the groups C(O), S(O), S(O)$_2$. The heterocycle of the present invention can be a monocyclic system, and can also be a polycyclic system. As an example of heterocycle, the following can be exemplified: the monocyclic heterocycle such as oxirane, thietane, oxetane, 1,2-dioxetane, thietane, aziridine, 1,2-diazetidine, azete, 1,2-diazetidine, pyrroline (4,5-dihydropyrrole, 2,5-dihydropyrrole), pyrrolidine, imidazoline (4,5-dihydroimidazole), imidazolidine, pyrazoline (4,5-dihydropyrazole), pyrazolidine, piperidine, piperazine, morpholine, thiomorpholine, tetrahydropyran, dihydropyridine, dihydropyridazine, dioxane, oxathiolane, cyclopentanethione/tetrahydrothiophene, tetrahydrofuran, tetrahydrothiazole, tetrahydroisothiazole, 2-pyridinone, 4-pyridinone, azepine, 1,2-diazepine, 1,3-diazepine, 1,4-diazepine, azocine, 1,4-dihydro-1,4-diazocine, 1,2-dithiete, 4,5-dihydrofuran, 2,5-dihydrofuran, 2,5-dihydrothiophene, 4,5-dihydrothiophene, 1,2-dithiole, 1,3-dithiole, 2H-pyran, 2H-pyran-2-one, 3,4-dihydro-2H-pyran, 4H-pyran, 4H-pyran-4-one, 1,4-dioxine, 1,4-dithiine, 1,4-oxathiine, oxepine, thiepine, 1,4-dioxocine, 4,5-dihydrooxazole, 2,3-dihydrooxazole, 4,5-dihydroisoxazole, 2,3-dihydroisoxazole, 4,5-dihydrothiazole, 2,3-dihydrothiazole, 2H-1,2-oxazine, 4H-1,2-oxazine, 6H-1,2-oxazine, 2H-1,3-oxazine, 4H-1,3-oxazine, 5,6-dihydro-4H-1,3-oxazine, 6H-1,3-oxazine, 2H-1,4-oxazine, 4H-1,4-oxazine, 2H-1,3-thiazine, 4H-1,3-thiazine, 5,6-dihydro-4H-1,3-thiazine, 6H-1,3-thiazine, 2H-1,4-thiazine, and 4H-1,4-thiazine; and the fused heterocycle such as dihydroindole, isodihydroindole, benzopyran, benzodioxane, tetrahydroquinoline, benzo[d]oxazole-2(3H)-one, tetrahydrobenzothiophene. Furthermore, the following can be exemplified: the heterocycles obtained by replacing at least one ring carbon atom in the spiro ring and the bridged ring exemplified in the above example of cycloalkyl with the heteroatom selected from a group consisting of O, S, and N.

As used herein, the term "3-12 membered heterocyclyl (heterocyclic group)" refers to a monovalent group or a divalent or higher valent group obtained derivatively by removing one or more hydrogen atoms from any ring-forming atom of the above-mentioned "3-12 membered heterocycle". "3-12 membered heterocyclyl" of the present invention can comprise a 3-10 membered heterocyclyl, a 3-8 membered heterocyclyl, a 3-6 membered heterocyclyl, or a 5-6 membered heterocyclyl.

As used herein, the term "6-14 membered aryl (aryl group)" refers to a monovalent group or a divalent or higher valent group having 6-14 ring-forming carbon atoms obtained derivatively from aromatic carbocyclic hydrocarbons. Among others, the 6-14 membered aryl is, for example, phenyl, naphthyl, phenanthryl, and anthracenyl. The 6-10 membered aryl is, for example, phenyl and naphthyl. When it is a divalent group, phenylene, naphthalene and the like can be exemplified.

As used herein, the term "5-14 membered heteroaryl (heteroaryl group)" refers to a monovalent cyclic hydrocarbyl or a divalent or higher valent cyclic hydrocarbyl (as needed) having the aromaticity and containing at least one (for example, 1-5, 1-4, 1-3, 1-2 or 1) heteroatom(s) selected from a group consisting of O, S, and N as the ring-forming atom, provided that the ring(s) of said group does not contain two adjacent O or S atoms. It can be a 5, 6, 7, 8, 9, 10, 11, 12, 13, or 14 membered heteroaryl group. In addition, in the heteroaryl of the present invention, the ring-forming atoms can be optionally oxidized, that is, C and S as the ring-forming atoms can form the groups C(O), S(O), S(O)$_2$, provided that the aromaticity is not influenced. In addition, the heteroaryl group of the present invention may be a monocyclic ring system or a polycyclic ring system. Specifically, the following can be exemplified: the monocyclic heteroaryl such as pyrrolyl, pyrazinyl, pyrazolyl, indolyl, tetrazolyl, furanyl, thienyl, pyridinyl, imidazolyl, 1,2,3-triazolyl, 1,2,4-triazolyl, tetrazolyl, triazinyl, pyridazinyl, pyrimidinyl, pyrazinyl, isooxazolyl, thiazolyl, isothiazolyl, thiadiazolyl (1,2,3-thiadiazolyl, 1,3,4-thiadiazolyl), oxazolyl, 1,2,3-oxadiazolyl, 1,2,5-oxadiazolyl, and 1,2,4-oxadiazolyl; and the following can also be exemplified: the fused heteroaryl group such as isoindolyl, indazolyl, indolizinyl, isodihydroindolyl, quinolinyl, isoquinolinyl, cinnolinyl, 2,3-naphthyridinyl, quinazolinyl, naphthyridinyl, quinoxalinyl, purinyl, pterridinyl, benzoimidazolyl, benzoisoxazolyl, benzoxazolyl, benzoxadiazolyl, benzoisothiazolyl, benzothiazolyl, benzothiadiazolyl, benzofuranyl, isobenzofuranyl, benzothienyl, benzotriazolyl, imidazolopyridinyl, triazolopyridinyl, imidazolothiazolyl, pyrazinopyridazinyl, and benzoimidazolinyl.

In the present invention, "C$_{1-8}$alkyl in which at least one carbon atom is replaced by at least one group of S, O, and NR$^e$" means that at least one carbon atom in "C$_{1-8}$alkyl" is replaced with at least one group selected from a group consisting of S, O, and NR, for example, C$_{1-s}$ alkyl in which two carbon atoms are replaced by two groups O and NR may be C$_2$alkyl-O—C$_2$alkyl-NR$^e$—C$_2$alkyl-.

The atom in the present invention includes all isotopes of the atom. Isotopes include those atoms that have the same atomic number but different mass numbers. As a general example and not as a limitation, isotopes of hydrogen include deuterium and tritium. Isotopes of carbon include $^{13}$C and $^{14}$C. Generally, the isotope-labeled compound of the present invention can be prepared by conventional techniques known to those skilled in the art or by methods similar to the methods described herein, using an appropriate isotope-labeled reagent instead of the originally used non-labeled reagent.

In the present invention, the "heteroatom" refers to an atom selected from a group consisting of S, O, and N.

In the present invention,

in the five-membered ring and the six-membered ring represent a double bond optionally present in the ring. There may be zero, one, two, or three double bonds. The maximum number of double bonds that can exist in the ring is taken as the limit. For example, in a five-membered ring, there may be zero double bond, one double bond or two double bonds; in the six-membered ring, there may be zero double bond, one double bond, two double bonds, or three double bonds.

In the present invention, "optionally substituted by a substituent" means that it may be unsubstituted or substituted. In the case of being substituted, it may be substituted by 1 substituent group, 2 substituent groups, 3 substituent groups, 4 substituent groups, 5 substituent groups, 6 substituent groups, 7 substituent groups, 8 substituent groups, or more substituent groups. In the case of being substituted by multiple substituent groups (two or more substituent groups), the substituent groups may be identical to or different from each other.

In one embodiment of the present invention, there is provided the following compounds, a pharmaceutically acceptable salt thereof, an ester thereof, a prodrug thereof, a solvate thereof, or a deuterated analog thereof, or a stereoisomer thereof:

| No. | Structure |
| --- | --- |
| 1 | 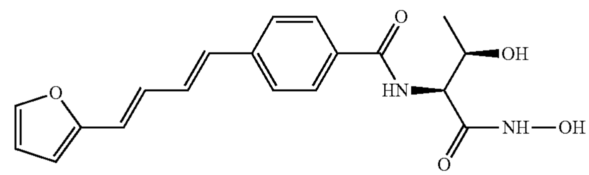 [SMILES: C[C@@H](O)[C@H](NC(=O)c1ccc(/C=C/C=C/c2ccco2)cc1)C(=O)NO] |
| 2 | 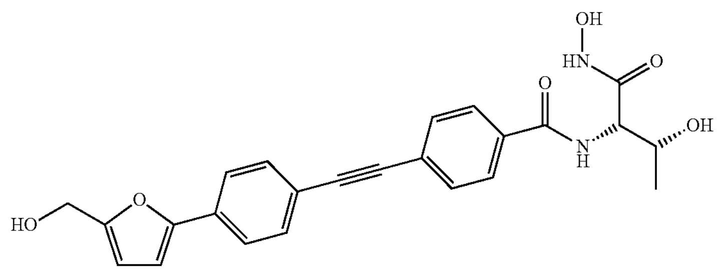 |
| 3 | 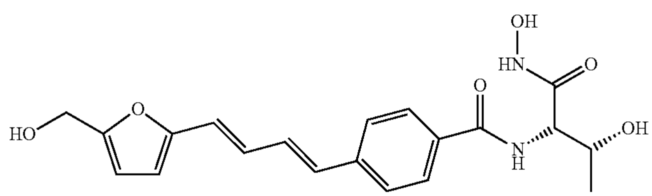 |
| 4 | 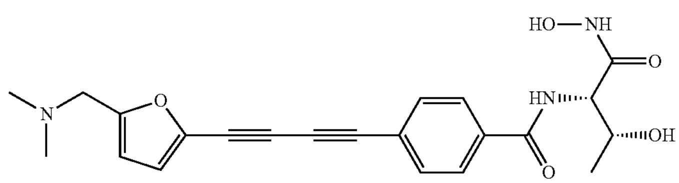 [SMILES: C[C@@H](O)[C@H](NC(=O)c1ccc(C#CC#Cc2ccc(CN(C)C)o2)cc1)C(=O)NO] |
| 5 | 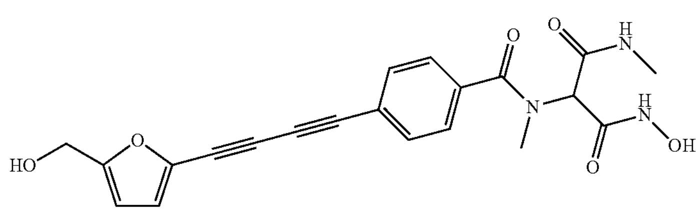 [SMILES: CNC(=O)C(C(=O)NO)N(C)C(=O)c1ccc(C#CC#Cc2ccc(CO)o2)cc1] |
| 6 | 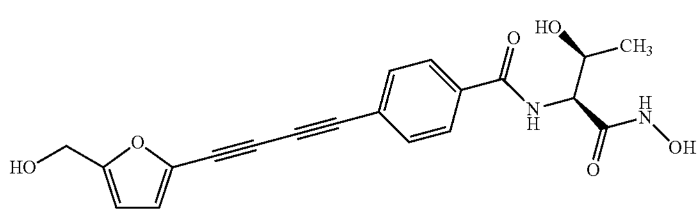 [SMILES: C[C@H](O)[C@H](NC(=O)c1ccc(C#CC#Cc2ccc(CO)o2)cc1)C(=O)NO] |

-continued
| No. | Structure |
|---|---|
| 7 | 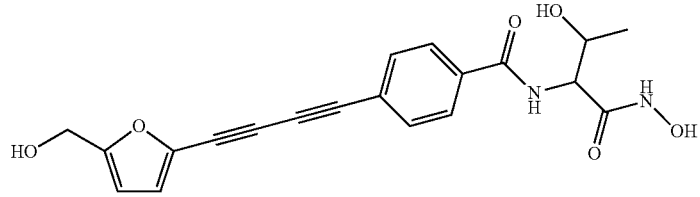 [SMILES: CC(O)C(NC(=O)c1ccc(C#CC#Cc2ccc(CO)o2)cc1)C(=O)NO] |
| 8 | 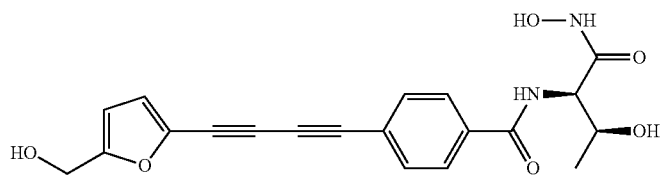 [SMILES: C[C@H](O)[C@@H](NC(=O)c1ccc(C#CC#Cc2ccc(CO)o2)cc1)C(=O)NO] |
| 9 | 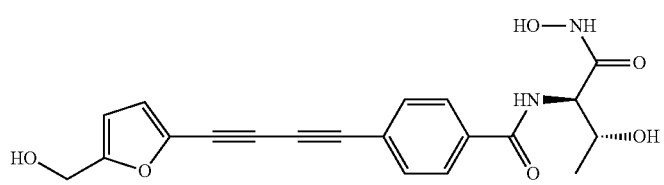 [SMILES: C[C@@H](O)[C@@H](NC(=O)c1ccc(C#CC#Cc2ccc(CO)o2)cc1)C(=O)NO] |
| 10 | 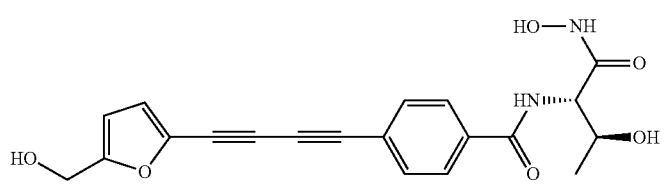 [SMILES: C[C@H](O)[C@H](NC(=O)c1ccc(C#CC#Cc2ccc(CO)o2)cc1)C(=O)NO] |
| 11 | 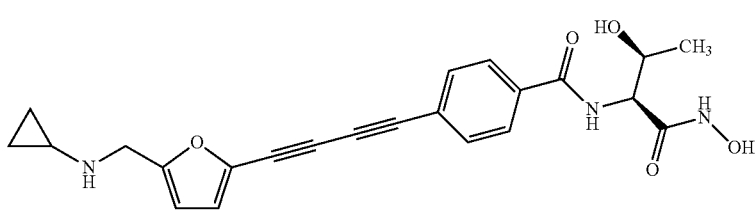 [SMILES: C[C@H](O)[C@H](NC(=O)c1ccc(C#CC#Cc2ccc(CNC3CC3)o2)cc1)C(=O)NO] |
| 12 | 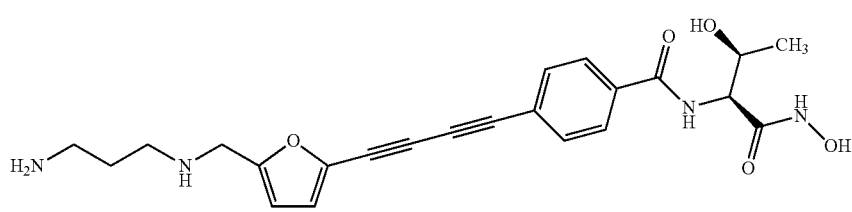 [SMILES: C[C@H](O)[C@H](NC(=O)c1ccc(C#CC#Cc2ccc(CNCCCN)o2)cc1)C(=O)NO] |
| 13 | 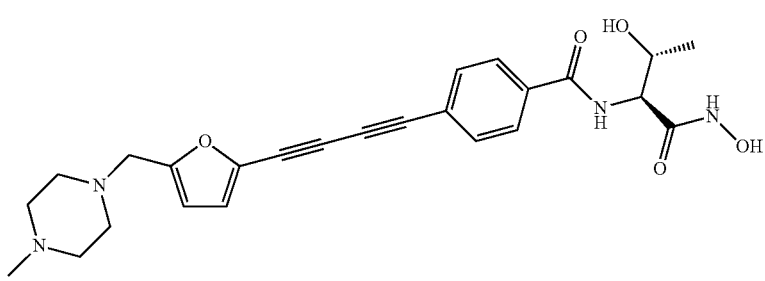 [SMILES: C[C@@H](O)[C@H](NC(=O)c1ccc(C#CC#Cc2ccc(CN3CCN(C)CC3)o2)cc1)C(=O)NO] |

| No. | Structure |
|---|---|
| 14 | 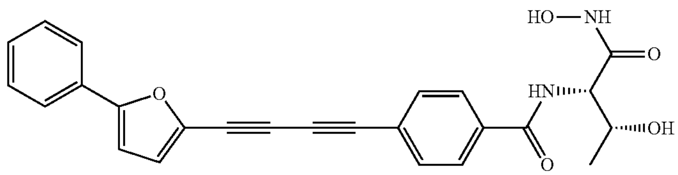 [SMILES: C[C@@H](O)[C@H](NC(=O)c1ccc(C#CC#Cc2ccc(-c3ccccc3)o2)cc1)C(=O)NO] |
| 15 | 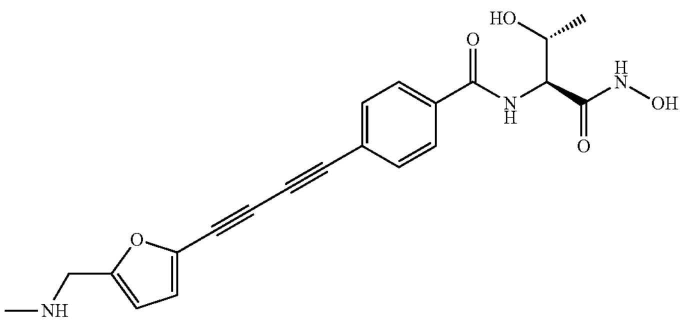 [SMILES: CNCc1ccc(C#CC#Cc2ccc(C(=O)N[C@H](C(=O)NO)[C@@H](C)O)cc2)o1] |
| 16 | 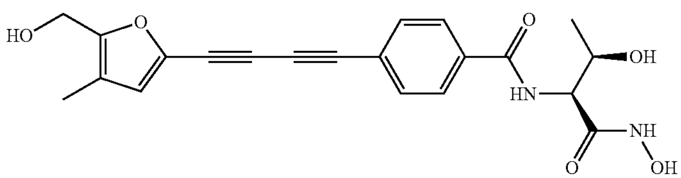 [SMILES: Cc1cc(C#CC#Cc2ccc(C(=O)N[C@H](C(=O)NO)[C@@H](C)O)cc2)oc1CO] |
| 17 | 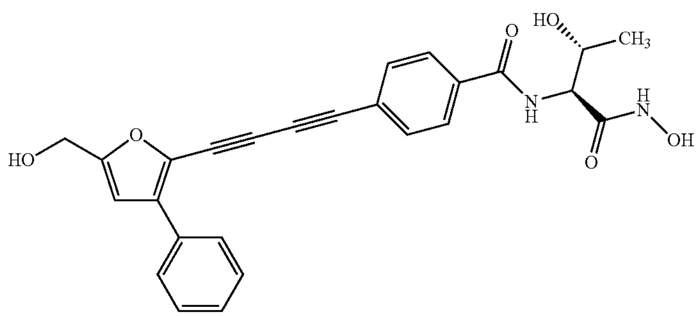 [SMILES: C[C@@H](O)[C@H](NC(=O)c1ccc(C#CC#Cc2oc(CO)cc2-c2ccccc2)cc1)C(=O)NO] |
| 18 | 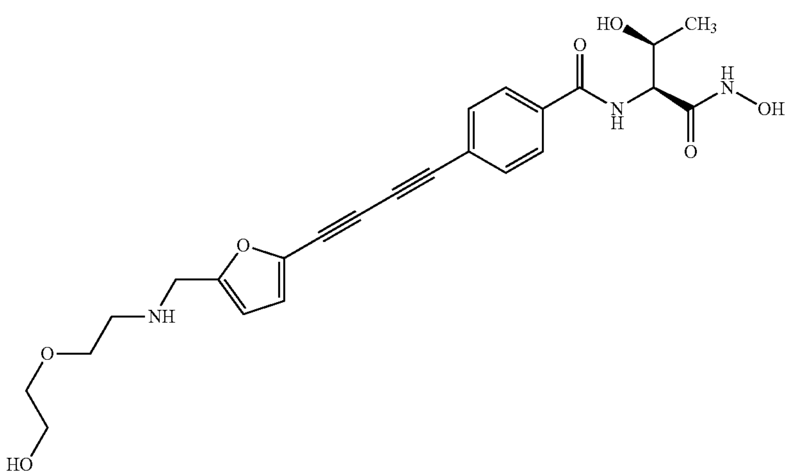 [SMILES: C[C@H](O)[C@H](NC(=O)c1ccc(C#CC#Cc2ccc(CNCCOCCO)o2)cc1)C(=O)NO] |

-continued

| No. | Structure |
|---|---|
| 19 | 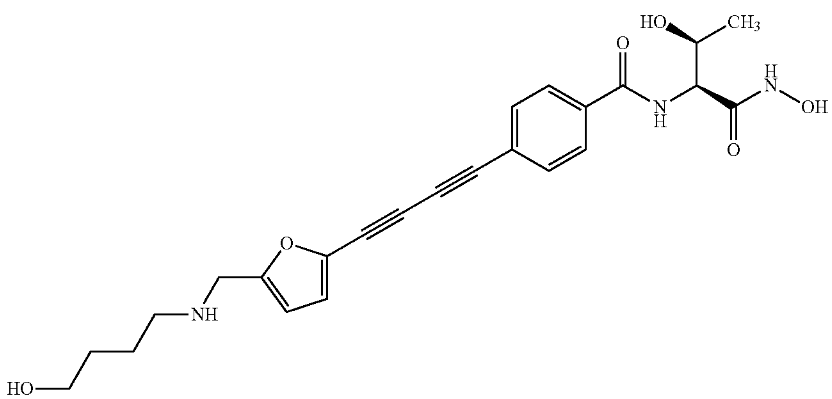 [SMILES: C[C@H](O)[C@H](NC(=O)c1ccc(C#CC#Cc2ccc(CNCCCCO)o2)cc1)C(=O)NO] |
| 20 | 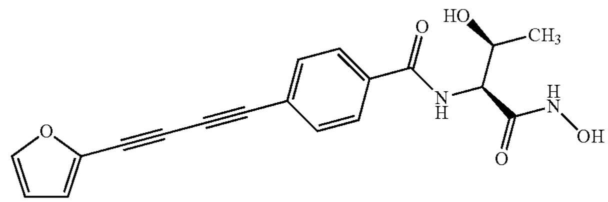 [SMILES: C[C@H](O)[C@H](NC(=O)c1ccc(C#CC#Cc2ccco2)cc1)C(=O)NO] |
| 21 | 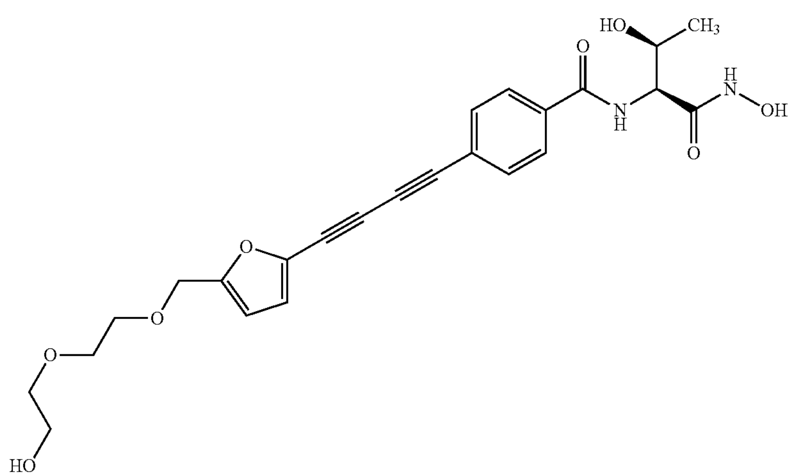 [SMILES: C[C@H](O)[C@H](NC(=O)c1ccc(C#CC#Cc2ccc(COCCOCCO)o2)cc1)C(=O)NO] |
| 22 | 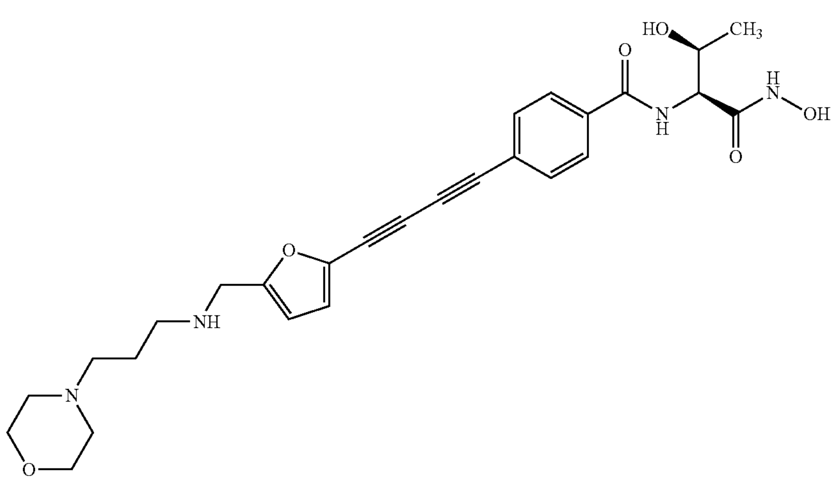 [SMILES: C[C@H](O)[C@H](NC(=O)c1ccc(C#CC#Cc2ccc(CNCCCN3CCOCC3)o2)cc1)C(=O)NO] |

-continued
| No. | Structure |
|---|---|
| 23 | 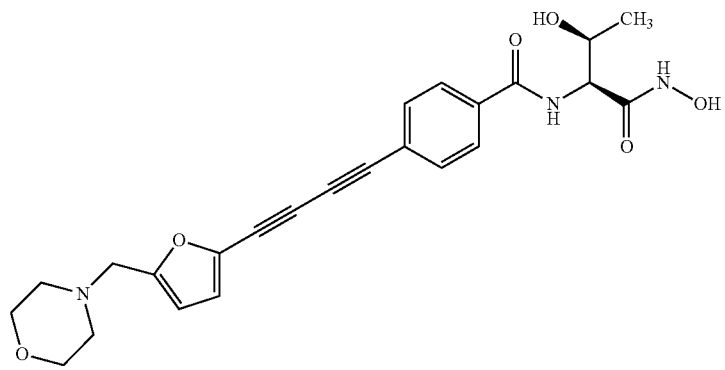 [SMILES: C[C@H](O)[C@H](NC(=O)c1ccc(C#CC#Cc2ccc(CN3CCOCC3)o2)cc1)C(=O)NO] |
| 24 | 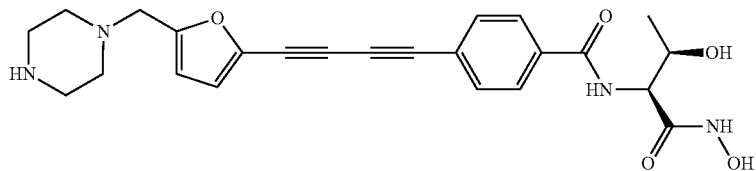 [SMILES: C[C@@H](O)[C@H](NC(=O)c1ccc(C#CC#Cc2ccc(CN3CCNCC3)o2)cc1)C(=O)NO] |
| 25 | 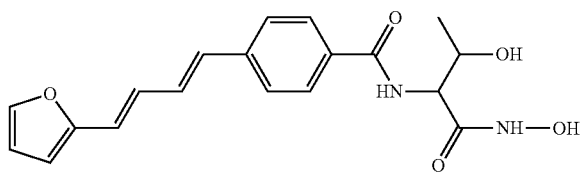 [SMILES: CC(O)C(NC(=O)c1ccc(/C=C/C=C/c2ccco2)cc1)C(=O)NO] |
| 26 | 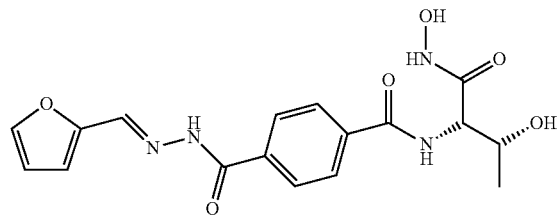 |
| 27 | 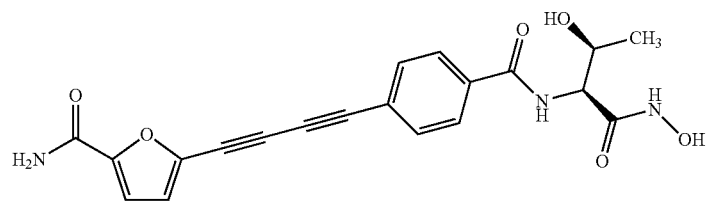 [SMILES: C[C@H](O)[C@H](NC(=O)c1ccc(C#CC#Cc2ccc(C(N)=O)o2)cc1)C(=O)NO] |
| 28 | 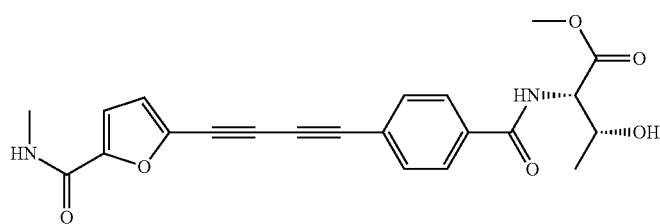 [SMILES: CNC(=O)c1ccc(C#CC#Cc2ccc(C(=O)N[C@H](C(=O)OC)[C@@H](C)O)cc2)o1] |

-continued
| No. | Structure |
|---|---|
| 29 | 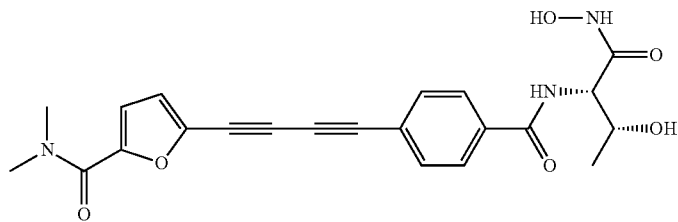 [SMILES: C[C@@H](O)[C@H](NC(=O)c1ccc(C#CC#Cc2ccc(C(=O)N(C)C)o2)cc1)C(=O)NO] |
| 30 | 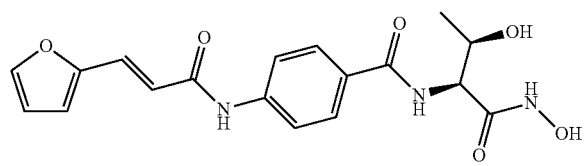 [SMILES: C[C@@H](O)[C@H](NC(=O)c1ccc(NC(=O)/C=C/c2ccco2)cc1)C(=O)NO] |
| 31 | 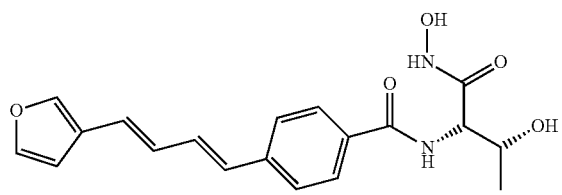 |
| 32 | 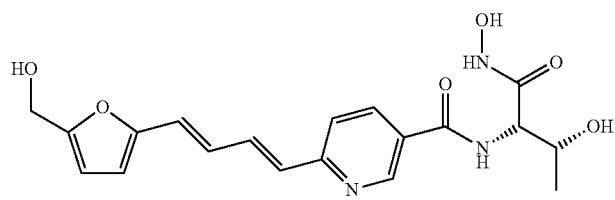 |
| 33 | 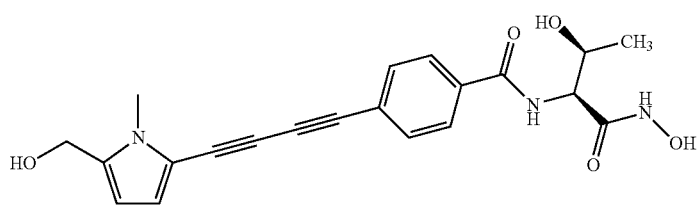 |
| 34 | 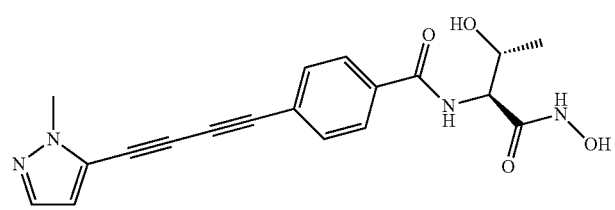 [SMILES: C[C@@H](O)[C@H](NC(=O)c1ccc(C#CC#Cc2ccnn2C)cc1)C(=O)NO] |
| 35 | 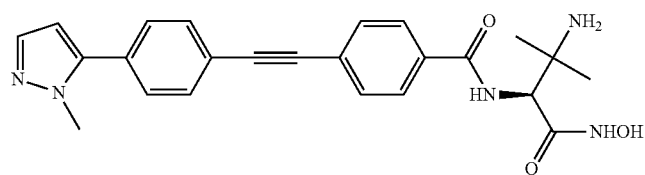 |

-continued
| No. | Structure |
|---|---|
| 36 | 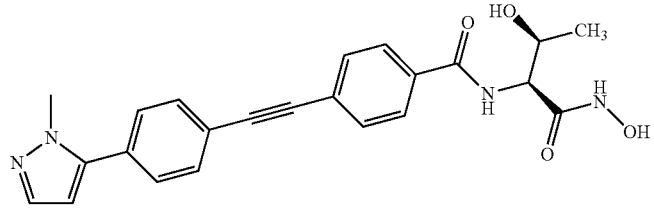 |
| 37 | 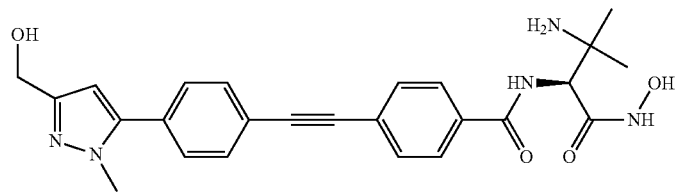 [SMILES: Cn1nc(CO)cc1-c1ccc(C#Cc2ccc(C(=O)N[C@H](C(=O)NO)C(C)(C)N)cc2)cc1] |
| 38 | 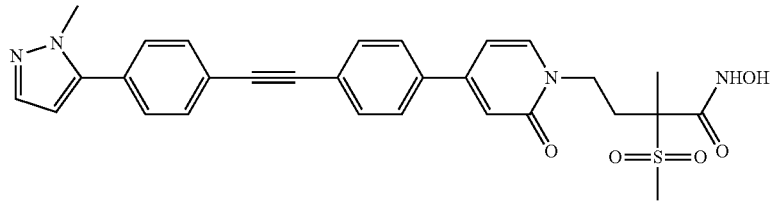 |
| 39 | 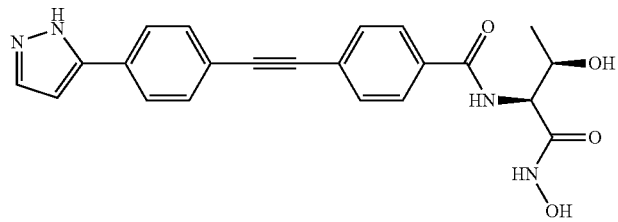 [SMILES: C[C@@H](O)[C@H](NC(=O)c1ccc(C#Cc2ccc(-c3ccn[nH]3)cc2)cc1)C(=O)NO] |
| 40 | 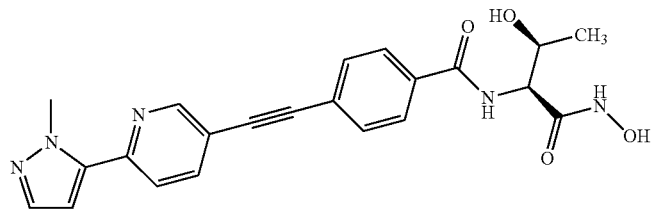 [SMILES: C[C@H](O)[C@H](NC(=O)c1ccc(C#Cc2ccc(-c3ccnn3C)nc2)cc1)C(=O)NO] |
| 41 | 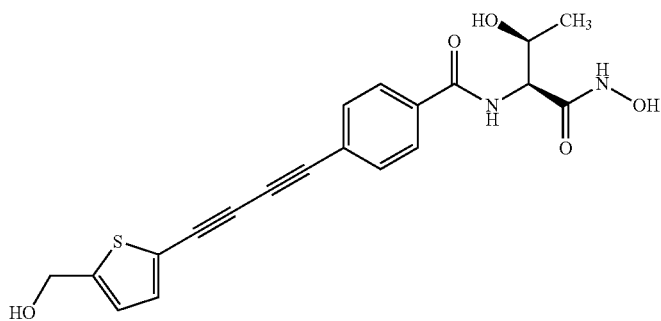 [SMILES: C[C@H](O)[C@H](NC(=O)c1ccc(C#CC#Cc2ccc(CO)s2)cc1)C(=O)NO] |

| No. | Structure |
|---|---|
| 42 | (structure) |
| 43 | (structure) |
| 44 | (structure) |
| 45 | (structure) |
| 46 | (structure) |

| No. | Structure |
|---|---|
| 47 | 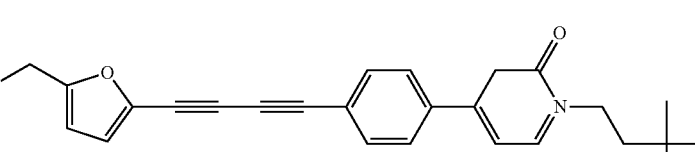 |
| 48 | 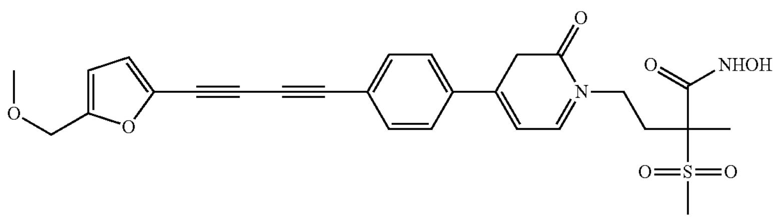 |

"A pharmaceutically acceptable salt" of the compound of the present invention refers to a base addition salt or an acid addition salt formed by the compound of the present invention with a pharmaceutically acceptable, non-toxic base or acid, including organic acid salts, inorganic acid salts, organic base salts, and inorganic base salts. Organic acid salts include formate, acetate, propionate, benzene sulfonate, benzoate, p-toluenesulfonate, 2,3-dihydroxysuccinate, camphorsulfonate, citrate, methanesulfonate, ethanesulfonate, propanesulfonate, fumarate, glyconate, glutamate, hydroxyethyl sulfonate, lactate, maleate, malate, mandelate, mucate, bishydroxylnaphthoate, pantothenate, succinate, tartrate and the like. Specifically preferable are benzoate, benzenesulfonate, p-toluenesulfonate, methanesulfonate, citrate, maleate, fumarate, and tartrate. Inorganic acid salts include hydrochloride, hydrobromide, hydroiodide, sulfate, phosphate, nitrate, and the like. Specifically preferable are hydrochloride, hydrobromide, sulfate, and phosphate. Organic base salts include amine salts, including salts formed with primary, secondary and tertiary amines, cyclic amine and alkali ion exchange resin, which can be selected from a group consisting of salts formed with the following organic bases: for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, meglumine, glucosamine, histidine, hydrabamine, isopropylamine, lysine, methylglucosamine, morpholine, piperazine, piperidine, procaine, purine, theobromine, triethylamine, trimethylamine, tripropylamine and tromethamine and the like. Inorganic base salts include salts formed with ammonia, alkali metals, and alkali earth metals, for example, ammonium salt and lithium salt, sodium salt, potassium salt, calcium salt, magnesium salt, zinc salt, barium salt, aluminum salt, ferric salt, cupric salt, ferrous salt, manganese salt, manganous salt. Specifically preferable are ammonium salt and sodium salt, potassium salt, calcium salt, and magnesium salt.

The term "pharmaceutically acceptable ester" of the compound of the present invention refers to esters of the compound of the present invention that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates, and ethylsuccinates.

The term "prodrug" of the compound of the present invention refers to a compound which, upon administration to a subject, undergoes chemical conversion by metabolic or chemical processes to yield the compound of the present invention and/or a salt and/or solvate thereof. Any compound that will be converted in vivo to provide the bioactive agent (i.e., the compound of the present invention) is a prodrug within the scope and spirit of the invention. For example, compounds containing a carboxy group can form physiologically hydrolyzable esters which serve as prodrugs by being hydrolyzed in the body to yield the compound of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

In addition, the compound of the present invention in free form may be converted into a corresponding compound in the form of a salt, and vice versa. The compound of the present invention in free form or in the form of a salt and/or in the form of a solvate may be converted into a corresponding compound in free form or in the form of a salt in non-solvated form, and vice versa.

A part of the compound of the present invention contains one or more asymmetric centers, and therefore it can be a racemate and a racemic mixture, a single enantiomer, a diastereomeric mixture, and a single diastereomer. The compound of the present invention has asymmetric centers, which each independently generate two optical isomers, respectively. The scope of the present invention encompasses all possible optical isomers and diastereomeric mixture and pure or partially pure compounds. The present invention includes all stereoisomeric forms of these compounds. The present invention encompasses cis-isomer and trans-isomer. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. Individual stereoisomers of compounds of the invention may be prepared synthetically from commercially available starting materials that contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods. In addition, compounds including geometric isomers of carbon-carbon double bonds and carbon-nitrogen double bonds are included in the compound of the present invention. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds of the present invention are encompassed within the scope of the present invention.

The 'solvate' of the compound of the present invention refers to a molecular complex comprising the compound of the invention and a stoichiometric amount of one or more pharmaceutically acceptable solvent molecules, for example, ethanol. The term 'hydrate' is employed when said solvent is water.

The structure described in the present invention also includes the compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention.

The compound of the present invention exhibits the anti-bacterial activity, for example, shows the anti-bacterial activity for the following bacteria: Gram-positive bacteria, Gram-negative bacteria, and the like. The compound of the present invention specifically aims to the bacteria such as Gram-positive bacteria or Gram-negative bacteria to exert an anti-bacterial function and can suppress their growth or destroying them and also can keep down the propagation of bacteria, and kill some of the bacteria to decrease their count. As the examples of gram-positive bacteria, the following can be exemplified: the genus *Staphylococcus* (*Staphylococcus aureus, Staphylococcus epidermidis*, etc.), the genus *Streptococcus* (*Streptococcus pyogenes, Streptococcus agalactiae, Streptococcus pneumoniae*, etc.), and the genus *Enterococcus* (*Enterococcus faecalis, Enterococcus faecium*, etc.). As the examples of gram-negative bacteria, the following can be exemplified: the genus *Pseudomonas* (*Pseudomonas aeruginosa*, etc.), the genus *Escherichia* (*Escherichia coli*, etc.), the genus *Klebsiella* (*Klebsiella pneumoniae, Klebsiella oxytoca*, etc.), the genus *Haemophilus* (*Haemophilus influenzae, Haemophilus parainfluenzae*, etc.), the genus *Bordetella* (*Bordetella pertussis, Bordetella bronchiseptica*, etc.), the genus *Serratia* (*Serratia marcescens*, etc.), the genus *Proteus* (*Proteus mirabilis*, etc.), the genus *Enterobacter* (*Enterobacter cloacae*, etc.), the genus *Campylobacter* (*Campylobacter jejuni*, etc.), the genus *Citrobacter*, the genus *Vibrio* (*Vibrio parahaemolyticus, Vibrio cholerae*, etc.), the genus *Morganella* (*Morganella morganii*, etc.), the genus *Salmonella* (*Salmonella typhi, Salmonella* paratyphi, etc.), the genus *Shigella* (*Shigella dysenteriae*, etc.), the genus *Acinetobacter* (*Acinetobacter baumannii, Acinetobacter calcoaceticus*, etc.), the genus *Legionella* (*Legionella pneumophila*, etc.), the genus *Bacteroides* (*Bacteroides fragilis*, etc.), the genus *Neisseria* (*Neisseria gonorrhoeae, Neisseria meningitides*, etc.), the genus *Moraxella* (*Moraxella catarrhalis*, etc.), the genus *Chlamydia* (*Chlamydia trachomatis, Chlamydia psittaci*, etc.), and the genus *Helicobacter* (*Helicobacter pylori*, etc.).

In another embodiment of the present invention, there is provided a pharmaceutical composition, which contains the compound of the present invention.

In another embodiment of the present invention, there is provided a pharmaceutical composition, which contains the compound of the present invention and one or more pharmaceutically acceptable adjuvants.

The compound of the present invention can be made into a medicinal preparation upon the combination with one or more pharmaceutically acceptable adjuvants. As the pharmaceutically acceptable adjuvant, pharmaceutically acceptable carriers, excipients, diluents, and the like can be used. Examples of such carriers, excipients and diluents include water, lactose, dextrose, fructose, sucrose, sorbitol, mannitol, polyethylene glycol, propylene glycol, and the like. Moreover, the above carriers, excipients or diluents can be mixed, as needed, with commonly used additives such as thickeners, binders, disintegrants, pH regulators, and solvents, and can be prepared as an oral or parenteral drug, such as tablets, pills, capsules, granules, powders, liquids, emulsions, suspensions, ointments, injections, or skin patches, by a customary pharmaceutical technology.

The present invention also provides use of the compound of the present invention, a pharmaceutical composition comprising the compound of the present invention, for the treatment and/or prevention of infectious diseases.

In one aspect of the present invention, there is provided a method of inhibiting a deacetylase enzyme (LpxC) in gram-negative bacteria, thereby affecting bacterial growth, comprising administering the compound of the present invention to a patient in need of such inhibition.

In another aspect of the invention, there is provided a method of inhibiting LpxC, thereby modulating the virulence of a bacterial infection, comprising administering the compound of the present invention to a patient in need of such inhibition.

In some embodiments of the method of inhibiting LpxC using the compound of the present invention, the MIC$_{50}$ value of the compound is less than or equal to 16 g/mL with respect to LpxC. In other such embodiments, the MIC$_{50}$ value is less than or equal to 8 µg/mL, less than or equal to 4 µg/mL, less than or equal to 2 µg/mL, less than or equal to 1 µg/mL, or less than or equal to 0.5 µ/mL.

Additionally, in one aspect of the invention, the method for treating and/or preventing a subject comprises administering to the subject an antibacterially effective amount of the compound of the present invention or a pharmaceutical composition of the present invention. In a preferred embodiment of the method of treatment, the subject is a mammal. In some embodiments, the subject is a human.

In another aspect of the invention, there is provided a method of administering the compound of the present invention to fermentative or non-fermentative gram-negative bacteria. In a preferred embodiment of the method of administering the compound of the present invention to fermentative or non-fermentative gram-negative bacteria, the gram-negative bacteria are selected from the group consisting of *Pseudomonas aeruginosa, Stenotiophomonas maltophila, Burkholderia cepacia, Alcaligenes xylosoxidans, Acinetobacter, Enterobacteriaceae, Haemophilus, Neisseria* species.

In another embodiment of the present invention, there is provided a method of administering an inhibitory amount of the compound of the present invention to gram-negative bacteria, such as Enterobacteriaceae that is selected from the group consisting of organisms such as *Serratia, Proteus, Klebsiella, Enterobacter, Citrobacter, Salmonella, Providencia, Morganella, Cedecea*, and *Edwardsiella* species and *Escherichia coli*. Another embodiment of the present invention provides a pharmaceutical composition comprising the compound of the present invention and at least one other pharmaceutically active ingredient.

In another embodiment of the present invention, there is provided use of a pharmaceutical composition comprising the compound of the present invention and at least one other pharmaceutically active ingredient in the treatment and/or prevention of infectious diseases.

In another embodiment of the present invention, the pharmaceutically active ingredient is another antibacterial agent (hereinafter also referred to as a second antibacterial agent) in addition to the compound of the present invention.

In another embodiment of the present invention, the pharmaceutically active ingredient is a non-antibacterial agent in addition to the compound of the present invention.

The compound of the present invention is useful in combination with other pharmaceutically active ingredients. The compound of the present invention augments the sensitivity of gram-negative bacteria to existing classes of antibacterials. Combinations of the presently disclosed compounds with other anti-bacterial agents are within the scope of the invention. Such anti-bacterial agents include, but are not limited to, Erythromycin, Rifampicin, Nalidixic Acid, Carbenicillin, Bacitracin, Cycloserine, Fosfomycin, Vancomycin, Piperacillin, Amikacin, Ciprofloxacin, Polymyxin, Ceftazidime, and Imipenem.

A further aspect of the invention is the use of LpxC inhibitors for the treatment of an infection, particularly a bacterial infection. A bacterial infection treated with the compound of the present invention can be a primary infection or a co-infection caused by a species of bacteria and one or more additional infectious agents selected from a group consisting of bacteria, viruses, parasites, and fungus.

The term "treating and/or preventing", as used herein, refers to reversing, alleviating, inhibiting the progress of, or preventing the disorder or condition to which such term applies, or one or more symptoms of such disorder or condition.

The compound of the present invention can be used for treating and/or preventing diseases/disorders/conditions caused by the bacterial production of endotoxin and, in particular, by gram-negative bacteria and bacteria that use LpxC in the biosynthesis of lipopolysaccharide (LPS) or endotoxin.

The compound of the invention also is useful in treating and/or preventing the diseases/disorders/conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, the treatment includes the administration of the compound of the present invention, a pharmaceutical composition of the present invention, or a combination of the compound of the present invention, optionally with another pharmaceutical active ingredient, which is a second antibacterial agent or a non-antibacterial agent.

For sepsis, septic shock, systemic inflammation, localized inflammation, chronic obstructive pulmonary disease (COPD), and acute exacerbations of chronic bronchitis (AECB), preferred non-antibacterial agents include antiendotoxins including endotoxin receptor-binding antibodies, endotoxin-binding antibodies, antiCD14-binding protein antibodies antilipopolysaccharide-binding protein antibodies and tyrosine kinase inhibitors.

In the treatment of serious or chronic respiratory tract infections, the compound of the present invention may also be used with non-antibacterial agents administered via inhalation. Preferred non-antibacterial agents used in this treatment include anti-inflammatory steroids, non-steroidal anti-inflammatory agents, bronchodilators, mucolytics, anti-asthma therapeutics, and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, sahneterol, bronchodilators, mucolytics, calfactant, beractant, poractant alfa, surfaxin and pulmozyme (also called dornase alfa). The compound of the present invention can be used, alone or in combination with a second antibacterial agent and/or a non-antibacterial agent for the treatment of a serious or chronic respiratory tract infection including serious lung and nosocomial infections such as those caused by Enterobacteraerogenes, *Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter calcoaceticus, Alcaligenes xylosoxidans, Flavobacterium meningosepticum, Providencia stuartii*, and *Citrobacter freundi*, community lung infections such as those caused by *Haemophilus Influenzae, Legionella* species, *Moraxella catarrhalis, Branhamella catarrhalis, Enterobacter species, Acinetobacter species, Klebsiella species*, and *Proteus* species and infections caused by other bacterial species such as *Neisseria* species, *Shigella* species, *Salmonella* species, *Helicobacter pylori, Vibrionaceae* and *Bordetella* species as well as the infections is caused by *Brucella* species, *Francisella tularensis* and/or *Yersinia Pestis*.

When used to treat and/or prevent the disease caused by gram-negative bacteria, the use of the compound of the present invention can make gram-negative bacteria sensitive to the effect of the second antibacterial agent.

When the compound of the present invention is used in combination with one or more second antibacterial agents, the second antibacterial agents include but are not limited to be selected from a group consisting of:

(1) Macrolides or ketolides such as erythromycin, azithromycin, clarithromycin, and telithromycin;

(2) Beta-lactams including penicillin, cephalosporin, and carbapenems such as carbapenem, imipenem, and meropenem;

(3) Monobacteria such as penicillin, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalothin, cefapirin, cefradine, cefaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam;

(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin, and pazufloxacin;

(5) Antibacterial sulfonamides and antibacterial sulphanilamides, including para-aminobenzoic acid, sulfadiazine, sulfisoxazole, sulfamethoxazole, and sulfathalidine;

(6) Aminoglycosides such as streptomycin, neomycin, kanamycin, paromycin, gentamicin, tobramycin, amikacin, netilmicin, spectinomycin, sisomicin, dibekalin, and isepamicin;

(7) Tetracyclines such as tetracycline, chlortetracycline, demeclocycline, minocycline, oxytetracycline, methacycline, doxycycline;

(8) Rifamycins such as rifampicin (also called rifampin), rifapentine, rifabutin, bezoxazinorifamycin, and rifaximin;

(9) Lincosamides such as lincomycin and clindamycin;

(10) Glycopeptides such as vancomycin and teicoplanin;

(11) Streptogramins such as quinupristin and dalfopristin;

(12) Oxazolidinones such as linezolid;

(13) Polymyxins, polymyxin, and polymyxin E;

(14) Trimethoprim and bacitracin;

(15) Drugs for the treatment of gram-positive bacteria such as linezolid.

The second antibacterial agent may be administered in combination with the compound of the present inventions wherein the second antibacterial agent is administered before, simultaneously, or after the compound of the present invention. When simultaneous administration of a compound of the present invention with a second agent is desired and the route of administration is the same, then the compound of the present invention may be formulated with the second antibacterial agent into the same dosage form. An example of a dosage form containing the compound of the present invention and a second antibacterial agent is a tablet or a capsule.

When used for treating a serious or chronic respiratory tract infection, the compound of the present invention may be used alone or in combination with a second antibacterial agent administered via inhalation. In the case of inhalation, a preferred second antibacterial agent is selected from a group consisting of tobramycin, gentamicin, astreonam, ciprofloxacin, polymyxin B, colistin, azithromycin, and polymyxin E.

The pharmaceutical composition of the present invention can be made into any clinically or pharmaceutically acceptable dosage form of formulation, preferably oral formulation and injection.

The compounds of the present invention can be made into any pharmaceutically acceptable dosage form, which can be administered to a mammal, for example, human, orally, parenterally (intravenously, intramuscularly, subcutaneously or rectally), topically and the like.

When being used for parenteral administration, the compound of the present invention can be formulated into an injection preparation, including sterile solution-based, emulsion-based, dispersion-based or suspension-based formulations, and sterile powder or concentrated solution for injection to be formulated or diluted into solution, dispersion or suspension before use, for intramuscular injection, intravenous injection, intravenous instillation, subcutaneous injection and the like.

The injection preparation can be produced by conventional procedures in the pharmaceutical field, by using aqueous solvents or non-aqueous solvents. The most commonly used aqueous solvent is water for injection, and sodium chloride solution or other suitable aqueous solutions can also be used. Commonly used non-aqueous solvents are vegetable oil, for example, soybean oil for injection, as well as aqueous solutions of ethanol, propylene glycol, polyethylene glycol, etc., and the like. The injection preparation can be formulated without adding additives; or suitable additives, such as osmotic modifier, pH modifier, solubilizer, filler, antioxidant, bacteriostat, emulsifier, suspending agent and the like, can be added according to the property of the drug. Commonly used osmotic modifiers include sodium chloride, glucose, potassium chloride, magnesium chloride, calcium chloride, sorbitol, and the like, preferably sodium chloride or glucose. Commonly used pH modifiers include acetic acid-sodium acetate, lactic acid, citric acid-sodium citrate, sodium bicarbonate-sodium carbonate, and the like. Commonly used solubilizers include Polysorbate 80, propylene glycol, lecithin, polyoxyethylenated castor oil, cyclodextrin and the like. Commonly used fillers include lactose, mannitol, sorbitol, dextran, and the like. Commonly used antioxidants include sodium sulfite, sodium bisulfite, sodium metabisulfite, and the like. Commonly used bacteriostats are phenol, cresol, trichloro-tert-butanol, and the like.

The pharmaceutical composition can also be formulated to dosage forms for rectal or topical administration, including suppository, ointment, cream, patch, powder, spray, inhalant, and the like by conventional methods.

When being used for oral administration, the compound of the present invention can be formulated by conventional methods into conventional solid formulations, such as tablet, capsule, pill, granule and the like; and can be formulated into oral liquid formulations, such as oral solution, oral suspension, syrup and the like. Tablets are predominantly oral compressed tablets and include buccal tablet, sublingual tablet, buccal patch, chewable tablet, dispersible tablet, soluble tablet, effervescent tablet, sustained release tablet, controlled release tablet and enteric coated tablet and the like. Based on the solubility and release properties, capsules can be divided into hard capsule, soft capsule, sustained release capsule, controlled release capsule and enteric coated capsule and the like. Pills include dripping pill, rotula, parvule and the like. Granules can be divided into soluble granule, suspensible granule, effervescent granule, enteric coated granule, sustained release granule and controlled release granule and the like.

In the preparation of oral formulation, suitable filler, binder, disintegrant, lubricant and the like can be added. Commonly used fillers include starch, powdered sugar, calcium phosphate, calcium sulfate dihydrate, dextrin, microcrystalline cellulose, lactose, pre-gelatinized starch, mannitol, and the like. Commonly used binders include sodium carboxymethyl cellulose, PVP-K30, hydroxypropyl cellulose, starch slurry, methylcellulose, ethylcellulose, hydroxypropyl methylcellulose, gelatinized starch, and the like. Commonly used disintegrants include dry starch, crospovidone, crosslinked sodium carboxymethyl cellulose, sodium carboxymethyl starch, low-substituted hydroxypropyl cellulose, and the like. Commonly used lubricants include magnesium stearate, talc powder, sodium dodecylsulfate, micronized silica gel, and the like.

When the compound of the present invention is made into a pharmaceutical composition (e.g., a pharmaceutical preparation), the pharmaceutical composition of the present invention contains 0.01-1000 mg, suitably 0.1-500 mg, preferably 0.1-200 mg, more preferably 1-100 mg, for example, 0.5 mg, 1 mg, 3 mg, 5 mg, 10 mg and 15 mg of the compound of the present invention. The pharmaceutical composition (e.g., the pharmaceutical preparation) of the present invention may be in the form of a unit dose, and the unit dose contains 0.01-1000 mg, suitably 0.1-500 mg, preferably 0.1-200 mg, more preferably 1-100 mg of the compound of the present invention.

On the other hand, the present invention also provides the use of the compound of the present invention in the manufacture of a medicament for treating and/or preventing infectious diseases.

For adult patients, the compound of the present invention can be administered in the above-mentioned dosage form, once a day or divided into several times to give a total amount of 0.001-1500 mg/day, preferably 0.01-1000 mg/day, more preferably 0.1-800 mg/day, particularly preferably 1-600 mg/day, e.g. 250 mg/day, 400 mg/day, 500 mg/day, 600 mg/day. It should be noted that the administration amount of the compound of the present invention can be appropriately increased or decreased according to the type of the disease of the subject to be treated, the patient's age, weight, symptom, and the like.

The compounds of the present invention as antibiotics show good antibacterial activity, good biological stability, especially good antibacterial activity against Gram-negative bacteria, and can be used to treat and/or prevent various diseases caused by Gram-negative bacteria.

EXAMPLES

Hereinafter, the above-mentioned content of the present invention will be further described in detail through specific embodiments in the form of examples. However, it should not be understood that the scope of the above-mentioned subject of the present invention is limited to the following examples. All technologies implemented based on the foregoing content of the present invention belong to the scope of the present invention. First, the beneficial effects of the compounds of the present invention are further explained through the antibacterial activity experiment, but this should not be understood as the compounds of the present invention only have the following beneficial effects.

Experiment 1: In Vitro Antibacterial Activity of the Compounds of the Present Invention Tested strains: all the clinically separated strains below were purchased from public facilities.
*Escherichia coli* ATCC25922, *Pseudomonas aeruginosa* ATCC27853, *Klebsiella pneumoniae* ATCC700603, and the like.

Tested Samples: Imipenem, Ceftazidime: Commercial Products, the Following Experiments were Carried Out According to the Content of an Effective Ingredient in Each Commercial Product;

The compounds of the present invention, their chemical names, and preparation methods are shown in the preparation example of each compound.

Experiment method: Agar dilution method, refer to National Committee for Clinical Laboratory Standards. 2006. Methods for Dilution Antimicrobial Susceptibility Tests for Bacteria That Grow Aerobically; Approved Standard—Seventh Edition M7-A7, Vol 26, No. 2, 2006, to determine the MIC of the compound. MIC represents the minimum inhibitory concentration.

Experiment Result and Conclusion

TABLE 1

Antibacterial activity MIC (μg/mL) of some compounds of the present invention against *Klebsiella pneumoniae*

| Compound No. | $MIC_{50}$ | $MIC_{90}$ |
|---|---|---|
| Compound 4 | 1 | 2 |
| Compound 6 | 1 | 1 |
| Compound 11 | 0.5 | 2 |
| Compound 18 | 2 | 2 |
| Compound 23 | 1 | 1 |
| Compound 33 | 0.5 | 1 |
| Compound 41 | 0.125 | 0.25 |

TABLE 2

Antibacterial activity MIC (μg/mL) of some compounds of the present invention against *Escherichia coli*

| Compound No. | $MIC_{50}$ | $MIC_{90}$ |
|---|---|---|
| Compound 4 | 0.25 | 0.25 |
| Compound 5 | 2 | 4 |
| Compound 6 | 0.125 | 0.125 |
| Compound 11 | 0.125 | 0.25 |
| Compound 22 | 0.5 | 2 |
| Compound 23 | 0.25 | 0.25 |
| Compound 33 | 0.125 | 0.125 |
| Compound 41 | ≤0.03 | 0.06 |

TABLE 3

Antibacterial activity MIC (μg/mL) of some compounds of the present invention against *Pseudomonas aeruginosa*

| Compound No. | MIC (μg/mL) $MIC_{50}$ | $MIC_{90}$ |
|---|---|---|
| Compound 1 | 1 | >16 |
| Compound 3 | 2 | 16 |
| Compound 4 | 1 | 4 |
| Compound 5 | 0.125 | 1 |
| Compound 6 | 0.25 | 1 |
| Compound 10 | 0.125 | 1 |
| Compound 11 | 1 | 8 |
| Compound 12 | 2 | 4 |
| Compound 13 | 2 | 8 |
| Compound 15 | 0.5 | 2 |
| Compound 16 | 0.5 | 2 |
| Compound 17 | 8 | >16 |
| Compound 18 | 1 | 4 |
| Compound 19 | 2 | 8 |
| Compound 20 | 0.25 | 1 |
| Compound 21 | 1 | 4 |
| Compound 22 | 4 | >16 |
| Compound 23 | 1 | 8 |
| Compound 24 | 4 | >16 |
| Compound 25 | 1 | >16 |
| Compound 26 | / | 4 |
| Compound 27 | / | 4 |
| Compound 29 | 1 | 4 |
| Compound 33 | 1 | 8 |

TABLE 3-continued

Antibacterial activity MIC (μg/mL) of some compounds of the present invention against *Pseudomonas aeruginosa*

| Compound No. | MIC (μg/mL) | |
|---|---|---|
| | $MIC_{50}$ | $MIC_{90}$ |
| Compound 34 | 4 | >16 |
| Compound 35 | 2 | 16 |
| Compound 36 | 2 | >16 |
| Compound 37 | 1 | / |
| Compound 40 | 2 | 1 |
| Compound 41 | 0.25 | 1 |
| Compound 42 | 0.5 | 4 |
| Compound 43 | 1 | 4 |
| Compound 45 | 4 | / |
| Compound 46 | 1 | 8 |
| Compound 47 | 4 | >16 |
| Compound 48 | 2 | / |
| Imipenem | 2 | 16 |
| Ceftazidime | 2 | >16 |

The experiment results showed that the compounds of the present invention had excellent antibacterial activities against the tested strains. Specifically, the antibacterial activities of the compounds of the present invention were better than or comparable to those of the control compounds. Therefore, the compounds of the present invention had good clinical application potential.

Experiment 2: Evaluation of In Vitro Antibacterial Effect of the Compounds of the Present Invention on Polymyxin-Resistant Mcr-1 Positive Enterobacteriaceae Tested samples: the compounds of the present invention, prepared according to the methods of the preparation examples;

Polymyxin E sulphate, Ampicillin, Cefotaxime, Gentamicin, Ciprofloxacin, Tetracycline, and Bactrim were all commercial products, the following experiments were carried out according to the content of an effective ingredient in each commercial product.

Tested strains: *Escherichia coli* carrying mcr-1 gene isolated from animals and *Escherichia coli* ATCC25922, a quality control strain, were provided by South China Agricultural University.

Experiment Method

With reference to the agar dilution method in CLSI, the MIC value of the tested drugs to the polymyxin resistant mcr-1 positive *Escherichia coli* were determined.

Preparation of drug-containing agar plates: a drug solution with the highest concentration was prepared for each compound; the drug solution with the highest concentration was subjected to the double dilution; for each of dilution gradient, 1 mL (20×drug working solution) of the drug solution was added to 19 mL MH agar at 45-50° C.; immediately after addition, the agar and the drug solution were uniformly mixed to give a drug-containing agar plate with final concentrations of 64, 32, 16, 8, 4, 2, 1, 0.5, 0.25, 0.125 and 0.06 g/mL, and the plate was solidified for later use; and in the meanwhile, a growth control group was arranged.

Inoculum preparation and culture: the strains stored at −80° C. were rejuvenated and formulated with broth so that the turbidity reached or exceeded 0.5 #McFarland unit; a 96-well plate was used as the inoculation tank, and the bacterial solution was diluted with sodium chloride injection so that the content of bacteria inoculated on the agar was 104 CFU/point. A multi-point inoculation instrument was used to inoculate the bacterial solution to the surface of the labeled drug-containing agar. After the water in the inoculation point was completely absorbed by the agar, the plate was placed upside down in a 37° C. constant-temperature incubator and incubated for 16-20 hours.

Experiment Results:

In this experiment, polymyxin-resistant mcr-1 positive Enterobacteriaceae were evaluated. The in vitro $MIC_{50}$ and $MIC_{90}$ values of each compound were shown in Table 4:

TABLE 4

In vitro antibacterial effects of the compounds of the present invention on polymyxin-resistant mcr-1 positive *Enterobacteriaceae* (unit μg/mL)

| Compound No. | $MIC_{50}$ Value | $MIC_{90}$ Value |
|---|---|---|
| Compound 5 | 0.5 | 1 |
| Compound 6 | 0.125 | 0.5 |
| Polymyxin E sulphate | 16 | 32 |
| Ampicillin | >128 | >128 |
| Cefotaxime | 2 | 128 |
| Gentamicin | 4 | 64 |
| Ciprofloxacin | 4 | 32 |
| Tetracycline | 32 | 64 |
| Imipenem | 0.125 | 4 |
| Bactrim | 32 | 32 |

Experiment Conclusion

It could be seen from Table 4 that Compound 5 and Compound 6 of the present invention had good in vitro antibacterial activity against polymyxin E sulfate resistant mcr-1 positive Enterobacteriaceae. The $MIC_{50}$ values were 0.125 μg/mL and 0.5 μg/mL respectively, and the $MIC_{90}$ values were 0.5 μg/mL and 1 g/mL respectively, which were superior to those of the listed drugs Ampicillin, Cefotaxime, Gentamicin, Ciprofloxacin, Tetracycline, Imipenem and Bactrim (≥4: drug resistance). This showed that the compounds of the present invention had good clinical application potential compared with the existing compounds.

Experiment 3: Evaluation of In Vitro Antibacterial Activity of the Compounds of the Present Invention Against *Pseudomonas aeruinosa*

Tested samples: the compound of the present invention, prepared according to the preparation example method; Compound C, prepared with reference to WO2008154642A2.

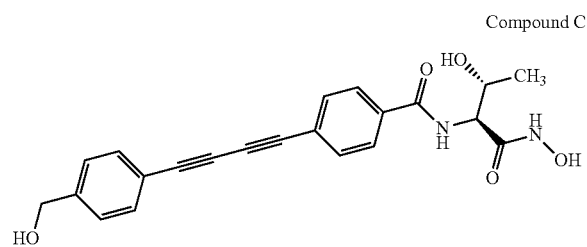 [SMILES: C[C@@H](O)[C@H](NC(=O)c1ccc(C#CC#Cc2ccc(CO)cc2)cc1)C(=O)NO]

Compound C

Experiment Method:

With reference to the steps of the agar dilution method in the 2018 USA Clinical and Laboratory Standards Institute (CLSI), the determination of the minimum inhibitory concentration (MIC) of the compounds against the strain(s) was carried out.

Preparation of drug-containing plate: (1) a drug solution with the highest concentration was prepared, and the highest concentration of each compound was 160 μg/mL. (2) For each compound, the drug solution with the highest concentration was subjected to the double dilution, and a total of 10 concentration gradients was obtained; for each of dilution gradient, 2 mL of the drug solution was added to 18 mL MH agar solution which had been autoclaved at 121° C. and cooled to about 50° C.; the mixture was uniformly mixed, left stand and cooled to give a drug-containing plate; and the plate was labeled. The final concentrations of the compound were respectively 16, 8, 4, 2, 1, 0.5, 0.25, 0.125, 0.06 and 0.03 μg/mL.

Inoculum preparation and inoculation: A fresh single colony was selected, diluted with 0.9% sodium chloride injection, adjusted to 0.5 #McFarland turbidity, and then diluted 10 times with 0.9% sodium chloride injection, then inoculated with an automatic multi-point inoculation instrument to the labeled drug-containing plate.

Experiment Results:

In this experiment, the in vitro antibacterial activities of Compound 6 and control compound C against *Pseudomonas aeruginosa* were evaluated. The $MIC_{50}$ and $MIC_{90}$ values were shown in Table 5.

Experiment 5: In Vitro Antibacterial Activity of the Compounds of the Present Invention Against *Pseudomonas aeruginosa*

| Compound No. | MIC50 (μg/mL) | MIC90 (μg/mL) |
| --- | --- | --- |
| Compound 6 | 0.5 | 1 |
| Compound C | 4 | >16 |

Experiment Conclusion

It could be seen from Table 5 that Compound 6 of the present invention had good in vitro antibacterial activity against *Pseudomonas aeruginosa*, and the $MIC_{50}$ and $MIC_{90}$ values were 0.5 μg/mL and 1 g/mL respectively; on the contrary, Compound C had poor in vitro antibacterial activity against *Pseudomonas aeruginosa*, the $MIC_{50}$ and $MIC_{90}$ values were 4 μg/mL and >16 μg/mL respectively. In sum, the compounds of the present invention had better antibacterial activity against *Pseudomonas aeruginosa* than Compound C.

Experiment 4: Pharmacokinetics (PK) Determination

1. Experiment Design

| Animal number | Sex | Administration route | Blood collection time points | Biological sample type |
| --- | --- | --- | --- | --- |
| 3 | Male | Intragastric administration (PO) | 0 min, 10 min, 30 min, 1 h, 2 h, 4 h, 6 h, 8 h, 24 h | Plasma |
| 3 | Male | Intravenous injection (IV) | 0 min, 5 min, 15 min, 30 min, 1 h, 2 h, 4 h, 6 h, 8 h, 24 h | |

2. Tested Samples:

The compound of the present invention, self-prepared and dissolved in a suitable solvent.

3. Equipment

Instrument and equipment: API4000 LC-MS/MS

Chromatographic column: Waters XBridge $C_{18}$(2.1×50 mm, 5 m)

4. Blood Collection

Rat blood collection: Animals were fixed. The animal's tail was heated with a water bathtub 10 minutes before each time point. About 200 μL of the blood was collected through the caudal vein. After the blood collection, the blood was placed in an anticoagulation tube containing heparin sodium. The blood samples were centrifuged at 8000 rpm for 6 minutes at 4° C. to obtain plasma samples. The plasma must be prepared within 30 minutes after the blood collection. The plasma was stored in a refrigerator at −80° C. before the test.

5. Experiment Method (1) Test samples were removed from the refrigerator (−80° C.), naturally thawed at room temperature, and then vortexed for 5 minutes;

(2) 20 μL sample was precisely pipetted to a 1.5 mL centrifuge tube;

(3) 200 μL of the internal standard solution was added;

(4) The mixture was vortexed for 5 minutes and centrifuged for 5 minutes (12000 revolutions per minute);

(5) 100 μL of the supernate was precisely pipetted, 100 μL of water was added, the mixture was vortexed for 5 minutes, and the sample was sent to LC-MS/MS for analysis.

6. Data processing method

The results of the concentrations of the test samples (plasma samples) were output with Analyst 1.6.1 of AB Corporation. The meaning value, the standard deviation, the coefficient of variation, and other parameters (not necessary to calculate the parameter that can be directly output from Analyst 1.6.1) were calculated with Microsoft Excel, and the PK parameter is calculated with Pharsight Phoenix 6.1 software.

Experiment Results:

TABLE 6

PK results of the compounds of the present invention in SD rats (IV 2 mg/kg)

| Compound No. | λ_z (1/h) | $t_{1/2z}$ (h) | $AUC_{last}$ (h*ng/ml) | AUCINF_obs (h*ng/ml) | Cl_obs (L/h/kg) | Vz_obs (L/kg) |
| --- | --- | --- | --- | --- | --- | --- |
| Compound 4 | 3.16 ± 1.28 | 0.25 ± 0.12 | 414 ± 10.3 | 417 ± 9.68 | 4.80 ± 0.11 | 1.74 ± 0.81 |
| Compound 5 | 0.99 ± 0.15 | 0.71 ± 0.11 | 8108 ± 1054 | 8153 ± 1045 | 0.62 ± 0.08 | 0.63 ± 0.02 |

TABLE 6-continued

PK results of the compounds of the present invention in SD rats (IV 2 mg/kg)

| Compound No. | λ_z (1/h) | $t_{1/2z}$ (h) | $AUC_{last}$ (h*ng/ml) | AUCINF_obs (h*ng/ml) | Cl_obs (L/h/kg) | Vz_obs (L/kg) |
|---|---|---|---|---|---|---|
| Compound 6 | 1.14 ± 0.21 | 0.62 ± 0.12 | 3999 ± 442 | 4007 ± 443 | 0.50 ± 0.06 | 0.46 ± 0.14 |
| Compound 10 | 0.97 ± 0.23 | 0.74 ± 0.16 | 4891 ± 533 | 4902 ± 532 | 1.03 ± 0.11 | 1.03 ± 0.11 |
| Compound 13 | 1.98 ± 0.04 | 0.35 ± 0.01 | 485 ± 87.4 | 493 ± 87.9 | 4.14 ± 0.70 | 2.09 ± 0.39 |
| Compound 15 | 0.99 ± 0.29 | 0.74 ± 0.22 | 1330 ± 108 | 1351 ± 222 | 1.51 ± 0.27 | 1.57 ± 0.28 |
| Compound 16 | 1.67 ± 0.58 | 0.45 ± 0.14 | 2777 ± 130 | 2786 ± 136 | 0.72 ± 0.04 | 0.47 ± 0.16 |
| Compound 20 | 1.70 ± 0.03 | 0.41 ± 0.01 | 778 ± 116 | 791 ± 117 | 6.41 ± 0.96 | 3.77 ± 0.53 |
| Compound 21 | 4.38 ± 0.25 | 0.16 ± 0.01 | 1403 ± 256 | 1417 ± 255 | 1.45 ± 0.29 | 0.33 ± 0.07 |
| Compound 23 | 3.47 ± 1.09 | 0.21 ± 0.06 | 1157 ± 278 | 1159 ± 277 | 1.80 ± 0.50 | 0.52 ± 0.02 |
| Compound 32 | 1.48 ± 0.46 | 0.506 ± 0.18 | 344 ± 33.7 | 347 ± 32.7 | 5.80 ± 0.53 | 4.24 ± 1.65 |
| Compound 33 | 2.75 ± 0.50 | 0.26 ± 0.04 | 666 ± 318 | 671 ± 315 | 3.39 ± 1.34 | 1.21 ± 0.34 |
| Compound 37 | 0.28 ± 0.08 | 2.63 ± 0.76 | 402 ± 21.6 | 426 ± 28.5 | 4.71 ± 0.33 | 17.6 ± 4.22 |
| Compound 38 | 0.56 ± 0.04 | 1.25 ± 0.09 | 1945 ± 168 | 1991 ± 176 | 1.01 ± 0.09 | 1.81 ± 0.17 |
| Compound 41 | 2.21 ± 0.29 | 0.32 ± 0.04 | 1589 ± 447 | 1594 ± 446 | 1.32 ± 0.33 | 0.61 ± 0.20 |
| Compound 42 | 2.35 ± 0.07 | 0.30 ± 0.01 | 396 ± 41 | 398 ± 41 | 5.06 ± 0.55 | 2.16 ± 0.30 |
| Compound 43 | 2.48 ± 0.06 | 0.28 ± 0.01 | 919 ± 100 | 921 ± 100 | 2.19 ± 0.22 | 0.88 ± 0.07 |

Conclusion: The experiment result showed that the compounds of the present invention had excellent in vivo metabolic stability, which indicated that the compounds of the present invention had good drug potential. Therefore, the compounds of the present invention had excellent clinical application prospects.

The abbreviations and English expressions in the examples have the following meanings:

| TCL | Thin layer chromatography |
|---|---|
| Bu | Butyl |
| Et | Ethyl |
| Me | Methyl |
| EDCI | 1-ethyl-3-(3-dimethylaminopropyl)carbodiimide |
| Hexane | Hexane |
| THF | Tetrahydrofuran |
| DMF | Dimethylformamide |
| EA | Ethyl acetate |
| PE | Petroleum ether |
| DIEA | N,N-diisopropylethylamine |
| DCM | Dichloromethane |
| NBS | N-bromosuccinimide |
| TMS | Trimethylsilyl |
| Boc | Tert-butoxycarbonyl |
| TFA | Trifluoroacetic acid |
| HOBt | Hydroxybenzotriazole |
| HATU | O-(7-azabenzotriazol-1-yl)-N,N,N',N'-tetramethylurea |
| NH$_2$OTHP | O-(tetrahydro-2H-pyran-2-yl)hydroxylamine |
| DMDMA | N,N-dimethylformamide dimethylacetal |
| Pd(dppf)Cl$_2$ | [1,1'-bis(diphenylphosphino)ferrocene]palladium(II) dichloride |

Example 1: Preparation of 4-((1E,3E)-4-(furan-2-yl)buta-1,3-dienyl)-N-((2S,3R)-3-hydroxy-1-(hydroxyamino)-1-oxobutan-2-yl)benzamide (Compound 1)

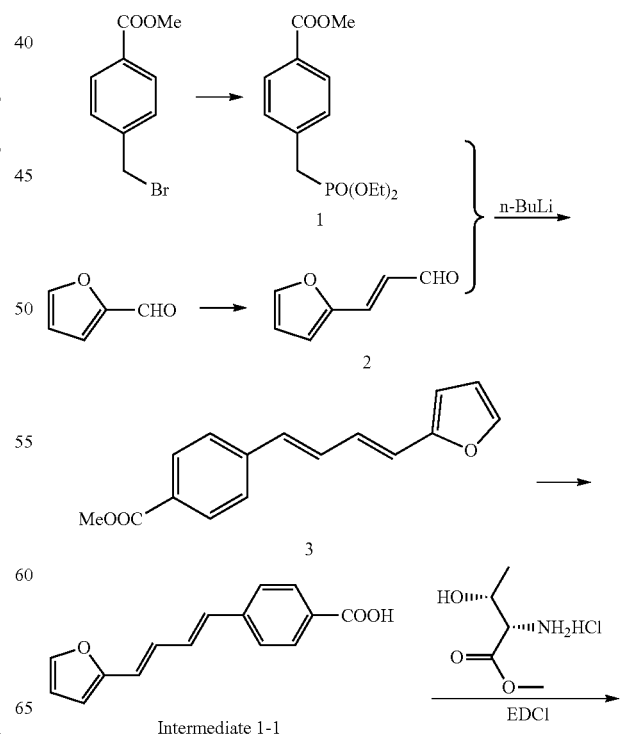

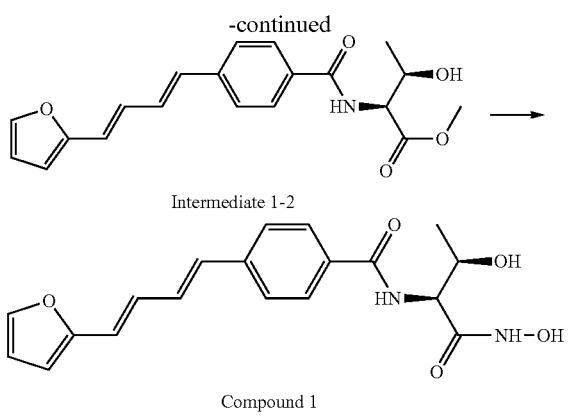

Intermediate 1-2

Compound 1

(1) Preparation of Intermediate 1

To a 250 mL three-neck flask methyl para-bromomethyl-benzoate (50 g, 0.22 mol) and triethyl phosphite (73 g, 0.45 mol) were added. The mixture was warmed in a gradient manner and reacted under reflux. The reaction was carried out in the nitrogen protection. TLC detection showed the reaction starting materials disappeared (developing solvent: EA:PET=1:10). Post-treatment: in the nitrogen protection, the mixture was cooled to room temperature, and concentrated to remove most of the remaining triethyl phosphite in vacuum; toluene (100 mL) was added and the concentration was continued; and the concentration was repeated for three times to dryness to give a pale-yellow oily substance (68 g, higher than the theoretical amount), which was directly used in the following reaction.

(2) Preparation of Intermediate 2

To a 5.0 L three-neck flask furan-carbaldehyde (150 g, 1.56 mol) and ethanol (900 mL) were added. The mixture was cooled in an ice-water bath to 10° C. or lower. A solution of sodium hydroxide (40 g, 1.0 mol) dissolved in the purified water (1.8 L) was added dropwise. After stirring the mixture, an aqueous acetaldehyde solution (400 g, 3.6 mol, 40% of the aqueous solution) was added dropwisely. In the course of the dropwise addition, the system was maintained at a temperature of about 0° C. The dropwise addition was completed over about 5 hours. After an aqueous acetaldehyde solution was added dropwisely, the mixture was naturally warmed to room temperature and reacted overnight. Post-treatment: methyltert-butylether (2 L) was added to the reaction system. The resulting mixture was stirred to separate an organic phase. The organic phase was washed once with brine and concentrated to give a brown oily substance. By directly adding petroleum ether together with silica gel, the purification with column chromatography using petroleum ether as eluent was carried out and the pure product was collected to give an oily substance (56 g), which was directly used in the next step.

(3) Preparation of Intermediate 3

In the nitrogen protection, Intermediate 1 (56 g, 0.196 mol) was dissolved in dry THF (560 mL). The mixture was cooled in a liquid nitrogen ethanol system to an inner temperature of −70° C. or less. An n-butyl lithium solution (81 mL, 2.5M in hexane) was added dropwisely. After the dropwise addition, the mixture was reacted for 30 minutes while maintaining the temperature. Intermediate 2 (22.6 g, 0.185 mol) was dissolved in dry THF (100 mL), and added dropwisely to the above solution while controlling the temperature to less than −70° C. After the dropwise addition, the mixture was reacted for 2 hours while maintaining the temperature and naturally warmed to room temperature. Post-treatment: The reaction system was slowly added to iced water (400 mL). The mixture was stirred and an organic phase was separated off. The aqueous phase was extracted twice with ethyl acetate. The organic phases were combined, washed twice with brine, dried over anhydrous sodium sulphate, and concentrated quickly to dryness. Methyltert-butyl was added. The mixture was pulpified overnight, and filtered to give a yellow solid (wet weight: 30 g). The solid was added to THF (150 mL). The mixture was warmed up to 50° C. and dissolved to give a yellow clear solution, hot filtered, and cooled. A solid was separated. The mixture was filtered to give a yellow bulk solid and dried in vacuum to give Intermediate 3 (26 g), which was directly used in the next step of the reaction.

(4) Preparation of Intermediate 1-1

Intermediate 3 (26 g, crude) was added to THF (260 mL). The mixture was added to a solution of sodium hydroxide (12 g) dissolved in the purified water (130 mL), warmed up to 45-50° C., and reacted overnight. On the next day, TLC indicated still a small amount of the starting materials did not completely react. The reaction mixture was cooled to room temperature, and filtered to give a yellow solid. The solid was added to a mixed solution of THF (150 mL) and ethyl acetate (150 mL). A hydrochloric acid solution (1N) was added dropwisely until the pH of the reaction system was about 1.0. The organic phase was separated, washed once with brine, dried over anhydrous sodium sulphate, and concentrated to give a crude product. The crude product was added to methyltert-butyl ether, and the mixture was pulpified for 2 hours, filtered, and dried in vacuum to give a solid Intermediate 1-1 (15 g).

(5) Preparation of Intermediate 1-2

Intermediate 1-1 (961 mg, 4 mmol) and L-threonine methyl ester hydrochloride (678 mg, 4 mmol) were dissolved in DMF (8 mL). DIEA (1.034 g, 8 mmol) was added. The resulting solution was stirred for 50 minutes. After the solution became clear, HOBt (541 mg, 4 mmol) and EDCI (767 mg, 4 mmol) were added. The mixture was reacted under stirring for 15 hours. In the post-treatment, the reaction system was poured into water. The mixture was filtered by suction. The filter cake was washed with water and dried to give a crude product Intermediate 1-3 (600 mg).

(6) Preparation of Compound 1

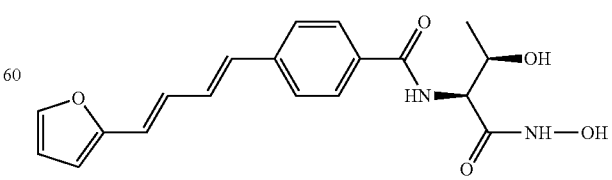

The crude product Intermediate 1-3 (270 mg) was dissolved in methanol (3 mL). An aqueous hydroxylamine solution (1 mL, 50%) was added. The mixture was reacted under stirring for 40 hours. In the post-treatment, the reaction system was poured into water. The mixture was filtered by suction. The filter cake was washed with water and dried to give a product Compound 1 (79 mg).

Molecular Formula: $C_{19}H_{20}N_2O_5$; Molecular Weight: 356.37; Mass Spectrum: (M+H): 357.1

$^1$H-NMR (d-DMSO, 800 MHz) δ 10.66 (1H, s), 8.82 (1H, s), 7.98 (1H, d), 7.87 (2H, d), 7.69 (1H, s), 7.58 (2H, d), 7.23-7.16 (1H, m), 6.89-6.76 (2H, m), 6.69-6.66 (1H, m), 6.56 (2H, d), 5.1-4.8 (1H, m), 4.27 (1H, s), 4.03 (1H, s), 1.08 (3H, d).

With reference to the above Example, Compound 25 was synthesized by using a racemic threonine methyl ester hydrochloride.

Example 2: Preparation of N-((2S,3R)-3-hydroxy-1-(hydroxyamino)-1-oxobutan-2-yl)-4-((4-(5-(hydroxymethyl)furan-2-yl)phenyl)ethynyl)benzamide (Compound 2)

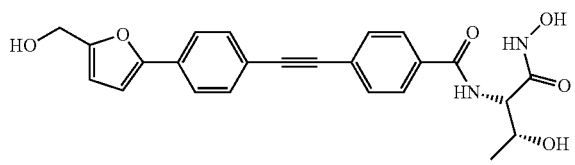

With reference to Example 1, Compound 2 was synthesized.

Molecular Formula: $C_{24}H_{22}N_2O_6$; Molecular Weight: 434.44; Mass Spectrum: (M+): 434.15

$^1$H-NMR (d-DMSO, 800 MHz) δ 10.68 (1H, s), 8.87 (1H, s), 7.96 (2H, d), 7.75 (2H, d), 7.67 (2H, d), 7.63 (2H, d), 7.73 (2H, d), 6.45 (1H, d), 5.33 (1H, t), 4.92 (1H, brs), 4.47 (2H, d), 4.28-4.25 (1H, m), 4.03-4.01 (1H, m), 1.10 (3H, d).

Example 3: Preparation of N-((2S,3R)-3-hydroxy-1-(hydroxamino)-1-oxobutan-2-yl)-4-((1E,3E)-4-(5-(hydroxymethyl)furan-2-yl)buta-1,3-dienyl)benzamide (Compound 3)

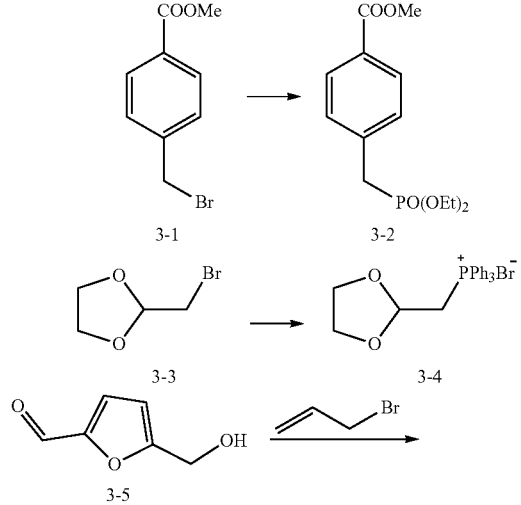

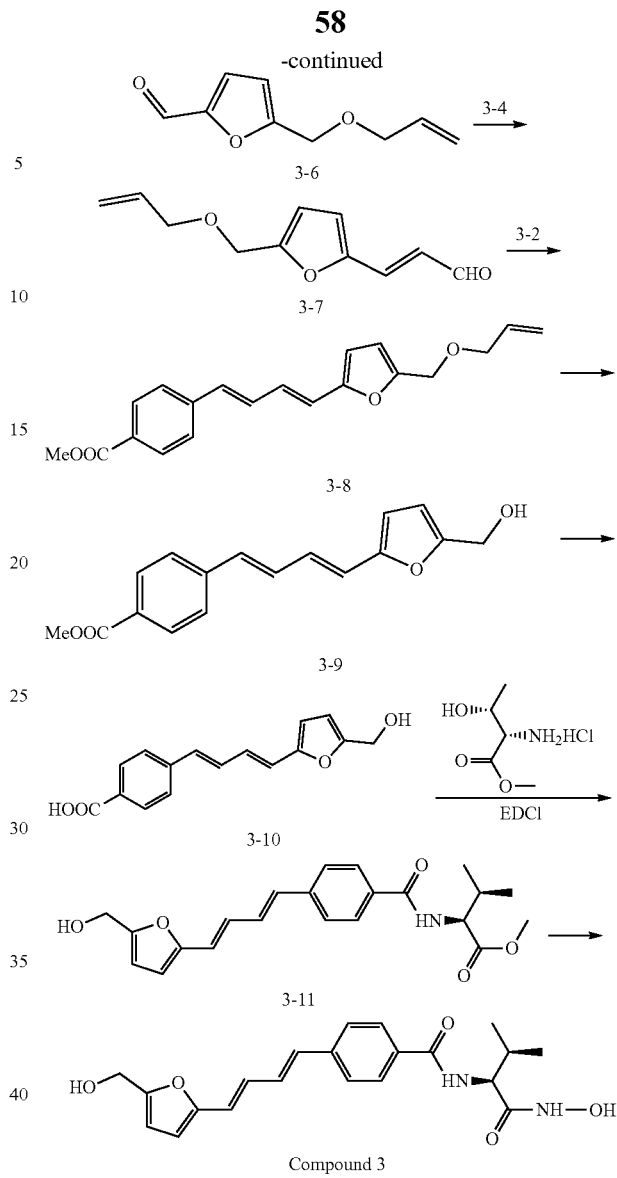

(1) Preparation of Intermediate 3-2

To a 250 mL three-neck flask methyl para-bromomethyl-benzoate (60 g, 0.26 mol, 1.0 eq.) and triethyl phosphite (87 g, 0.52 mol, 2.0 eq.) were added. The mixture was warmed in a gradient manner and reacted under reflux. The reaction was carried out in the nitrogen protection. TLC detection was carried out until the starting material 1 disappeared. In the nitrogen protection, the mixture was cooled to room temperature, and concentrated to remove most of the remaining triethyl phosphite in vacuum; toluene (100 mL) was added and the concentration was continued; the concentration was repeated for three times to dryness to give a pale-yellow oily substance (78 g). The oily substance Intermediate 3-2 was directly used in the next reaction.

(2) Preparation of Intermediate 3-4

To a 2 L three-neck flask toluene (1 L) was added. The starting material 3-3 (156 g, 0.93 mol, 1.0 eq.) was added. The mixture was heated and reacted under reflux for two days. The reaction was terminated and cooled to room temperature. The reaction system was filtered. The solid was washed with methyltert-butyl ether and dried to give a solid Intermediate 3-4 (172 g) in a yield of 33%, which was directly used in the next reaction.

(3) Preparation of Intermediate 3-6

In the nitrogen protection, the starting material 3-5 (185 g, 1.49 mol, 1.0 eq.) was dissolved in dry acetonitrile (560 mL). A powdery sodium hydroxide (56 g, 0.196 mol, 1.05 eq.) was added. The mixture was cooled in a water bath. 3-bromopropylene (450 g, 3.74 mol, 2.5 eq.) was added dropwisely to the reaction system. After the completion of the dropwise addition, the mixture was reacted under stirring at room temperature. TLC (EA/PE~1:5) indicated the completion of the reaction, and the reaction was terminated. The reaction system was poured into water (1 L) to quench the reaction. The reaction system was extracted with methyltert-butyl ether (300 mL*3), washed with water (300 mL*2), washed with brine (300 mL*1), dried, concentrated, and purified by chromatographic column to give the Intermediate 3-6 (16.8 g), which was directly used in the next step.

(4) Preparation of Intermediate 3-7

To DMF (90 mL) the Intermediate 3-6 (14.8 g, 90.1 mmol, 1.0 eq.) and the Intermediate 3-4 (58.0 g, 135.2 mmol, 1.5 eq.) were added. The mixture was stirred at room temperature. Sodium methoxide (14.6 g, 270.4 mmol, 3.0 eq.) dissolved in methanol (45 mL) was added dropwisely to the reaction system, and the temperature of the reaction system increased. After the completion of the dropwise addition, the mixture was reacted at room temperature overnight. TLC (EA/PE-1:5) indicated the completion of the reaction, and the reaction was terminated. The reaction system was poured into water (200 mL) to quench the reaction. The reaction mixture was extracted with ethyl acetate (100 mL*3), washed with water (100 mL*2), washed with brine (100 mL*1), dried, and concentrated to give a brown solid-oil mixture.

The mixture was dissolved in tetrahydrofuran (75 mL). Water (75 mL) and a concentrated hydrochloric acid (35 mL) were added. The mixture was reacted at room temperature for 1 hour. The reaction was terminated. Water (200 mL) was added to quench the reaction system. The reaction mixture was extracted with ethyl acetate (100 mL*3), washed with water (100 mL*2), washed with brine (100 mL*1), dried, and concentrated to give a brown solid-oil mixture. Methyltert-butyl ether (100 mL) was added and the mixture was stirred for 0.5 hours. The solid was removed by filtration, and the mother liquor was concentrated, purified by chromatographic column to give Intermediate 3-7 (12.5 g), which was directly used in the next step.

(5) Preparation of Intermediate 3-8

Intermediate 3-2 (19.3 g, 65.1 mmol, 1.2 eq) was added to tetrahydrofuran (200 mL). In the nitrogen protection, the mixture was cooled to a temperature of between −70° C. and −80° C. n-Butyl lithium (27.0 mL, 65.1 mmol, 1.2 eq) was dropwisely added. The mixture was reacted at a temperature between −70° C. and −80° C. for 30 minutes. Intermediate 3-7 (10.8 g, 56.2 mmol, 1.0 eq) dissolved in tetrahydrofuran (50 mL) was dropwisely added to the reaction system. After the completion of the dropwise addition, the mixture was naturally warmed to room temperature and reacted overnight. TLC (EA/PE-1:5) indicated the completion of the reaction, and the reaction was terminated. The reaction system was poured into a saturated ammonium chloride solution (400 mL) to quench the reaction. The reaction mixture was extracted with ethyl acetate (100 mL*3), washed with water (100 mL*2), washed with brine (100 mL*1), dried, and concentrated until 30 mL of the solvent remained. Petroleum ether (200 mL) was added, and the mixture was pulpified at room temperature for 1 hour, filtered, and dried to give Intermediate 3-8 (12 g), which was directly used in the next step.

(6) Preparation of Intermediate 3-9

Intermediate 3-8 (12.8 g, 39.5 mmol, 1.0 eq), tetrakis (triphenylphosphine)palladium (4.6 g, 3.95 mmol, 0.1 eq) and ammonium acetate (15.2 g, 197.3 mmol, 5.0 eq) were added to acetonitrile (250 mL). Nitrogen gas was introduced to remove oxygen gas. The mixture was heated to 70° C. and reacted overnight. TLC (EA/PE~1:3) indicated the completion of the reaction, and the reaction was terminated. The reaction system was poured into water (500 mL) to quench the reaction. The reaction mixture was extracted with ethyl acetate (300 mL*2), washed with water (300 mL*2), washed with brine (300 mL*1), dried, passed through a silica gel pad, and concentrated. The remaining liquid was refluxed in ethyl acetate (40 mL). Petroleum ether (150 mL) was added. The mixture was refluxed for 30 minutes, cooled to room temperature, filtered, and dried to give Intermediate 3-9 (10.8 g) in a yield of 96.4%, which was directly used in the next step.

(7) Preparation of Intermediate 3-10

Intermediate 3-9 (12.8 g, 37.0 mmol, 1.0 eq) was added to tetrahydrofuran (100 mL). The solid was not dissolved. A solution of sodium hydroxide (4.5 g) dissolved in water (25 mL) was added. The mixture was warmed up to 45-50° C. and reacted overnight. TLC (EA/PE~1:1) indicated the completion of the reaction, and the reaction was terminated. The reaction mixture was concentrated to remove tetrahydrofuran from the reaction system. Water (20 mL) was added for dilution. The reaction system was filtered. The solid was washed with a small amount of tetrahydrofuran. The solid was suspended in ethyl acetate and water and adjusted with acetic acid to a pH value of 2-3. The organic phase was separated, washed with water, washed with brine, dried, concentrated, pulpized with petroleum ether, filtered, and dried to give Intermediate 3-10 (5.7 g) in a yield of 57.2%.

(8) Preparation of Intermediate 3-11

Intermediate 3-10 (504 mg, 1.86 mmol) and L-threonine methyl ester hydrochloride (339 mg, 2 mmol) were dissolved in DMF (4 mL). DIEA (517 mg, 4 mmol) was added. The resulting solution was stirred for 50 minutes. After the solution became clear, HOBt (270 mg, 2 mmol) and EDCI (383 mg, 2 mmol) were added. The mixture was reacted under stirring for 15 hours. In the post-treatment, the reaction system was poured into water, extracted twice with ethyl acetate (100 mL), and separated into phases. The organic phase was rotary-evaporated to dryness and purified by column chromatography (DCM:MeOH=100:1→40:1) to give a product Intermediate 3-11 (300 mg).

(9) Preparation of Compound 3

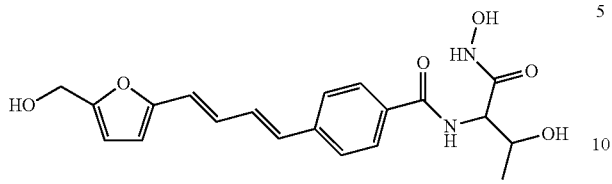

The crude product Intermediate 3-11 (270 mg) was dissolved in methanol (1.5 mL). An aqueous hydroxylamine solution (1 mL, 50%) was added. The mixture was reacted under stirring for 24 hours. In the post-treatment, the reaction system was poured into water. The mixture was filtered by suction. The filter cake was washed with water and dried to give Compound 3 (145 mg).

Molecular Formula: $C_{20}H_{22}N_{2}O_{6}$; Molecular Weight: 386.40; Mass Spectrum: (M+H): 387.1

$^{1}$H NMR (DMSO, 401 MHz) δ 12.84 (s, 1H), 7.90 (d, J=8.4 Hz, 3H), 7.59 (d, J=8.3 Hz, 3H), 7.20 (dd, J=15.5, 10.8 Hz, 2H), 6.90-6.74 (m, 3H), 6.64 (d, J=15.4 Hz, 2H), 6.50 (d, J=3.2 Hz, 2H), 6.35 (d, J=3.2 Hz, 1H), 5.27 (t, J=5.6 Hz, 1H), 4.41 (d, J=5.4 Hz, 3H).

Example 4: Preparation of 4-((5-(((dimethylamino)methyl)furan-2-yl)buta-1,3-diynyl)-N-((2S,3R)-3-hydroxy-1-(hydroxyamino)-1-oxobutan-2-yl)benzamide (Compound 4)

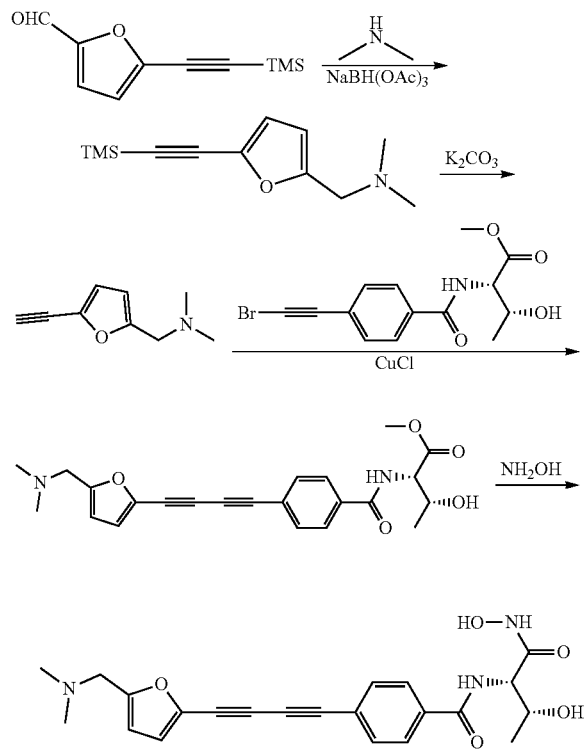

(1) Preparation of N,N-dimethyl-1-(5-((trimethylsilyl)ethynyl)furan-2-yl)methylamine

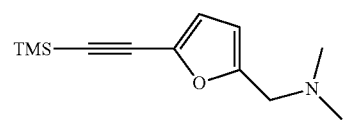

5-((trimethylsilyl)ethynyl)furan-2-carbaldehyde (0.500 g, 2.60 mmol) and a solution of dimethylamine in dichloromethane (3 mL) were dissolved in DCM (10 mL). Sodium triacetoxyhydroborate (1.10 g, 5.19 mmol) was added. The resulting mixture was reacted at room temperature under stirring for 1 day, and rotary-evaporated to dryness. The product was directly used in the next reaction.

(2) Preparation of 1-(5-ethynylfuran-2-yl)-N,N-dimethylmethylamine

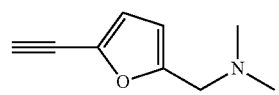

The crude product obtained in the above step was added to anhydrous methanol (10 mL). $K_2CO_3$ (1.435 g, 10.4 mmol) was added. The mixture was reacted at normal temperature under stirring for 5 hours. The reaction system was filtered by suction. The filtrate was rotary-evaporated to dryness and purified by silica column chromatography (PE:EA=10:1→1:1) to give an oily substance (0.35 g) in a yield of 90.3% for two steps.

(3) Preparation of (2S,3R)-methyl 2-(4-((5-(((dimethylamino)methyl)furan-2-yl)buta-1,3-diynyl)benzamido)-3-hydroxybutanoate

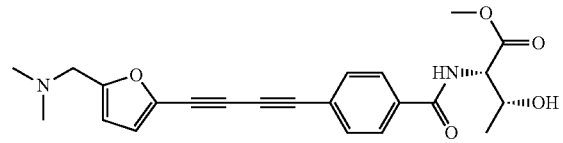 [SMILES: COC(=O)[C@@H](NC(=O)c1ccc(C#CC#Cc2ccc(CN(C)C)o2)cc1)[C@@H](C)O]

CuCl (2 mg, 0.02 mmol) and hydroxylamine hydrochloride (7 mg, 0.1 mmol) were dissolved in an aqueous n-butylamine solution (1.5 mL, 23%). 1-(5-ethynylfuran-2-yl)-N,N-dimethylmethylamine(0.20 g, 1.34 mmol) dissolved in an aqueous n-butylamine solution (0.5 mL, 23%) was added. A solution of (2S,3R)-methyl 2-(4-(bromoethynyl)benzamido)-3-hydroxybutanoate (0.456 g, 1.34 mmol) dissolved in methanol (1.5 mL) and tetrahydrofuran solution (0.75 mL) was added to the above reaction solution. The resulting mixture was stirred for 5 minutes. Ethyl acetate (20 mL) and water (20 mL) were added. The mixture was extracted. The organic phase was dried over anhydrous sodium sulphate, rotary-evaporated to dryness, and purified by silica column chromatography (DCM:MeOH=10:1) to give a product (0.26 g) in a yield of 47.5%.

(4) Preparation of 4-((5-((dimethylamino)methyl)furan-2-yl)buta-1,3-diynyl)-N-((2S,3R)-3-hydroxy-1-(hydroxyamino)-1-oxobutan-2-yl)benzamide

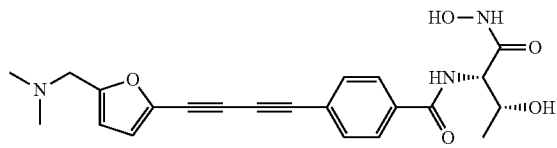

(2S,3R)-methyl 2-(4-((5-((dimethylamino)methyl)furan-2-yl)buta-1,3-diynyl)benzamido)-3-hydroxybutanoate (0.23 g, 0.563 mmol) was dissolved in methanol (1 mL). An aqueous hydroxylamine solution (3 mL, 50%) was added. The mixture was reacted at room temperature under stirring for 3 hours, and purified by a direct preparative liquid chromatography (methanol:water=50%) to give a product (0.035 g) in a yield of 15.2%.

Molecular Formula: $C_{22}H_{23}N_3O_5$; Molecular Weight: 409.2; Mass Spectrum: (M+H): 410.0

$^1$H-NMR ($d_6$-DMSO, 400 MHz) δ 8.42 (1H, s), 7.95 (2H, d), 7.70 (2H, d), 7.07 (1H, d), 6.44 (1H, d), 4.30-4.21 (1H, m), 4.05-3.95 (1H, m), 3.45 (2H, s), 2.15 (6H, s), 1.06 (3H, d).

Example 5: Preparation of N-methyl-N-(3-methylamino-1-(hydroxyamino)-1,3-dioxopropan-2-yl)-4-((5-(hydroxymethyl)furan-2-yl)buta-1,3-diynyl)benzamide (Compound 5)

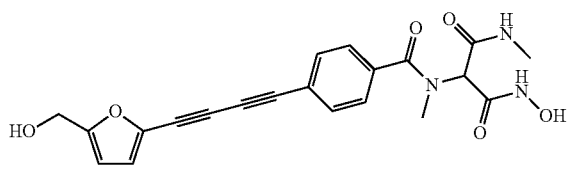 [SMILES: CNC(=O)C(C(=O)NO)N(C)C(=O)c1ccc(C#CC#Cc2ccc(CO)o2)cc1]

(1) Preparation of 5-((trimethylsilyl)ethynyl)furan-2-carbaldehyde

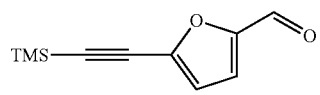

5-bromo-2-furaldehyde (25.00 g, 142.85 mmol), trimethylsilylethyne (20.97 g, 212.9 mmol), triethylamine (28.69 g, 283.5 mmol), Pd(PPh$_3$)$_2$Cl$_2$ (1.0 g, 1.425 mmol) and CuI (0.27 g, 1.415 mmol) were dissolved in THF (200 mL). The atmosphere was replaced with nitrogen gas three times. The mixture was stirred at normal temperature for 3 hours, rotary-evaporated to dryness, and purified by silica column chromatography (100% petroleum ether→petroleum ether:ethyl acetate=5:1) to give a pale red solid (18.2 g) in a yield of 66.4%.

(2) Preparation of 5-ethynylfuran-2-carbaldehyde

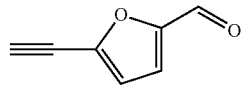

5-((trimethylsilyl)ethynyl)furan-2-carbaldehyde (15.52 g, 80.7 mmol) was dissolved in methanol (300 mL). K$_2$CO$_3$ (33.46 g, 242.1 mmol) was added. The mixture was reacted under stirring for 2 hours, and rotary-evaporated to dryness. Ethyl acetate (300 mL) and water (300 mL) were added. The mixture was extracted. The organic phase was dried over anhydrous sodium sulphate, and rotary-evaporated to dryness to give a yellow solid (9.5 g) in a yield of 98%.

(3) Preparation of (5-ethynylfuran-2-yl)methanol

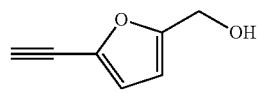

5-ethynylfuran-2-carbaldehyde (9.5 g, 79.17 mmol) was dissolved in anhydrous methanol (200 mL). NaBH$_4$ (3.292 g, 87.1 mmol) was slowly added at 0° C. The mixture was reacted at normal temperature under stirring for 7 hours. A saturated aqueous ammonium chloride solution (100 mL) was added. The reaction mixture was extracted with ethyl acetate (300 mL) and washed with water (200 mL). The organic phase was dried over anhydrous sodium sulphate, rotary-evaporated to dryness, and purified by silica column chromatography (100% petroleum ether→petroleum ether:ethyl acetate=2:1) to give a colorless oily substance (9.4 g) in a yield of 97.3%.

(4) Preparation of methyl 4-((trimethylsilyl)ethynyl)benzoate

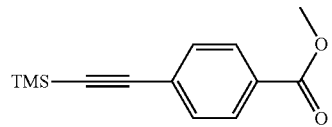

Methyl 4-iodobenzoate (40 g, 152.6 mmol), trimethylsilylethyne (14.99 g, 152.6 mmol), triethylamine (35.47 g, 350.5 mmol), Pd(PPh$_3$)$_2$Cl$_2$ (1.071 g, 1.526 mmol) and CuI (0.291 g, 1.526 mmol) were dissolved in THF (300 mL). The atmosphere was replaced with nitrogen gas three times. The mixture was stirred at normal temperature for 18 hours, rotary-evaporated to dryness, and purified by silica column chromatography (100% petroleum ether→petroleum ether:ethyl acetate=1:2) to give a red solid (31.5 g) in a yield of 88.9%.

(5) Preparation of methyl 4-ethynylbenzoate

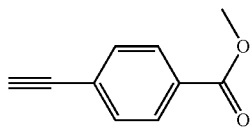

Methyl 4-((trimethylsilyl)ethynyl)benzoate (31.5 g, 135.6 mmol) was dissolved in methanol (450 mL). $K_2CO_3$ (37.5 g, 271.5 mmol) was added. The mixture was reacted under stirring for 2 hours, and rotary-evaporated to dryness. Ethyl acetate (450 mL) and water (450 mL) were added. The mixture was extracted. The organic phase was dried over anhydrous sodium sulphate, and rotary-evaporated to dryness to give a yellow solid (21.75 g) in a yield of 100%.

(6) Preparation of methyl 4-(bromoethynyl)benzoate

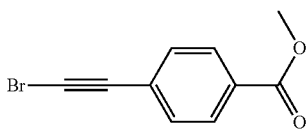

Methyl 4-ethynylbenzoate (21.75 g, 135.79 mmol) was dissolved in acetone (500 mL). Silver nitrate (2.176 g, 12.81 mmol) was added. The mixture was stirred for 40 minutes, and NBS (26.90 g, 151.16 mmol) was added. The resulting solution was stirred at room temperature for 2 hours and filtered. The filtrated was rotary-evaporated to dryness and crystallized in isopropanol to give a white solid (26.75 g) in a yield of 82.4%.

(7) Preparation of 4-(bromoethynyl)benzoic Acid

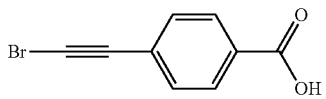 [SMILES: O=C(O)c1ccc(C#CBr)cc1]

Methyl 4-(bromoethynyl)benzoate (26.75 g, 111.89 mmol) was dissolved in methanol (200 mL) and water (20 mL). NaOH (8.96 g, 224 mmol) was added. The mixture was reacted under stirring for 2 hours. Water (350 mL) was added. The resulting mixture was adjusted with a diluted hydrochloric acid (1N) to a pH value of 6 and filtered to give a white solid (18.92 g) in a yield of 75%.

(8) Preparation of 4-(bromoethynyl)benzoyl Chloride

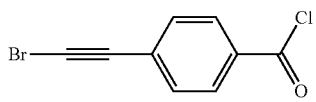 [SMILES: O=C(Cl)c1ccc(C#CBr)cc1]

4-(bromoethynyl)benzoic acid (8 g, 35.56 mmol) was dissolved in dichloromethane (200 mL). Thionyl chloride (30 mL) was added. The mixture was reacted under stirring for 5 hours, and rotary-evaporated to dryness to give a yellow solid (8.658 g) in a yield of 100%.

(9) Preparation of diethyl 2-((benzyl)methylamino)-malonate

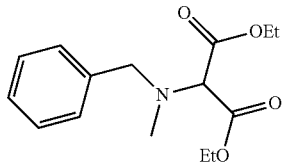 [SMILES: CCOC(=O)C(C(=O)OCC)N(C)Cc1ccccc1]

Diethyl 2-bromomalonate (80 g, 33.46 mmol) was added to acetonitrile (200 mL). Methylbenzylamine (81 g, 66.92 mmol) was added. The mixture was reacted at room temperature under stirring for 5 hours. After the completion of the reaction, the reaction mixture was filtered to remove a white solid. A majority of the filtrate was removed by rotary evaporation. To the reaction system was added toluene (100 mL), and the mixture was filtered to remove a white solid. The filtrate was collected, and rotary-evaporated to dryness for use to give a colorless oily substance (67 g) in a yield of 71.7%.

(10) Preparation of ethyl 2-(benzyl(methyl)amino)-3-(methylamino)-3-oxopropanoate

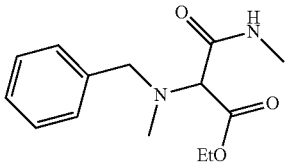 [SMILES: CCOC(=O)C(C(=O)NC)N(C)Cc1ccccc1]

Diethyl 2-((benzyl)methylamino)-malonate (50 g, 89.5 mmol) was dissolved in methanol (200 mL). A solution of methylamine in alcohol (30 mL) was added. The mixture was stirred at room temperature overnight. After the completion of the reaction, the reaction mixture was added to water (1000 mL). The reaction mixture was extracted with ethyl acetate three times, rotary-evaporated to dryness, purified by column chromatography to give an Intermediate ethyl 2-((benzyl)methylamino)-3-methylaminomalonate (12 g) in a yield of 25.4% (PE→PE:EA=5:1).

(11) Preparation of ethyl 2-((tert-butoxycarbonyl)methylamino)-3-oxopropanoate

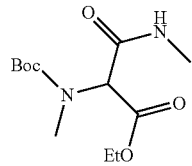

Ethyl 2-((benzyl)methylamino)-3-oxopropanoate (12 g, 45.4 mmol) was dissolved in methanol (200 mL). Palladium hydroxide/carbon (1.2 g) and di-tert-butyl dicarbonate (9.9 g, 45.4 mmol) were added. Under the protection of hydrogen gas, the reaction was reacted at room temperature overnight. After the completion of the reaction, the mixture was filtered through celite. The filtrate was collected, and rotary-evaporated to dryness, purified by column chromatography to give Intermediate (6.4 g) in a yield of 51.4% (PE→PE:EA=20:1).

(12) Preparation of ethyl 2-methylamino-3-oxopropanoate

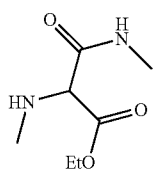

Ethyl 2-((tert-butoxycarbonyl)methylamino)-3-oxopropanoate (6.4 g, 23.33 mmol) was dissolved in dichloromethane (100 mL). Trifluoroacetic acid (30 mL) was added. The mixture was stirred at room temperature overnight. After the completion of the reaction, the reaction mixture was rotary-evaporated to dryness to give a brown oily substance (4.064 g, crude) in a yield of 100%.

(13) Preparation of ethyl 2-(N-(4-bromoethynylbenzamido)-N-methylamino)-3-oxopropanoate

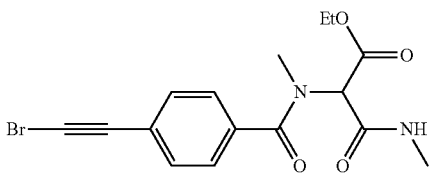 [SMILES: CCOC(=O)C(C(=O)NC)N(C)C(=O)c1ccc(C#CBr)cc1]

Ethyl 2-methylamino-3-oxopropanoate (4.064 g, 23.3 mmol) was dissolved in THF (100 mL). Triethylamine (7.06 g, 69.9 mmol) was added. 4-(bromoethynyl)benzoyl chloride (5.674 g, 23.3 mmol) was added. The mixture was stirred at room temperature overnight. After the completion of the reaction, the reaction mixture was rotary-evaporated to dryness and purified by column chromatography to give a brown oily substance (5.2 g) in a yield of 58.6% (DCM-DCM:MeOH=30:1).

(14) Preparation of ethyl 2-((4-(5-(hydroxymethyl)-tetrahydrofuran-2-yl)buta-1,3-diynyl)-N-benzamido-N-methylamino)-3-oxopropanoate

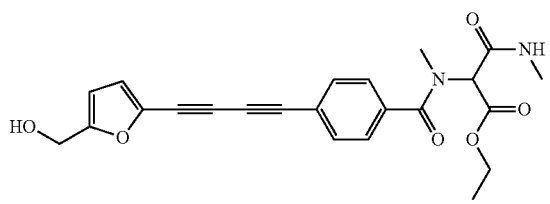 [SMILES: CCOC(=O)C(C(=O)NC)N(C)C(=O)c1ccc(C#CC#Cc2ccc(CO)o2)cc1]

CuCl (3 mg, 0.03 mmol) and hydroxylamine hydrochloride (7 mg, 0.1 mmol) were dissolved in an aqueous n-butylamine solution (12 mL, 23%). A solution of (5-ethynylfuran-2-yl)methanol (0.220 g, 1.80 mmol) in methanol and tetrahydrofuran (5 mL, V:V, 1:1), and a solution of ethyl 2-(N-(4-bromoethynylbenzamido)-N-methylamino)-3-oxopropanoate (0.629 g, 1.65 mmol) in methanol and tetrahydrofuran (5 mL, V:V, 1:1) were successively added to the above reaction solution. The resulting mixture was stirred for 2 minutes. Ethyl acetate (20 mL) and water (20 mL) were added. The mixture was extracted. The organic phase was dried over anhydrous sodium sulphate, rotary-evaporated to dryness, and purified by silica column chromatography (100% petroleum ether→petroleum ether:ethyl acetate=2:1) to give a brown oily substance (0.49 g) in a yield of 70.3%.

(15) Preparation of N-methyl-N-(3-methylamino-1-(hydroxyamino)-1,3-dioxopropan-2-yl)-4-((5-(hydroxymethyl)furan-2-yl)buta-1,3-diynyl)benzamide

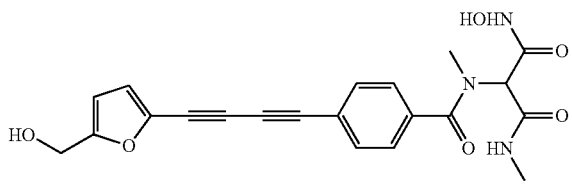

Ethyl 2-((4-(5-(hydroxymethyl)-tetrahydrofuran-2-yl)buta-1,3-diynyl)-N-benzamido-N-methylamino)-3-oxopropanoate (0.49 g, 1.16 mmol) was dissolved in methanol (10 mL). An aqueous hydroxylamine solution (50%, 2 mL) was added. The mixture was reacted under stirring for 24 hours. In the post-treatment, Compound 5 was prepared (in a total of 132 mg) in a yield of 27.8%.

Molecular Formula: $C_{21}H_{19}N_3O_6$; Molecular Weight: 409.1; Mass Spectrum: (2M+H): 819.3

$^1$H-NMR (DMSO-$d_6$, 400 MHz) δ 10.79 (1H, s), 9.05 (1H, s), 8.19 (1H, m), 7.71 (2H, m), 7.41 (2H, m), 7.07 (1H, m), 6.45 (1H, m), 5.43 (1H, m), 5.35 (1H, s), 4.41 (2H, m), 2.66 (3H, m), 2.49 (3H, m).

Example 6: Preparation of N-((2S,3R)-3-hydroxy-1-(hydroxyamino)-1-oxobutan-2-yl)-4-((5-(hydroxymethyl)furan-2-yl)buta-1,3-diynyl)benzamide (Compound 6)

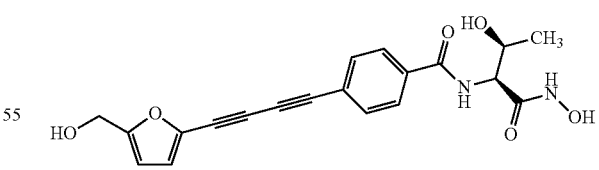

With reference to the preparation of the above Compound 3, (2S,3R)-methyl 2-(4-(bromoethynyl)benzamido)-3-hydroxybutanoate was used to synthesize Compound 6.

Molecular Formula: $C_{20}H_{18}N_2O_6$; Molecular Weight: 382.1; Mass Spectrum: (M+H): 383.1

$^1$H-NMR ($d_6$-DMSO+CF$_3$COOD, 400 MHz) δ 8.19 (1H, d), 7.93 (2H, d), 7.70 (2H, d), 7.03 (1H, d), 6.42 (1H, d), 4.40 (2H, s), 4.29-4.21 (1H, m), 4.06-3.98 (1H, m), 3.58 (1H, t), 1.07 (3H, d).

With reference to the preparation of the above Compound 3, methyl 2-(4-(bromoethynyl)benzamido)-3-hydroxybutanoate was used to synthesize Compound 7.

With reference to the preparation of the above Compound 3, (2R,3S)-methyl 2-(4-(bromoethynyl)benzamido)-3-hydroxybutanoate was used to synthesize N-((2R,3S)-3-hydroxy-1-(hydroxyamino)-1-oxobutan-2-yl)-4-((5-(hydroxymethyl)furan-2-yl)buta-1,3-diynyl)benzamide (Compound 8).

With reference to the preparation of the above Compound 3, (2R,3R)-methyl 2-(4-(bromoethynyl)benzamido)-3-hydroxybutanoate was used to synthesize N-((2R,3R)-3-hydroxy-1-(hydroxyamino)-1-oxobutan-2-yl)-4-((5-(hydroxymethyl)furan-2-yl)buta-1,3-diynyl)benzamide (Compound 9).

With reference to the preparation of the above Compound 3, (2S,3S)-methyl 2-(4-(bromoethynyl)benzamido)-3-hydroxybutanoate was used to synthesize N-((2S,3S)-3-hydroxy-1-(hydroxyamino)-1-oxobutan-2-yl)-4-((5-(hydroxymethyl)furan-2-yl)buta-1,3-diynyl)benzamide (Compound 10).

Compounds 6 and 8-10 were the stereoisomers of compound 7. Their $^1$H-NMR data are substantially identical without an obvious difference.

High performance liquid chromatography (HPLC)
HPLC conditions:
Instrument: High performance liquid chromatograph; Column: Agilent ZORBAX SB-C18 (4.6 mm×100 mm, 3.5 μm); wavelength=286 nm; column temperature=30° C.; flow rate=1.0 mL/minutes; injection volume=10 μL; gradient elution;

Mobile phase A: prepared by precisely measuring 0.8 mL of trifluoroacetic acid, adding to 1000 mL of water, and mixing homogenously.

Mobile phase B: prepared by precisely measuring 0.5 mL of trifluoroacetic acid, adding to 1000 mL of methanol, and mixing homogenously.

Test sample solutions: prepared by taking appropriate amounts of Compound 6, Compound 9, and Compound 10, accurately weighing, adding methanol to dissolve the compounds to obtain solutions containing about 0.5 mg of the compound per 1 mL as the test sample solution.

Experiment results: Compound 6 had a retention time of 26.601 minutes;
Compound 9 had a retention time of 28.799 minutes;
Compound 10 had a retention time of 29.051 minutes.

Example 7: Preparation of 4-((5-((cyclopropylamino)methyl)furan-2-yl)buta-1,3-diynyl)-N-((2S, 3R)-3-hydroxy-1-(hydroxamino)-1-oxobutan-2-yl) benzamide (Compound 11)

With reference to the preparation of the above Compound 3, Compound 11 was synthesized.

Molecular Formula: $C_{23}H_{23}N_3O_5$; Molecular Weight: 421.2; Mass Spectrum (M+H): 422.0

$^1$H-NMR (DMSO-$d_6$, 400 MHz) δ 10.70 (1H, s), 9.19 (1H, br), 8.89 (1H, s), 8.20 (1H, d), 7.94 (2H, d), 7.72 (2H, d), 7.17 (1H, d), 6.74 (1H, d), 4.94 (1H, m), 4.36 (2H, s), 4.26-4.21 (1H, m), 4.04-3.98 (1H, m), 2.75-2.60 (1H, m), 1.07 (3H, d), 0.87-0.79 (2H, m), 0.76-0.70 (2H, m).

Example 8: Preparation of 4-((5-((3-aminopropylamino)methyl)furan-2-yl)buta-1,3-diynyl)-N-((2S, 3R)-3-hydroxy-1-(hydroxyamino)-1-oxobutan-2-yl) benzamide (Compound 12)

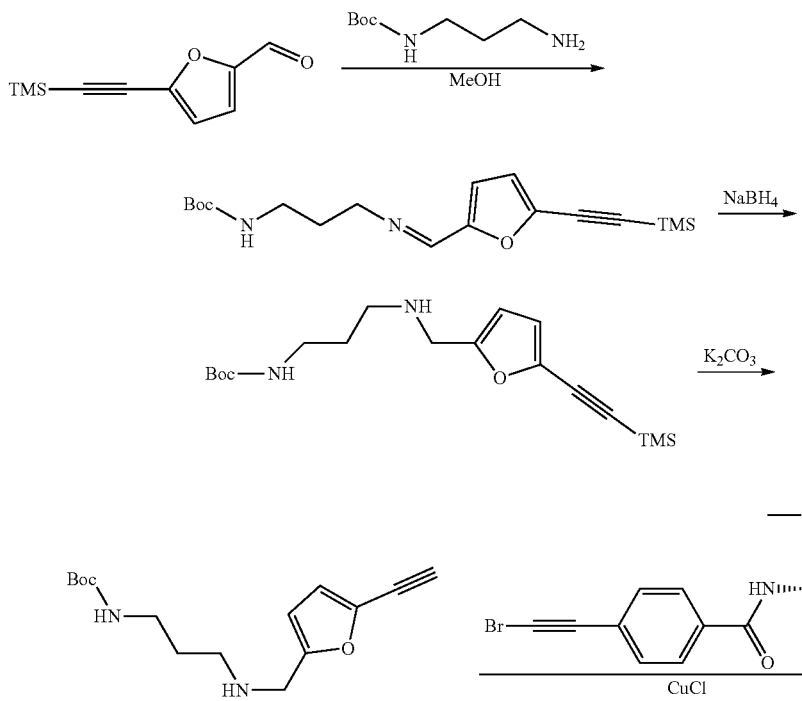

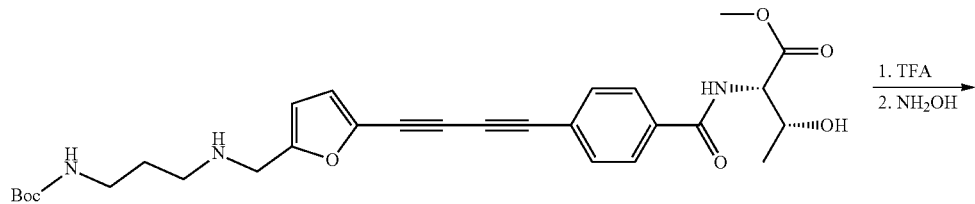

(1) Preparation of tert-butyl 3-((5-(((trimethylsilyl)ethynyl)furan-2-yl)methyleneamino)propylcarbamate

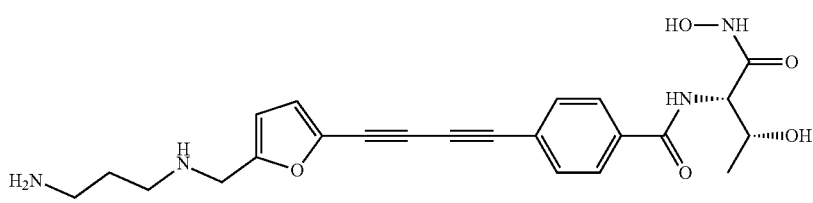

5-((trimethylsilyl)ethynyl)furan-2-carbaldehyde (0.500 g, 2.60 mmol) was dissolved in methanol (10 mL). Tert-butyl 3-aminopropylcarbamate (0.905 g, 5.20 mmol) was added. A dropwise of acetic acid was added. The mixture was stirred at room temperature overnight. The product was directly used in the next reaction.

(2) Preparation of tert-butyl 3-((5-(((trimethylsilyl)ethynyl)furan-2-yl)methylamino)propylcarbamate

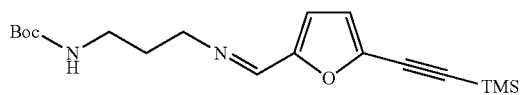 [SMILES: CC(C)(C)OC(=O)NCCCN=Cc1ccc(C#C[Si](C)(C)C)o1]

To the reaction system from the previous step was added sodium borohydride (0.197 g, 5.20 mmol). The mixture was stirred at room temperature for 1 hour. LC-MS indicated the completion of the reaction. The product did not need any further treatment and was directly used in the next reaction.

(3) Preparation of tert-butyl 3-((5-ethynylfuran-2-yl)methylamino)propylcarbamate

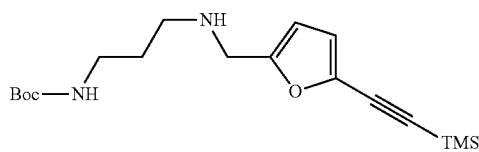 [SMILES: CC(C)(C)OC(=O)NCCCNCc1ccc(C#C[Si](C)(C)C)o1]

To the reaction system from the previous step potassium carbonate (0.717 g, 5.20 mmol) was added. The mixture was reacted at room temperature for 4 hours. After the completion of the reaction, water (100 mL) was added to the reaction system. The reaction mixture was extracted with ethyl acetate three times. The organic phases were combined, washed with water, washed with saturated brine, dried over anhydrous sodium sulphate, rotary-evaporated to dryness, and purified by column chromatography (PE:EA=5:1→DCM:MeOH=10:1) to give an oily substance (0.35 g) in a yield (for three steps) of 48.5%.

(4) Preparation of (2S,3R)-methyl 2-(4-((5-((3-(tert-butoxycarbonylamino)propylamino)methyl)furan-2-yl)buta-1,3-diynyl)benzamido)-3-hydroxybutanoate

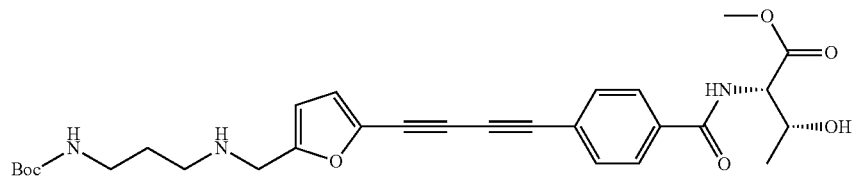 [SMILES: COC(=O)[C@@H](NC(=O)c1ccc(C#CC#Cc2ccc(CNCCCNC(=O)OC(C)(C)C)o2)cc1)[C@@H](C)O]

CuCl (3 mg, 0.03 mmol) and hydroxylamine hydrochloride (7 mg, 0.1 mmol) were dissolved in an aqueous n-butylamine solution (2 mL, 23%). A solution of tert-butyl 3-((5-ethynylfuran-2-yl)methylamino)propylcarbamate (0.33 g, 1.19 mmol) in methanol and tetrahydrofuran (5 mL, V:V, 1:1) and a solution of (2S,3R)-methyl 2-(4-(bromoethynyl)benzamido)-3-hydroxybutanoate (0.404 g, 1.19 mmol) in methanol and tetrahydrofuran (5 mL, V:V, 1:1) were successively added to the above reaction solution. The mixture was stirred for 2 min. Dichloromethane (20 mL) and water (20 mL) were added. The mixture was extracted. The organic phase was dried over anhydrous sodium sulphate, rotary-evaporated to dryness, and purified by silica column chromatography (petroleum ether:ethyl acetate=5:1→dichloromethane:methanol=10:1) to give a red brown solid (0.38 g) in a yield of 59.4%.

(5) Preparation of 4-((5-((3-aminopropylamino)methyl)furan-2-yl)buta-1,3-diynyl)-N-((2S,3R)-3-hydroxy-1-(hydroxyamino)-1-oxobutan-2-yl)benzamide

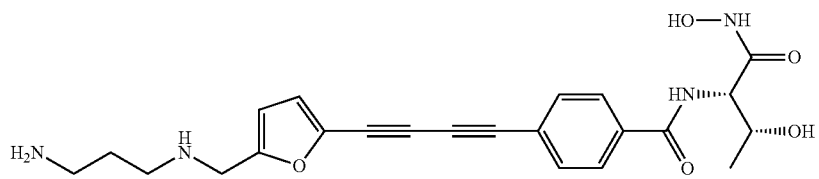 [SMILES: C[C@@H](O)[C@H](NC(=O)c1ccc(C#CC#Cc2ccc(CNCCCN)o2)cc1)C(=O)NO]

(2S,3R)-methyl 2-(4-((5-((tert-butoxycarbonyl(2-(2-hydroxyethoxy)ethyl)amino)methyl)furan-2-yl)buta-1,3-diynyl)benzamido)-3-hydroxybutanoate (0.38 g, 0.707 mmol) was dissolved in dichloromethane (10 mL). TFA (2 mL) was added. The mixture was reacted under stirring for 30 minutes, and rotary-evaporated to dryness. The resulting oily substance was dissolved in methanol (1 mL). An aqueous hydroxylamine solution (50%, 4 mL) was added. The mixture was reacted under stirring for 3 hours, and directly purified by preparative liquid phase chromatography to give Compound 12 (in total of 79 mg) in a yield of 25.5%.

Molecular Formula: $C_{23}H_{26}N_4O_5$; Molecular Weight: 438.2; Mass Spectrum: (M+H): 439.0

$^1$H-NMR (DMSO-$d_6$, 400 MHz) δ 8.24 (1H, d), 7.94 (2H, d), 7.71 (2H, d), 7.05 (1H, d), 6.39 (1H, d), 4.25 (1H, dd), 4.01 (1H, quintet), 3.66 (2H, s), 3.43 (4H, m), 2.68-2.52 (2H, m), 1.54-1.40 (2H, m), 1.07 (3H, d).

Example 9: Preparation of N-((2S,3R)-3-hydroxy-1-(hydroxyamino)-1-oxobutan-2-yl)-4-((5-((4-methylpiperazin-1-yl)methyl)furan-2-yl)buta-1,3-diynyl)benzamide (Compound 13)

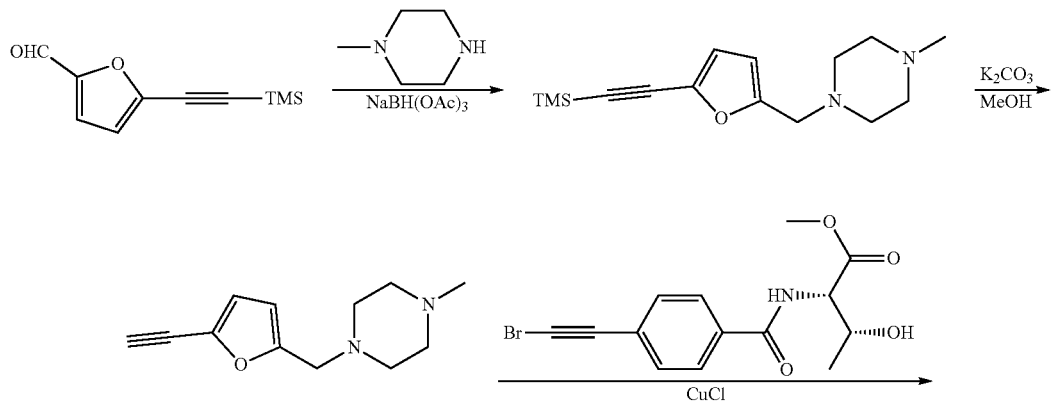

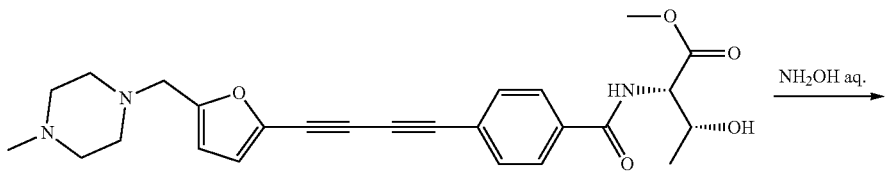

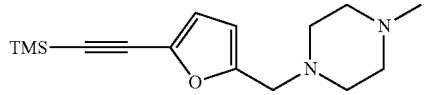 [SMILES: CN1CCN(Cc2ccc(C#C[Si](C)(C)C)o2)CC1]

(1) Preparation of 1-methyl-4-((5-((trimethylsilyl)ethynyl)furan-2-yl)methyl)piperazine In a dry reaction flask, 5-((trimethylsilyl)ethynyl)furan-2-carbaldehyde (308 mg, 1.6 mmol) and 1-methylpiperazine (192 mg, 1.92 mmol) were dissolved in dichloromethane (20 mL). Sodium triacetoxyhydroborate (509 mg, 2.4 mmol) was added. The mixture was stirred at room temperature for 20 hours, concentrated to remove dichloromethane and to give an oily substance, which was directly used in the next reaction.

(2) Preparation of 1-((5-ethynylfuran-2-yl)methyl)-4-methylpiperazine

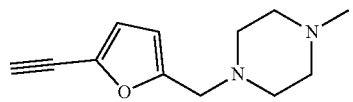

In a dry reaction flask, the crude product obtained in the previous step was added, and dissolved in methanol (20 mL). Potassium carbonate (442 mg, 3.2 mmol) and lithium hydroxide (200 mg) were added. After the completion of the addition, the mixture was stirred at room temperature for 1 hour. The organic phase was directly concentrated under reduced pressure and purified by column chromatography (100% EA) to give a pale-yellow solid (320 mg) in a yield of 97.9%.

(3) Preparation of (2S,3R)-methyl 3-hydroxy-2-(4-((5-((4-methylpiperazin-1-yl)methyl)furan-2-yl)buta-1,3-diynyl)benzamido)butanoate

In a dry reaction flask, CuCl (28 mg, 0.284 mmol) and hydroxylamine hydrochloride (296 mg, 4.26 mmol) were dissolved in an aqueous n-butylamine solution (3 mL, 23%). To the above reaction solution a solution of 1-((5-ethynyl-furan-2-yl)methyl)-4-methylpiperazine (290 mg, 1.42 mmol) in an aqueous n-butylamine (1 mL, 23%), and then a solution of (2S,3R)-methyl 2-(4-(bromoethynyl)benzamido)-3-hydroxybutanoate (340 mg, 1 mmol) in methanol (6 mL) and tetrahydrofuran (3 mL) were added. The resulting mixture was stirred for 5 minutes. Ethyl acetate (20 mL) and water (20 mL) were added. The mixture was extracted. The organic phase was dried over anhydrous sodium sulphate, rotary-evaporated to dryness, and purified by silica column chromatography (DCM:MeOH=20:1) to give a product (360 mg) in a yield of 54.7%.

(4) Preparation of N-((2S,3R)-3-hydroxy-1-(hydroxyamino)-1-oxobutan-2-yl)-4-((5-((4-methylpiperazin-1-yl)methyl)furan-2-yl)buta-1,3-diynyl)benzamide

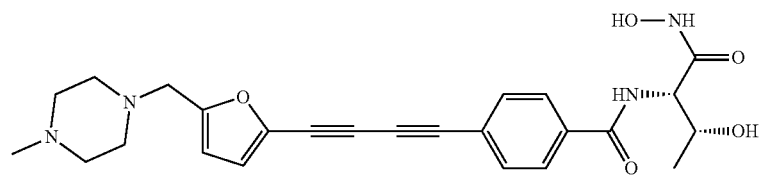 [SMILES: C[C@@H](O)[C@H](NC(=O)c1ccc(C#CC#Cc2ccc(CN3CCN(C)CC3)o2)cc1)C(=O)NO]

Methyl (2S,3R)-3-hydroxy-2-(4-((5-((4-methylpiperazin-1-yl)methyl)furan-2-yl)buta-1,3-diynyl)benzamido)butanoate (360 mg, 0.78 mmol) was dissolved in methanol (5 mL). An aqueous hydroxylamine solution (50%, 3 mL) was added. The mixture was reacted at room temperature under stirring for 8 hours and reacted in a refrigerator for 12 hours, then purified by preparative liquid-phase chromatography (methanol:water=55%) to give a product (40 mg) in a yield of 11.0%.

Molecular Formula: $C_{25}H_{28}N_4O_5$; Molecular Weight: 464.2; Mass Spectrum: (M+H): 465.2

$^1$H-NMR (d$_6$-DMSO, 400 MHz) δ 10.70 (1H, s), 8.88 (1H, s), 8.23 (1H, d), 7.96 (2H, d), 7.74 (2H, d), 7.09 (1H, d), 6.46 (1H, d), 4.90 (1H, d), 4.26 (1H, dd), 4.03 (1H, q), 3.53 (2H, s), 2.45-2.23 (8H, m), 2.14 (3H, s), 1.09 (3H, d).

Example 10: Preparation of N-((2S,3R)-3-hydroxy-1-(hydroxyamino)-1-oxobutan-2-yl)-4-((5-phenyl-furan-2-yl)buta-1,3-diynyl)benzamide (Compound 14)

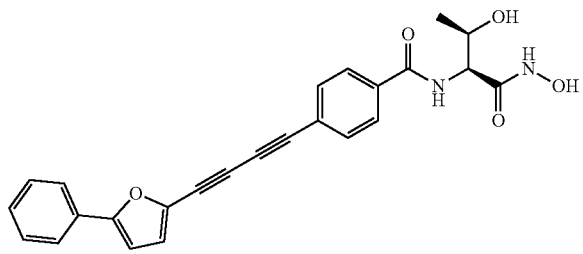 [SMILES: C[C@@H](O)[C@H](NC(=O)c1ccc(C#CC#Cc2ccc(-c3ccccc3)o2)cc1)C(=O)NO]

With reference to Example 9, Compound 14 was synthesized.

Molecular Formula: $C_{25}H_{20}N_2O_5$; Molecular Weight: 428.1; Mass Spectrum: (M+H): 429.1, 396.1

$^1$H-NMR (DMSO-d$_6$, 600 MHz) δ 10.67 (1H, s), 8.84 (1H, s), 8.20 (1H, d), 7.95 (2H, d), 7.77 (2H, d), 7.74 (2H, d), 7.47 (2H, t), 7.37 (1H, t), 7.26 (1H, d), 7.14 (1H, d), 4.90 (1H, s), 4.25 (1H, dd), 4.02 (1H, dt), 1.08 (3H, d).

Example 11: Preparation of N-((2S,3R)-3-hydroxy-1-(hydroxyamino)-1-oxobutan-2-yl)-4-((5-((methylamino)methyl)furan-2-yl)buta-1,3-diynyl)benzamide (Compound 15)

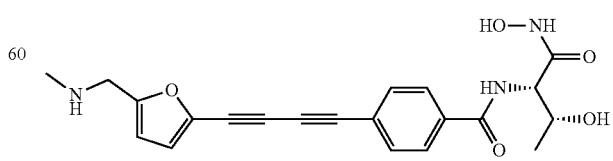

With reference to Example 3, Compound 15 was synthesized.

Molecular Formula: $C_{21}H_{21}N_3O_5$; Molecular Weight: 395.1; Mass Spectrum: (M+H): 396.2

$^1$H-NMR (d$_6$-DMSO, 400 MHz) δ 10.75 (1H, br s), 8.87 (1H, s), 8.23 (1H, d), 7.96 (2H, d), 7.74 (2H, d), 7.08 (1H, d), 6.42 (1H, d), 4.90 (1H, d), 4.26 (1H, dd), 4.03 (1H, q), 3.65 (2H, s), 2.26 (3H, s), 1.09 (3H, d).

Example 12: Preparation of N-((2S,3R)-3-hydroxy-1-(hydroxyamino)-1-oxobutan-2-yl)-4-((5-(hydroxymethyl)-4-methylfuran-2-yl)buta-1,3-diynyl)benzamide (Compound 16)

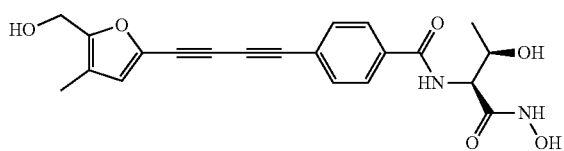 [SMILES: Cc1cc(C#CC#Cc2ccc(C(=O)N[C@H](C(=O)NO)[C@@H](C)O)cc2)oc1CO]

With reference to the preparation of the above Compound 3, Compound 16 was synthesized.

Molecular Formula: $C_{21}H_{20}N_2O_6$; Molecular Weight: 396.1; Mass Spectrum: (M+H): 397.1

$^1$H-NMR (DMSO-d$_6$, 600 MHz) δ 7.92 (2H, d), 7.67 (2H, d), 6.88 (1H, s), 4.33 (2H, s), 4.23 (1H, dd), 4.00 (1H, dt), 1.95 (3H, s), 1.06 (3H, d).

Example 13: Preparation of N-((2S,3R)-3-hydroxy-1-(hydroxyamino)-1-oxobutan-2-yl)-4-((5-(hydroxymethyl)-3-phenylfuran-2-yl)buta-1,3-diynyl)benzamide (Compound 17)

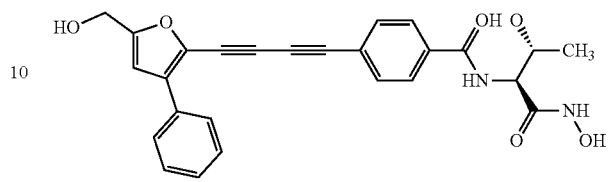

With reference to the preparation of the above Compound 3, Compound 17 was synthesized.

Molecular Formula: $C_{26}H_{22}N_2O_6$; Molecular Weight: 458.1; Mass Spectrum: (M+H): 459.1

$^1$H-NMR (DMSO-d$_6$, 600 MHz) δ 10.67 (1H, s), 8.85 (1H, s), 8.20 (1H, d), 7.93 (2H, d), 7.77 (2H, d), 7.74 (2H, d), 7.48 (2H, t), 7.38 (1H, t), 6.90 (1H, s), 5.51 (1H, t), 4.88 (1H, d), 4.43 (2H, d), 4.23 (1H, dd), 4.00 (1H, dt), 1.06 (3H, d).

Example 14: Preparation of N-((2S,3R)-3-hydroxy-1-(hydroxyamino)-1-oxobutan-2-yl)-4-((5-((2-(2-hydroxyethoxy)ethylamino)methyl)furan-2-yl)buta-1,3-diynyl)benzamide (Compound 18)

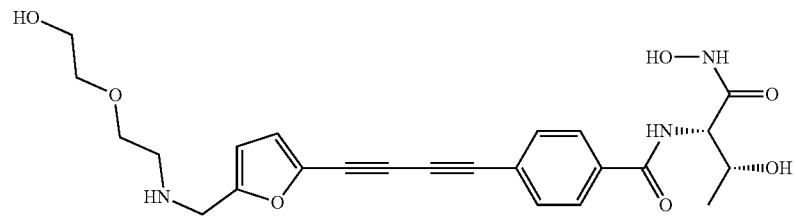 [SMILES: C[C@@H](O)[C@H](NC(=O)c1ccc(C#CC#Cc2ccc(CNCCOCCO)o2)cc1)C(=O)NO]

With reference to Example 8, Compound 18 was synthesized.

Molecular Formula: $C_{24}H_{27}N_3O_7$; Molecular Weight: 469.2; Mass Spectrum: (M+H): 470 $^1$H-NMR (DMSO-d$_6$, 400 MHz) δ 10.66 (1H, s), 8.84 (1H, s), 8.19 (1H, d), 7.93 (2H, d), 7.71 (2H, d), 7.05 (1H, d), 6.40 (1H, d), 4.88 (1H, d), 4.64-4.52 (1H, m), 4.24 (1H, dd), 4.06-3.95 (1H, m), 3.71 (2H, s), 3.50-3.41 (4H, m), 3.40-3.35 (3H, m), 2.64 (2H, t), 1.07 (3H, d).

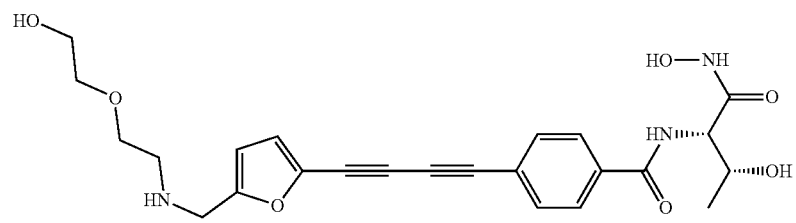

With reference to Example 8, Compound 19 was synthesized.

Molecular Formula: $C_{24}H_{27}N_3O_6$; Molecular Weight: 453.2; Mass Spectrum: (M+H): 454.0

$^1$H-NMR (DMSO-d$_6$, 400 MHz) δ 10.69 (1H, s), 8.85 (1H, s), 8.22 (1H, d), 7.95 (2H, d), 7.71 (2H, d), 7.06 (1H, d), 6.42 (1H, d), 4.90 (1H, d), 4.28-4.20 (1H, m), 4.08-3.97 (1H, m), 3.72 (2H, s), 3.49 (1H, s), 3.36 (2H, m), 2.05-1.92 (2H, m), 1.46-1.39 (4H, m), 1.07 (3H, d).

Example 16: Preparation of N-((2S,3R)-3-hydroxy-1-(hydroxyamino)-1-oxobutan-2-yl)-4-(furan-2-yl)buta-1,3-diynyl)benzamide (Compound 20)

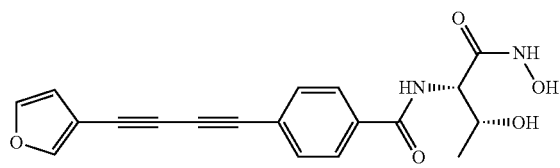 [SMILES: C[C@@H](O)[C@H](NC(=O)c1ccc(C#CC#Cc2ccoc2)cc1)C(=O)NO]

With reference to Example 3, Compound 20 was synthesized.

Molecular Formula: $C_{19}H_{16}N_2O_5$; Molecular Weight: 352.1; Mass Spectrum: (M+H): 353.1

$^1$H-NMR (DMSO-d$_6$, 400 MHz) δ 10.7 (1H, S), 8.89 (1H, S), 8.30 (1H, S), 8.23 (1H, m), 7.96 (2H, m), 7.82 (1H, s), 7.72 (2H, m), 6.76 (1H, s), 4.92 (1H, s), 4.27 (1H, m), 4.04 (1H, s), 1.1 (3H, m).

Example 17: Preparation of N-((2S,3R)-3-hydroxy-1-(hydroxyamino)-1-oxobutan-2-yl)-4-((5-((2-(2-hydroxyethoxy)ethoxy)methyl)furan-2-yl)buta-1,3-diynyl)benzamide (Compound 21)

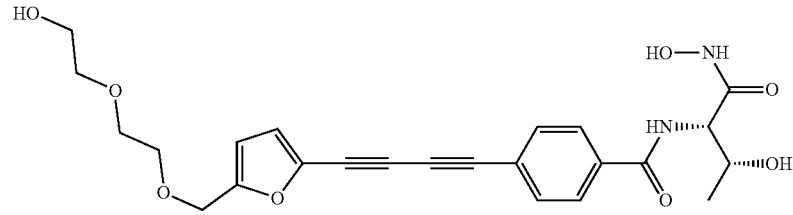 [SMILES: C[C@@H](O)[C@H](NC(=O)c1ccc(C#CC#Cc2ccc(COCCOCCO)o2)cc1)C(=O)NO]

With reference to Example 8, Compound 21 was synthesized.

Molecular Formula: $C_{24}H_{26}N_2O_8$; Molecular Weight: 470.2; Mass Spectrum: (M+H): 471.2

$^1$H-NMR (DMSO-d$_6$, 400 MHz) 10.72 (1H, s), 8.90 (1H, s), 8.21 (1H, d), 7.95 (2H, d), 7.74 (2H, d), 7.10 (1H, d), 6.59 (1H, d), 4.94 (1H, d), 4.64 (1H, t), 4.47 (2H, s), 4.25 (1H, dd), 4.03 (1H, q), 3.68-3.52 (8H, m), 1.09 (3H, d).

Example 18: Preparation of N-((2S,3R)-3-hydroxy-1-(hydroxyamino)-1-oxobutan-2-yl)-4-((5-((3-morpholinopropylamino)methyl)furan-2-yl)buta-1,3-diynyl)benzamide (Compound 22)

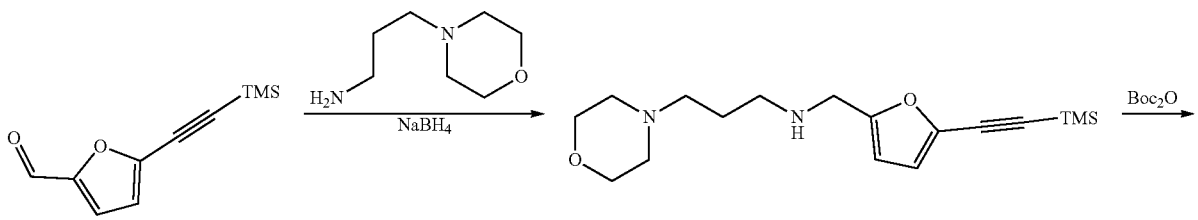

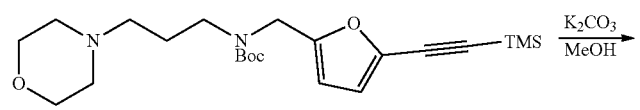

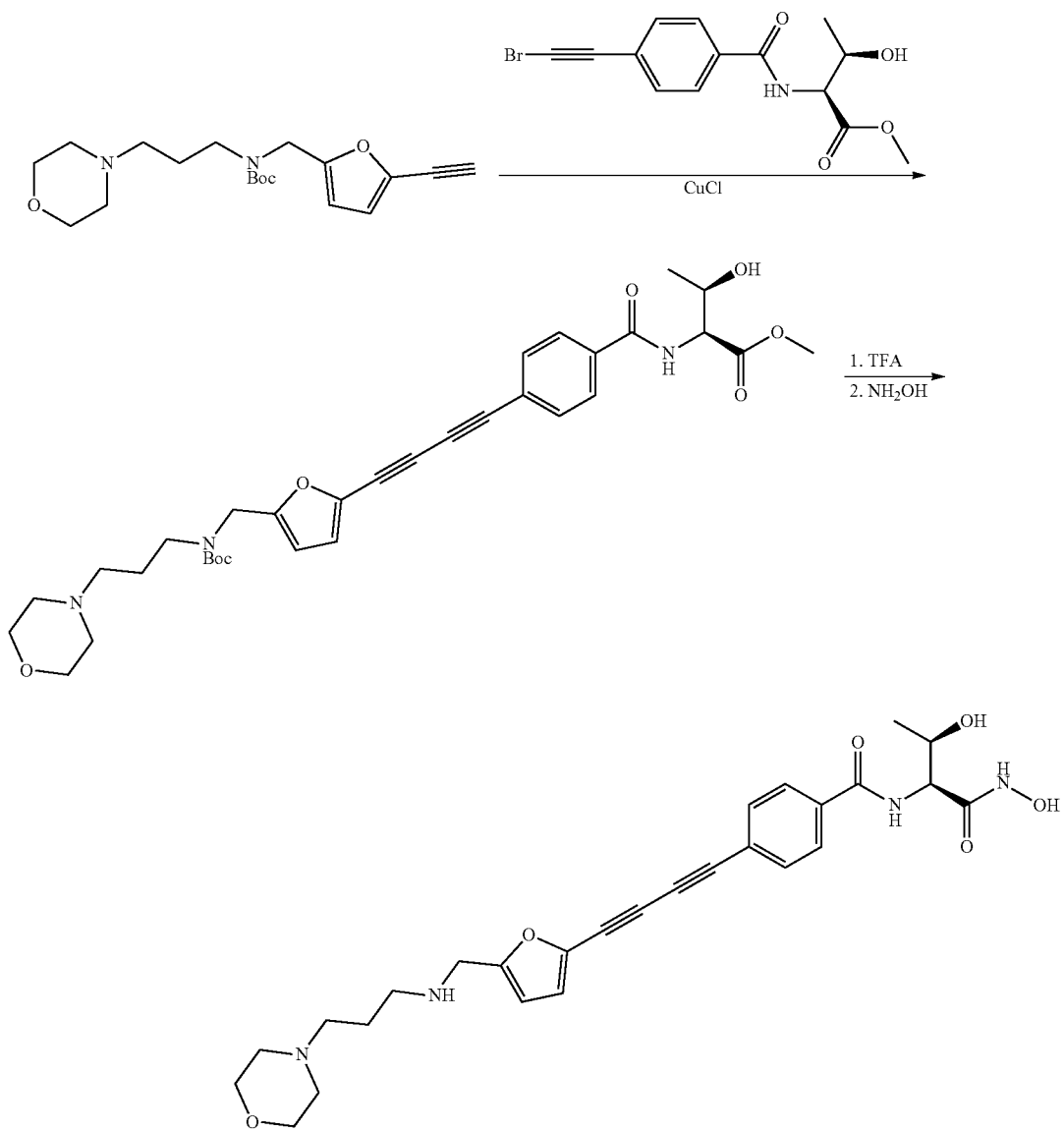

(1) Preparation of 3-morpholino-N-((5-((trimethylsilyl)ethynyl)furan-2-yl)methyl)propan-1-amine

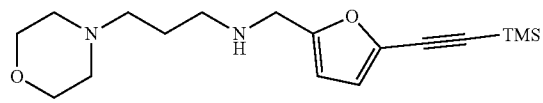 [SMILES: C[Si](C)(C)C#Cc1ccc(CNCCCN2CCOCC2)o1]

5-((trimethylsilyl)ethynyl)furan-2-carbaldehyde (192 mg, 1 mmol) and 3-morpholinopropan-1-amine (144 mg, 1 mmol) were added to methanol (10 mL). Three drops of glacial acetic acid were added. The mixture was reacted at 40° C. for 18 hours. Then sodium borohydride (57 mg, 1.5 mmol) was added. The mixture was reacted for 4 hours. The same reaction was amplified by 2.6 times, and the products were combined and directly rotary-evaporated to dryness for the next step of the reaction.

(2) Preparation of tert-butyl 3-morpholinopropyl((5-((trimethylsilyl)ethynyl)furan-2-yl)methyl)carbamate

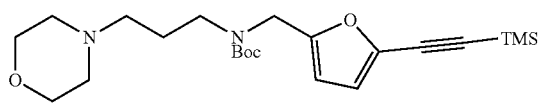 [SMILES: CC(C)(C)OC(=O)N(CCCN1CCOCC1)Cc1ccc(C#C[Si](C)(C)C)o1]

The product from the above step was dissolved in dichloromethane (30 mL). Triethylamine (505 mg, 5 mmol), and di-tert-butyl dicarbonate (872 mg, 4 mmol) were added. The mixture was reacted at room temperature for 24 hours, rotary-evaporated to dryness, purified by column chromatography (PE:EA=3:1) to give a yellow solid (1.06 g).

(3) Preparation of tert-butyl (5-ethynylfuran-2-yl)methyl(3-morpholinopropyl)carbamate

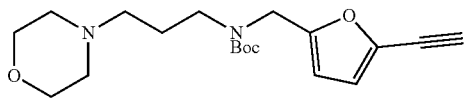 [SMILES: C#Cc1ccc(CN(CCCN2CCOCC2)C(=O)OC(C)(C)C)o1]

Tert-butyl 3-morpholinopropyl((5-((trimethylsilyl)ethynyl)furan-2-yl)methyl)carbamate (1.06 g, 2.52 mmol) was dissolved in methanol (30 mL). Anhydrous potassium carbonate (1.04 g, 7.52 mmol) was added. The mixture was stirred at room temperature for 8 hours, filtered by suction, and rotary-evaporated to dryness to remove the solvent and give a crude yellow solid (1.1 g).

(4) Preparation of (2S,3R)-methyl 2-(4-((5-((tert-butoxycarbonyl(3-morpholinopropyl)amino)methyl)furan-2-yl)buta-1,3-diynyl)benzamido)-3-hydroxybutanoate

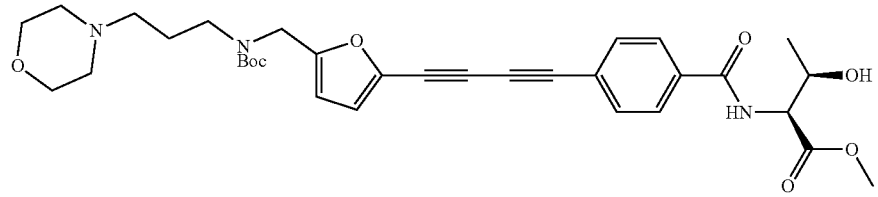 [SMILES: COC(=O)[C@@H](NC(=O)c1ccc(C#CC#Cc2ccc(CN(CCCN3CCOCC3)C(=O)OC(C)(C)C)o2)cc1)[C@@H](C)O]

Under an ice bath, cuprous chloride (2 mg) and hydroxylamine hydrochloride (4 mg) were respectively added to an aqueous butylamine solution (2 mL, 23%). Tert-butyl (5-ethynylfuran-2-yl)methyl(3-morpholinopropyl)carbamate (209 mg, 0.6 mmol) dissolved in an aqueous butylamine solution (2 mL, 23%) was added dropwisely to the reaction system, and then (2S,3R)-methyl 2-(4-(bromoethynyl)benzamido)-3-hydroxybutanoate (170 mg, 0.5 mmol) dissolved in a mixed solvent of an aqueous butylamine solution (1 mL), methanol (1 mL), and tetrahydrofuran (1 mL) was added dropwisely to the reaction system. The mixture was reacted for 1 minute. Water was added. The reaction mixture was extracted with ethyl acetate, rotary-evaporated to dryness, and purified by column chromatography (DCM:MeOH=20:1) to give a white solid (144 mg) in a yield of 47.4%.

(5) Preparation of N-((2S,3R)-3-hydroxy-1-(hydroxyamino)-1-oxobutan-2-yl)-4-((5-((3-morpholinopropylamino)methyl)furan-2-yl)buta-1,3-diynyl)benzamide

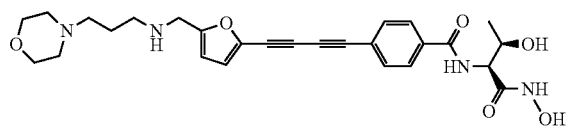

(2S,3R)-methyl 2-(4-((5-((tert-butoxycarbonyl(3-morpholinopropyl)amino)methyl)furan-2-yl)buta-1,3-diynyl)benzamido)-3-hydroxybutanoate (144 mg, 0.237 mmol) was dissolved in dichloromethane (4 mL). Trifluoroacetic acid (1 mL) was added. The mixture was reacted at room temperature for 4 hours, and rotary-evaporated to dryness. The product was directly used in the next step of the reaction.

The product from the above step was dissolved in anhydrous methanol (8 mL). An aqueous hydroxylamine solution (3 mL, 50%) was added. The mixture was reacted at room temperature for 3 hours and directly purified by preparative liquid phase chromatography to give Compound 22 (in a total of 20 mg) in a yield of 16.6%.

Molecular Formula: $C_{27}H_{32}N_4O_6$; Molecular Weight: 508.2; Mass Spectrum (M+H): 509.1

$^1$H-NMR (DMSO-$d_6$, 400 MHz) δ 10.65 (1H, s), 8.84 (1H, s), 8.19 (1H, d), 7.93 (2H, d), 7.71 (2H, d), 7.05 (1H, d), 6.39 (1H, d), 4.87 (1H, d), 4.24 (1H, dd), 4.05-3.95 (1H, m), 3.67 (2H, s), 3.54 (4H, t), 3.30-3.24 (2H, m), 2.35-2.20 (6H, m), 1.53 (2H, quintet), 1.07 (3H, d).

Example 19: Preparation of N-((2S,3R)-3-hydroxy-1-(hydroxyamino)-1-oxobutan-2-yl)-4-((5-(morpholinomethyl)furan-2-yl)buta-1,3-diynyl)benzamide (Compound 23)

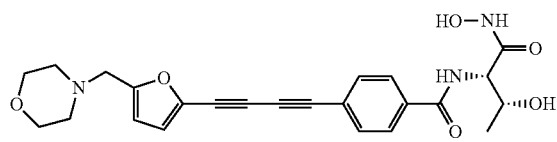 [SMILES: C[C@@H](O)[C@H](NC(=O)c1ccc(C#CC#Cc2ccc(CN3CCOCC3)o2)cc1)C(=O)NO]

With reference to Example 9, Compound 23 was synthesized.

Molecular Formula: $C_{24}H_{25}N_3O_6$; Molecular Weight: 451.2; Mass Spectrum: (M+H): 452.0

$^1$H-NMR ($d_6$-DMSO, 400 MHz) δ 10.67 (1H, s), 8.85 (1H, d), 8.20 (1H, d), 7.94 (2H, d), 7.72 (2H, d), 7.07 (1H, d), 6.47 (1H, d), 4.88 (1H, d), 4.24 (1H, dd), 4.08-3.95 (1H, m), 3.55 (4H, t), 3.53 (2H, s), 2.37 (4H, t), 1.07 (3H, d).

Example 20: Preparation of N-((2S,3R)-3-hydroxy-1-(hydroxyamino)-1-oxobutan-2-yl)-4-((5-(piperazin-1-ylmethyl)furan-2-yl)buta-1,3-diynyl)benzamide (Compound 24)

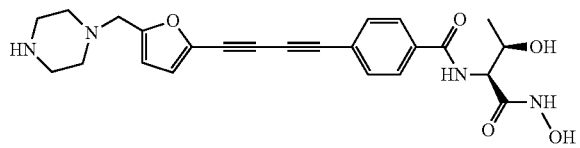 [SMILES: C[C@@H](O)[C@H](NC(=O)c1ccc(C#CC#Cc2ccc(CN3CCNCC3)o2)cc1)C(=O)NO]

With reference to Example 9, Compound 24 was synthesized.

Molecular Formula: $C_{24}H_{26}N_4O_5$; Molecular Weight: 450.2; Mass Spectrum (M+H): 451.0

$^1$H-NMR (DMSO-$d_6$, 400 MHz) δ 10.68 (1H, s), 8.85 (1H, s), 8.20 (1H, d), 7.94 (2H, d), 7.72 (2H, d), 7.06 (1H, d), 6.44 (1H, d), 4.88 (1H, d), 4.24 (1H, dd), 4.05-3.95 (1H, m), 3.49 (2H, s), 2.69 (4H, t), 2.04-1.92 (4H, m), 1.07 (3H, d).

Example 21: Preparation of 4-(3-(furan-2-yl)acrylamido)-N-((2S,3R)-3-hydroxy-1-(hydroxyamino)-1-oxobutan-2-yl)-benzamide (Compound 30)

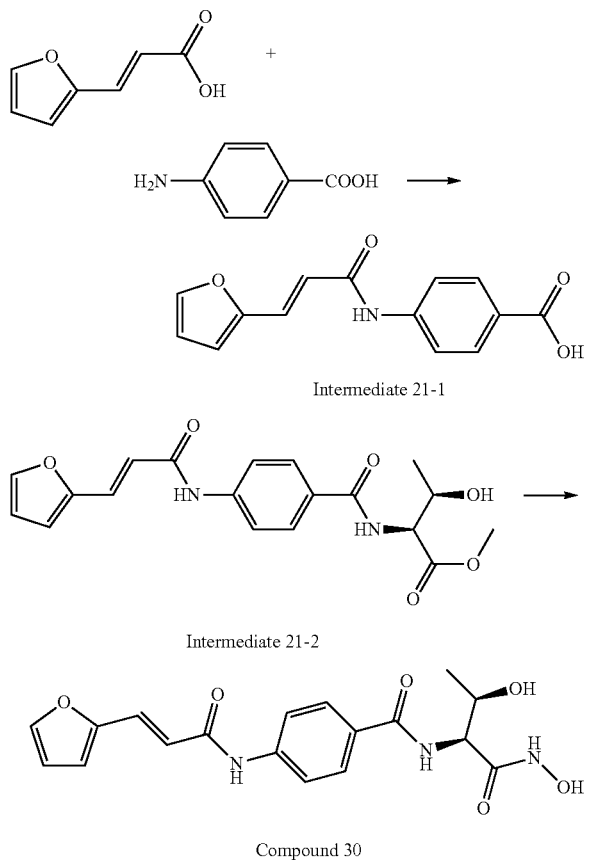

(1) Preparation of Intermediate 21-1

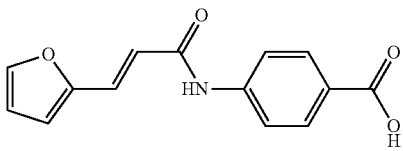 [SMILES: O=C(/C=C/c1ccco1)Nc1ccc(C(=O)O)cc1]

2-furanylacrylic acid (2.762 g, 20 mmol) was dissolved in dichloromethane (30 mL). Thionyl chloride (2.379 g, 20 mmol) was added. The mixture was stirred at 25° C. for 1 hour. Para-aminobenzoic acid (2.743 g, 20 mmol) was added. The mixture was warmed to 35° C. and reacted for 72 hours. In the post-treatment, the reaction system was rotary-evaporated to dryness and purified by column chromatography (PE:EA=2:1) to give Intermediate 21-1 (514 mg).

(2) Preparation of Intermediate 21-2

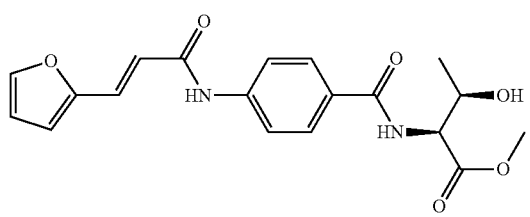 [SMILES: COC(=O)[C@@H](NC(=O)c1ccc(NC(=O)/C=C/c2ccco2)cc1)[C@@H](C)O]

Intermediate 21-1 (514 mg, 2 mmol) and L-threonine methyl ester hydrochloride (339 mg, 2 mmol) were dissolved in DMF (4 mL). DIEA (517 g, 4 mmol) was added. The solution was stirred for 50 minutes. After the solution became clear, HOBt (270 mg, 2 mmol) and EDCI (383 mg, 2 mmol) were added. The mixture was reacted under stirring for 15 hours. In the post-treatment, the reaction system was poured into water. The mixture was extracted with ethyl acetate and separated into phases. The organic phase was dried, rotary-evaporated to dryness to give a crude product (800 mg), which was purified by column chromatography (PE:EA=1:2) to give Intermediate 21-2 (200 mg).

(3) Preparation of 4-(3-(furan-2-yl)acrylamido)-N-((2S,3R)-3-hydroxy-1-(hydroxyamino)-1-oxobutan-2-yl)-benzamide (Compound 30)

Intermediate 21-2 (150 mg, 0.403 mmol) was dissolved in methanol (4 mL). An aqueous hydroxylamine solution (50%, 2 mL) was added. The mixture was reacted under stirring for 40 hours. In the post-treatment, the reaction system was poured into water. The mixture was filtered by suction. The filter cake was washed with water and dried to give Compound 30 (74 mg).

Molecular Formula: $C_{18}H_{19}N_3O_6$; Molecular Weight: 373.36; Mass Spectrum: (M+H): 374.0

$^1$H-NMR ($d_6$-DMSO, 800 MHz) δ 10.62 (1H, s), 10.1 (1H, s), 8.81 (1H, s), 7.83 (4H, d), 7.74 (2H, d), 7.40 (1H, d), 6.86 (1H, s), 6.62 (2H, d), 4.87 (1H, d), 4.23 (1H, d), 4.01 (1H, d), 1.10 (3H, d).

Example 22: Preparation of 4-(2-(furan-2-methylene)hydrazinecarbonyl)-N-((2S,3R)-3-hydroxy-1-(hydroxyamino)-1-oxobutan-2-yl)-benzamide (Compound 26)

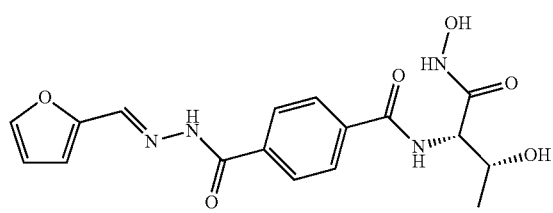 [SMILES: C[C@@H](O)[C@H](NC(=O)c1ccc(C(=O)N/N=C/c2ccco2)cc1)C(=O)NO]

With reference to Example 21, Compound 26 was synthesized.

Molecular Formula: $C_{17}H_{18}N_4O_6$; Molecular Weight: 374.1; Mass Spectrum: (M+H): 375.0

$^1$H-NMR (DMSO-$d_6$, 800 MHz): δ 11.89 (1H, s), 8.43 (1H, s), 8.34 (1H, s), 7.99 (4H, s), 7.85 (1H, s), 6.94 (1H, s), 6.93 (1H, s), 4.99 (1H, s), 4.50 (1H, s), 4.17 (1H, s), 3.64 (1H, s), 1.13 (4H, d)

Example 23: Preparation of 5-{4-[N-((2S,3R)-3-hydroxy-1-(hydroxyamino)-1-oxobutan-2-yl)carbamoyl)-phenyl]-buta-1,3-diynyl}-furan-2-carboxamide (Compound 27)

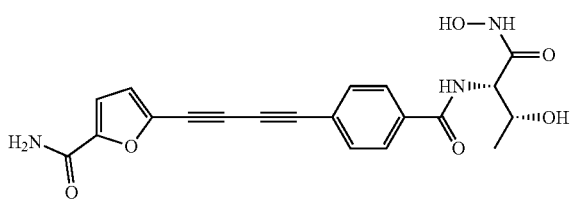 [SMILES: C[C@@H](O)[C@H](NC(=O)c1ccc(C#CC#Cc2ccc(C(N)=O)o2)cc1)C(=O)NO]

With reference to the above Example 4, Compound 27 was synthesized.

Molecular Formula: $C_{20}H_{17}N_3O_6$; Molecular Weight: 395.37; Mass Spectrum: (M+H): 396.0

$^1$H-NMR ($d_6$-DMSO, 800 MHz) δ 10.69 (1H, s), 8.87 (1H, s), 8.25 (1H, d), 8.0 (1H, s), 7.97 (2H, d), 7.77 (2H, d), 7.76 (1H, s), 7.22 (1H, q), 4.89 (1H, d), 4.25 (1H, t), 4.03 (1H, q), 1.09 (3H, t).

Example 24: Preparation of 5-{4-[N-((2S,3R)-3-hydroxy-1-(hydroxyamino)-1-oxobutan-2-yl)carbamoyl)-phenyl]-buta-1,3-diynyl}-furan-2-carboxylic Acid Dimethylamide (Compound 29)

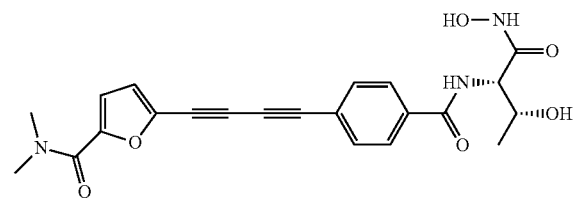 [SMILES: C[C@@H](O)[C@H](NC(=O)c1ccc(C#CC#Cc2ccc(C(=O)N(C)C)o2)cc1)C(=O)NO]

With reference to the above Example 4, Compound 29 was synthesized.

Molecular Formula: $C_{22}H_{21}N_3O_6$; Molecular Weight: 423.42; Mass Spectrum: (M+H): 424.1

$^1$H-NMR ($d_6$-DMSO, 800 MHz) δ 10.69 (1H, s), 8.87 (1H, s), 8.25 (1H, d), 7.96 (2H, d), 7.76 (2H, d), 7.25 (1H, d), 7.12 (1H, d), 4.89 (1H, d), 4.25 (1H, t), 4.03 (1H, q), 3.19 (3H, s), 2.98 (3H, s), 1.09 (3H, d).

Example 25: Preparation of 4-((1E,3E)-4-(furan-3-yl)buta-1,3-dienyl)-N-((2S,3R)-3-hydroxy-1-(hydroxyamino)-1-oxobutan-2-yl)benzamide (Compound 31)

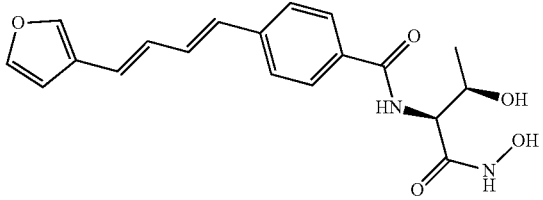 [SMILES: C[C@@H](O)[C@H](NC(=O)c1ccc(/C=C/C=C/c2ccoc2)cc1)C(=O)NO]

With reference to the above Example 1, Compound 31 was synthesized.

Molecular Formula: $C_{19}H_{20}N_2O_5$; Molecular Weight: 356.37; Mass Spectrum: (M+H): 357.0

$^1$H-NMR ($d_6$-DMSO, 800 MHz) δ 10.66 (1H, s), 8.85 (1H, d), 7.98 (1H, d), 7.90-7.85 (3H, m), 7.68 (1H, d), 7.58 (2H, d), 7.22-7.14 (1H, m), 6.84-6.78 (2H, m), 6.71-6.66 (2H, m), 4.89 (1H, d), 4.27 (1H, t), 4.06-4.0 (1H, m), 1.17 (3H, d).

Example 26: Preparation of N-((2S,3R)-3-hydroxy-1-(hydroxyamino)-1-oxobutan-2-yl)-6-((1E,3E)-4-((5-(hydroxymethyl)-furan-2-yl)buta-1,3-dienyl) nicotinamide (Compound 32)

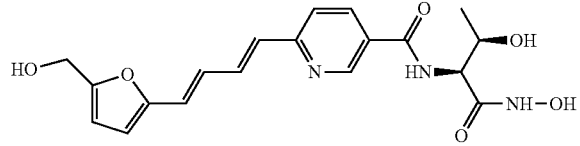 [SMILES: C[C@@H](O)[C@H](NC(=O)c1ccc(/C=C/C=C/c2ccc(CO)o2)nc1)C(=O)NO]

With reference to the above Example 1, Compound 32 was synthesized.

91
Molecular Formula: $C_{20}H_{220}N_2O_6$; Molecular Weight: 386.40; Mass Spectrum: (M+H): 387.1
$^1$H-NMR ($d_6$-DMSO, 800 MHz) δ 10.65 (1H, s), 8.99 (1H, d), 8.88 (1H, s), 8.30-8.20 (2H, m), 7.58-7.25 (1H, m), 6.86-6.79 (3H, m), 6.64 (1H, d), 6.49 (1H, d), 6.38 (1H, d),
92
5.31-5.28 (1H, m), 4.89 (1H, s), 4.3 (2H, s), 4.31-4.26 (1H, m), 4.06-4.03 (1H, m), 1.10 (3H, d).
Example 27: Preparation of N-((2S,3R)-3-hydroxy-1-(hydroxamino)-1-oxobutan-2-yl)-4-((5-(hydroxymethyl)-1-methyl-1H-pyrrol-2-yl)buta-1,3-diynyl)benzamide (Compound 33)
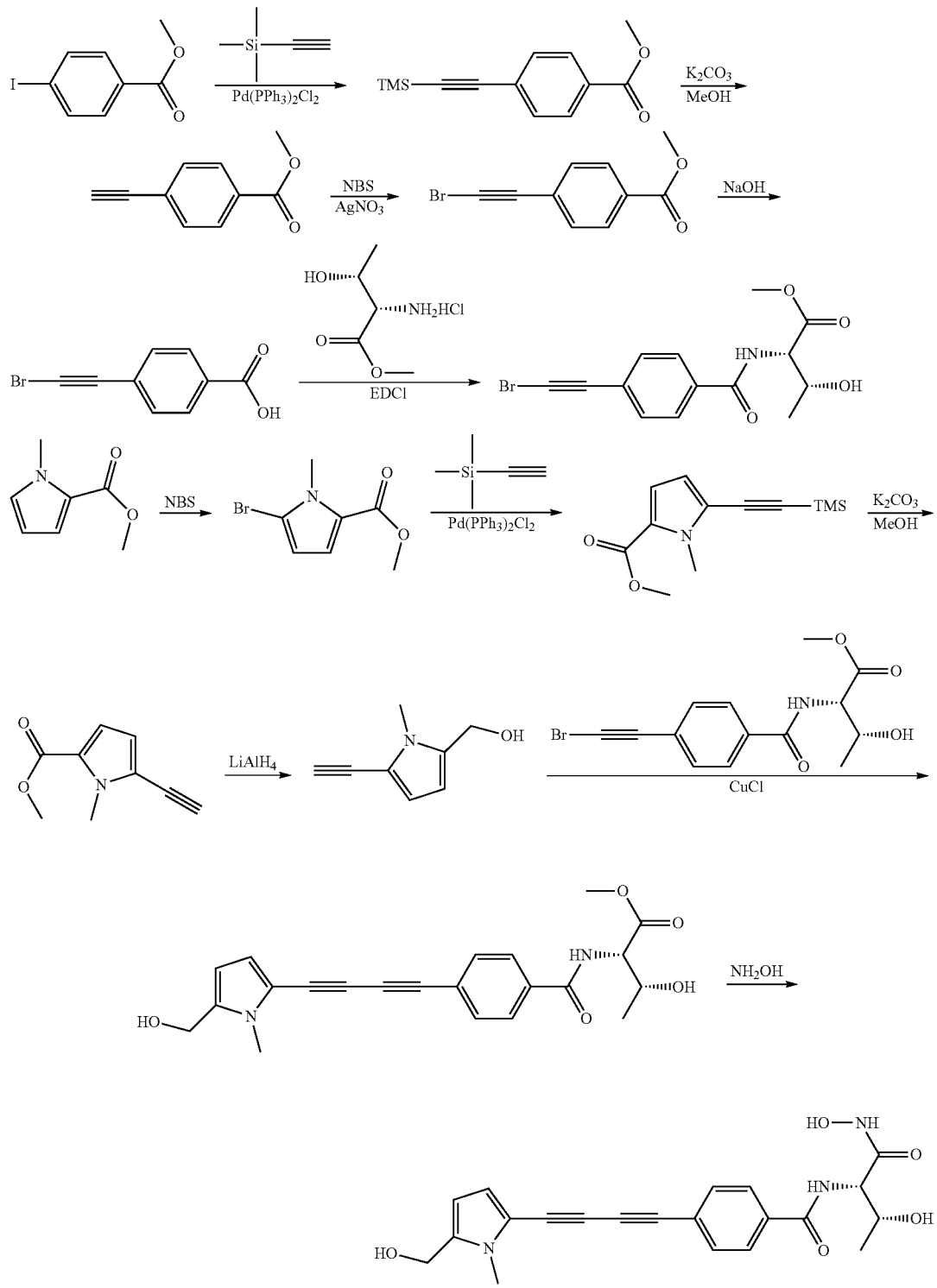

(1) Preparation of methyl 4-((trimethylsilyl)ethynyl)benzoate

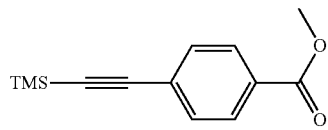 [SMILES: COC(=O)c1ccc(C#C[Si](C)(C)C)cc1]

Methyl 4-iodobenzoate (8.00 g, 30.5 mmol), trimethylsilylethyne (2.995 g, 30.5 mmol), triethylamine (7.09 g, 70.1 mmol), Pd(PPh$_3$)$_2$Cl$_2$ (0.214 g, 0.305 mmol) and CuI (0.057 g, 0.299 mmol) were dissolved in THF (60 mL). The atmosphere was replaced with nitrogen gas three times. The mixture was stirred at normal temperature for 18 hours, rotary-evaporated to dryness, and purified by silica column chromatography (100% petroleum ether→petroleum ether:ethyl acetate=1:2) to give a red solid (6.3 g) in a yield of 88.9%.

(2) Preparation of methyl 4-ethynylbenzoate

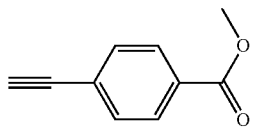

Methyl 4-((trimethylsilyl)ethynyl)benzoate (2.10 g, 9.04 mmol) was dissolved in methanol (30 mL). K$_2$CO$_3$ (2.50 g, 18.1 mmol) was added. The mixture was reacted under stirring for 2 hours, and rotary-evaporated to dryness. Ethyl acetate (30 mL) and water (30 mL) were added. The mixture was extracted. The organic phase was dried over anhydrous sodium sulphate, and rotary-evaporated to dryness to give a yellow solid (1.45 g) in a yield of 100%.

(3) Preparation of methyl 4-(bromoethynyl)benzoate

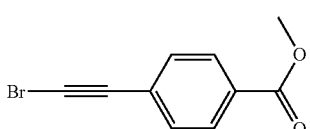

Methyl 4-ethynylbenzoate (1.00 g, 6.24 mmol) was dissolved in acetone (50 mL). Silver nitrate (0.10 g, 0.589 mmol) was added. The mixture was stirred for 40 minutes. NBS (1.237 g, 6.95 mmol) was added. The resulting solution was stirred at room temperature for 2 hours and filtered. The filtrated was rotary-evaporated to dryness and crystallized in isopropanol to give a white solid (1.23 g) in a yield of 82.4%.

(4) Preparation of 4-(bromoethynyl)benzoic Acid

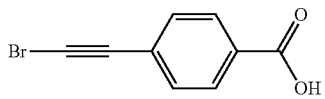

Methyl 4-(bromoethynyl)benzoate (1.23 g, 5.14 mmol) was dissolved in methanol (9 mL) and water (1 mL). NaOH (0.413 g, 10.3 mmol) was added. The mixture was reacted under stirring for 2 hours. Water (15 mL) was added. The mixture was adjusted with a diluted hydrochloric acid (1N) to a pH value of 6 and filtered to give a white solid (0.87 g) in a yield of 75.3%.

(5) Preparation of (2S,3R)-methyl 2-(4-(bromoethynyl)benzamido)-3-hydroxybutanoate

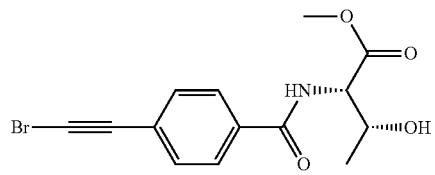 [SMILES: COC(=O)[C@@H](NC(=O)c1ccc(C#CBr)cc1)[C@@H](C)O]

4-(bromoethynyl)benzoic acid (0.87 g, 3.87 mmol), and L-threonine methyl ester hydrochloride (0.693 g, 4.09 mmol) were dissolved in DMF (10 mL). DIEA (0.957 g, 7.41 mmol) was added. The solution was stirred for 30 minutes. After the solution became clear, HOBt (0.552 g, 4.09 mmol) and EDCI (0.784 g, 4.09 mmol) were added. The mixture was reacted under stirring for 15 hours. Ethyl acetate (30 mL) and water (30 mL) were added. The mixture was extracted. The resulting organic phase was dried over anhydrous sodium sulphate, rotary-evaporated to dryness, and purified by silica column chromatography (100% petroleum ether→petroleum ether:ethyl acetate=1:1) to give a white solid (1.21 g) in a yield of 92%.

(6) Preparation of methyl 5-bromo-1-methyl-H-pyrrole-2-carboxylate

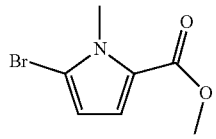

Methyl 1-methylpyrrole-2-carboxylate (3.0 g, 21.6 mmol) and NBS (3.84 g, 21.6 mmol) were dissolved in dichloromethane (40 mL). The mixture was reacted in the dark for 12 hours, rotary-evaporated to dryness, purified with silica gel column (petroleum ether) to give a product (2.21 g) in a yield of 46.8%.

(7) Preparation of methyl 1-methyl-5-((trimethylsilyl)ethynyl)-1H-pyrrole-2-carboxylate

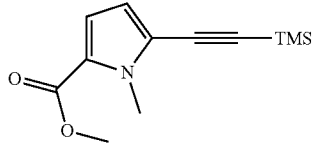 [SMILES: COC(=O)c1ccc(C#C[Si](C)(C)C)n1C]

Methyl 5-bromo-1-methyl-1H-pyrrole-2-carboxylate (2.00 g, 9.17 mmol), trimethylsilylethyne (1.08 g, 11.0 mmol), triethylamine (1.86 g, 18.4 mmol), Pd(PPh$_3$)$_2$Cl$_2$ (45 mg, 0.064 mmol) and CuI(4 mg, 0.018 mmol) were dissolved in THF (20 mL). The atmosphere was replaced with nitrogen gas three times. The mixture was heated to 90° C. and stirred for 18 hours, rotary-evaporated to dryness, and purified by silica column chromatography (100% petroleum ether→petroleum ether:ethyl acetate=5:1) to give a pale red solid (1.92 g) in a yield of 89%.

(8) Preparation of methyl 5-ethynyl-1-methyl-H-pyrrole-2-carboxylate

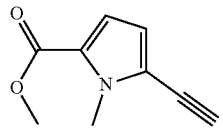

Methyl 1-methyl-5-((trimethylsilyl)ethynyl)-1H-pyrrole-2-carboxylate (1.90 g, 8.07 mmol) was dissolved in methanol (30 mL). K$_2$CO$_3$ (2.23 g, 16.2 mmol) was added. The mixture was reacted under stirring for 2 hours, and rotary-evaporated to dryness. Ethyl acetate and water (30 mL) were added. The mixture was extracted. The organic phase was dried over anhydrous sodium sulphate, and rotary-evaporated to dryness to give a yellow solid (1.32 g) in a yield of 100.0%.

(9) Preparation of (5-ethynyl-1-methyl-H-pyrrol-2-yl)methanol

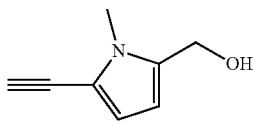

Methyl 5-ethynyl-1-methyl-1H-pyrrole-2-carboxylate (1.05 g, 6.43 mmol) was dissolved in anhydrous THF (20 mL). LiAlH$_4$ (0.367 g, 9.66 mmol) was slowly added at 0° C. The mixture was reacted at normal temperature under stirring for 7 hours and cooled to 0° C. Ethyl acetate was added until no bubbles were generated in the reaction solution. Water (2 mL) was added. The mixture was filtered by suction. The filtrate was extracted with ethyl acetate and washed with water (20 mL). The organic phase was dried over anhydrous sodium sulphate, rotary-evaporated to dryness, and purified by silica column chromatography (100% petroleum ether→petroleum ether:ethyl acetate=2:1) to give a red solid (0.67 g) in a yield of 77.1%.

(10) Preparation of (2S,3R)-methyl 3-hydroxy-2-(4-((5-(hydroxymethyl)-1-methyl-H-pyrrol-2-yl)buta-1,3-diynyl)benzamidobutanoate

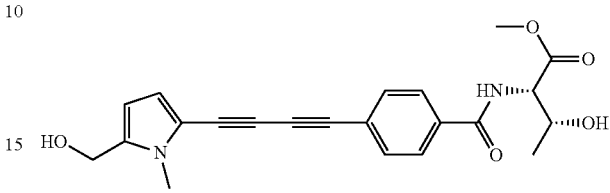

CuCl (3 mg, 0.03 mmol) and hydroxylamine hydrochloride (6 mg, 0.09 mmol) were dissolved in an aqueous n-butylamine solution (10 mL, 23%). A solution of (5-ethynyl-1-methyl-1H-pyrrol-2-yl)methanol (0.217 g, 1.60 mmol) in methanol and tetrahydrofuran (5 mL, V:V, 1:1), and a solution of (2S,3R)-methyl 2-(4-(bromoethynyl)benzamido)-3-hydroxybutanoate (0.496 g, 1.46 mmol) in methanol and tetrahydrofuran (5 mL, V:V, 1:1) were successively added to the above reaction solution. The mixture was stirred for 2 minutes. Ethyl acetate (20 mL) and water (20 mL) were added. The mixture was extracted. The organic phase was dried over anhydrous sodium sulphate, rotary-evaporated to dryness, and purified by silica column chromatography (100% petroleum ether→petroleum ether:ethyl acetate=2:1) to give a pale-red solid (0.54 g) in a yield of 93.8%.

(11) Preparation of N-((2S,3R)-3-hydroxy-1-(hydroxyamino)-1-oxobutan-2-yl)-4-((5-(hydroxymethyl)-1-methyl-1H-pyrrol-2-yl)buta-1,3-diynyl)benzamide

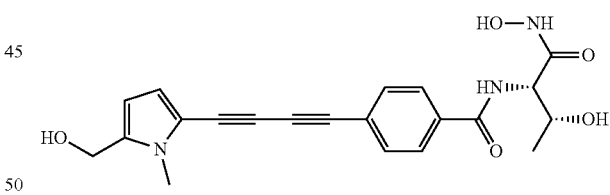

(2S,3R)-methyl 3-hydroxy-2-(4-((5-(hydroxymethyl)-1-methyl-1H-pyrrol-2-yl)buta-1,3-diynyl)benzamidobutanoate (0.50 g, 1.27 mmol) was dissolved in methanol (10 mL). An aqueous hydroxylamine solution (50%, 2 mL) and lithium hydroxide monohydrate (0.018 g, 0.43 mmol) were added. The mixture was reacted under stirring for 48 hours, rotary-evaporated to dryness, and purified by preparative liquid phase chromatography to give Compound 33 (0.178 g) in a yield of 35.4%

Molecular Formula: C$_{21}$H$_{21}$N$_3$O$_5$; Molecular Weight: 395.1; Mass Spectrum: (M+H): 396.1, $^1$H-NMR (d$_6$-DMSO, 400 MHz) δ 10.66 (1H, s), 8.83 (1H, s), 8.16 (1H, d), 7.92 (2H, d), 7.68 (2H, d), 6.57 (1H, d), 6.02 (1H, d), 5.12 (1H, t), 4.89 (1H, br s), 4.41 (2H, d), 4.24 (1H, dd), 4.01 (1H, t), 3.63 (3H, s), 1.07 (3H, d).

Example 28: Preparation of N-((2S,3R)-3-hydroxy-1-(hydroxamino)-1-oxobutan-2-yl)-4-((1-methyl-1H-pyrazol-5-yl)buta-1,3-diynyl)benzamide (Compound 34)

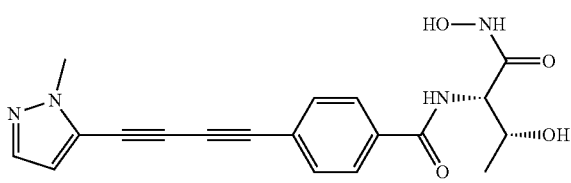 [SMILES: C[C@@H](O)[C@H](NC(=O)c1ccc(C#CC#Cc2ccnn2C)cc1)C(=O)NO]

With reference to Example 28, Compound 34 was synthesized.

Molecular Formula: $C_{19}H_{18}N_4O_4$; Molecular Weight: 366.1; Mass Spectrum (M+H): 367.1

$^1$H-NMR (d$_6$-DMSO, 400 MHz) δ 10.69 (1H, s), 8.85 (1H, s), 8.23 (1H, d), 7.97 (2H, d), 7.76 (2H, d), 7.56 (1H, d), 6.79 (1H, d), 4.92 (1H, m), 4.26 (1H, d), 4.03 (1H, m), 3.94 (3H, s), 1.09 (3H, d).

Example 29: Preparation of 4-((6-(furan-2-yl)pyridin-3-yl)ethynyl)-N-((2S,3R)-3-hydroxy-1-(hydroxyamino)-1-oxobutan-2-yl)benzamide (Compound 35)

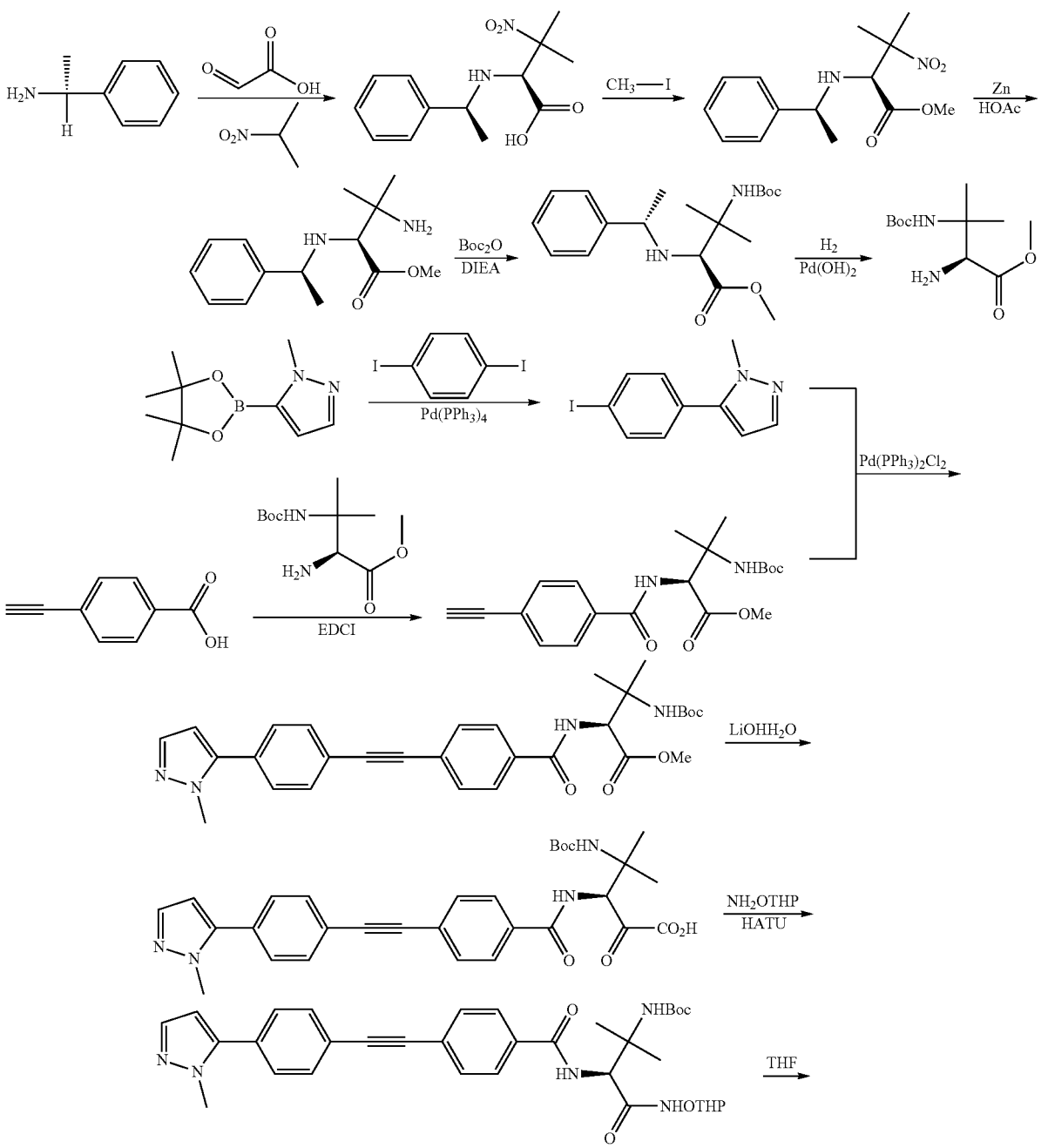

-continued

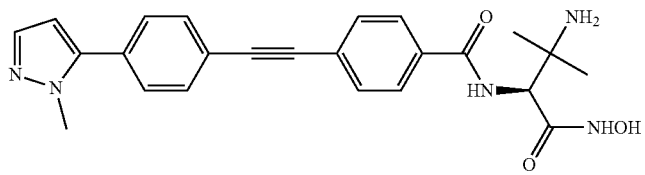

(1) Preparation of (S)-3-methyl-3-nitro-2-((S)-1-phenylethylamino)butanoic Acid

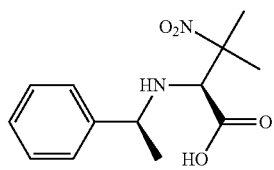 [SMILES: C[C@H](N[C@H](C(=O)O)C(C)(C)[N+](=O)[O-])c1ccccc1]

2-nitropropane (18.5 mL, 0.206 mol) and potassium hydroxide (13.6 g, 0.242 mol) were dissolved in water (200 mL). In the nitrogen protection, the mixture was heated to 45° C. S-1-phenylethylamine (25 g, 0.206 mol) was quickly added, and then an aqueous glyoxylic acid solution (50%, 29.92 g) was slowly added dropwisely. After the dropwise addition, the mixture was stirred at 35° C. for 3 hours, and then a diluted hydrochloric acid (3M, 152 mL, 0.456 mol) was slowly added dropwisely thereto. The mixture was stirred at room temperature overnight. A white precipitate was formed. The mixture was filtered by suction. The solid was washed successively with a diluted hydrochloric acid (0.2 M, 0.5 L), water (0.5 L), and diethylether (0.125 L), and dried to give a white powder solid (27.43 g) in a yield of 50%.

(2) Preparation of (S)-methyl 3-methyl-3-nitro-2-((S)-1-phenylethylamino)butanoate

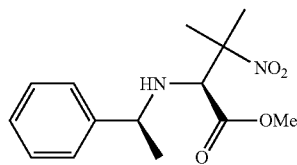 [SMILES: COC(=O)[C@@H](N[C@@H](C)c1ccccc1)C(C)(C)[N+](=O)[O-]]

(S)-3-methyl-3-nitro-2-((S)-1-phenylethylamino)butanoic acid (25 g, 93.9 mmol) and cesium carbonate (33.6 g, 103 mmol) were added to N,N-dimethylformamide (100 mL). In the nitrogen protection, to the resulting mixture indomethane (15.32 g, 108 mmol) was added dropwisely at 0° C. After the dropwise addition, the mixture was transferred to room temperature and reacted for 12 hours. The reaction mixture was poured into water, and adjusted with a diluted hydrochloric acid to a pH value of about 7-8. The reaction mixture was extracted with ethyl acetate, dried over anhydrous sodium sulphate, and concentrated to give an oily substance (26.3 g), which was directly used in the next step without purification.

(3) Preparation of (S)-methyl 3-amino-3-methyl-2-((S)-1-phenylethylamino)butanoate

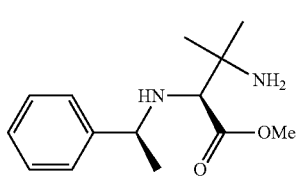 [SMILES: COC(=O)[C@@H](N[C@@H](C)c1ccccc1)C(C)(C)N]

The crude product obtained in the previous step (26.3 g, about 93.9 mmol) was dissolved in tetrahydrofuran (100 mL) and glacial acetic acid (150 mL). Zinc powder (in a total of 55.3 g, 845 mmol) was added in batch to the above mixture under an ice-bath. Then the resulting mixture was transferred to room temperature and reacted for 18 hours. The mixture was filtered by suction. The filter cake was washed with tetrahydrofuran. The filtrate was concentrated and water was added. The resulting mixture was adjusted with saturated sodium bicarbonate to a pH value of about 9-10, extracted with dichloromethane, dried over anhydrous sodium sulphate, and concentrated to give an oily substance (23.5 g), which was directly used in the next step without purification.

(4) Preparation of (S)-methyl 3-(tert-butoxycarbonylamino)-3-methyl-2-((S)-1-phenylethylamino)butanoate

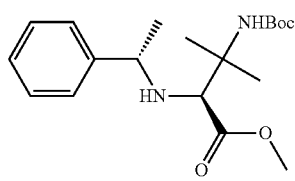 [SMILES: COC(=O)[C@@H](N[C@@H](C)c1ccccc1)C(C)(C)NC(=O)OC(C)(C)C]

The crude product obtained in the previous step (23.5 g), diisopropylethylamine (24.3 g, 188 mmol) and Boc-anhydride (22.5 g, 103 mmol) were dissolved in tetrahydrofuran (150 mL). The mixture was stirred at room temperature for 16 hours, concentrated, dissolved in ethyl acetate, washed successively with 10% citric acid and a semi-saturated sodium bicarbonate solution, washed with brine, dried over anhydrous sodium sulphate, concentrated, and purified by silica column chromatography (petroleum ether:ethyl acetate=5:1) to give a clear oily substance (13.2 g).

(5) Preparation of (S)-methyl 2-amino-3-(tert-butoxycarbonylamino)-3-methylbutanoate

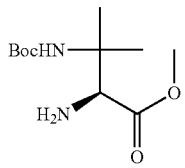

(S)-methyl 3-(tert-butoxycarbonylamino)-3-methyl-2-((S)-1-phenylethylamino)butanoate (5.2 g, 14.8 mmol) was dissolved in tetrahydrofuran (150 mL). Palladium hydroxide/carbon (20%, 1.8 g) was added. The mixture was reacted in a hydrogen gas atmosphere for 4 hours. The reaction mixture was filtered by suction. The filtrate was concentrated and purified by silica column chromatography (dichloromethane:methanol=10:1) to give a product (3.35 g) in a yield of 91.9%.

(6) Preparation of 5-(4-iodophenyl)-1-methyl-H-pyrazole

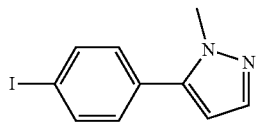

1-methyl-5-(4,4,5,5-tetramethyl-1,3,2-dioxaborolan-2-yl)-1H-pyrazole (833 mg, 4.0 mmol), para-diiodobenzene (1.497 g, 4.54 mmol), tetrakis(triphenylphosphine)palladium (462 mg, 0.4 mmol) and sodium carbonate (636 mg, 6.0 mmol) were dissolved in 1,4-dioxane (30 mL) and water (10 mL). In the nitrogen protection, the mixture was reacted at 90° C. for 6 hours, cooled, concentrated, and purified by silica column chromatography (petroleum ether:ethyl acetate=5:1) to give a white solid (633 mg) in a yield of 55.8%.

(7) Preparation of (S)-methyl 3-(tert-butoxycarbonylamino)-2-(4-ethynylbenzamido)-3-methylbutanoate

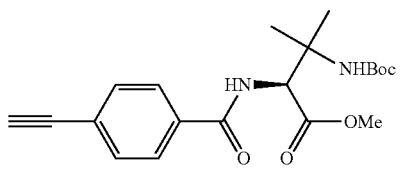 [SMILES: C#Cc1ccc(C(=O)N[C@H](C(=O)OC)C(C)(C)NC(=O)OC(C)(C)C)cc1]

(2S,3R)-methyl 3-hydroxy-2-(4-ethynylbenzamido)butanoate (439 mg, 3.0 mmol), (S)-methyl 2-amino-3-(tert-butoxycarbonylamino)-3-methylbutanoate (887 mg, 3.6 mmol), EDCI (691 mg, 3.6 mmol), HOBt (487 mg, 3.6 mmol) and N,N-diisopropylethylamine (1.55 g, 12.0 mmol) were dissolved in N,N-dimethylacetamide (30 mL). The mixture was reacted at room temperature for 12 hours. The reaction mixture was poured into water, and extracted with ethyl acetate. The organic phase was concentrated and purified by silica column chromatography (petroleum ether:ethyl acetate=3:1) to give a yellow solid (1.1 g) in a yield of 98%.

(8) Preparation of (S)-methyl 3-(tert-butoxycarbonylamino)-3-methyl-2-(4-((4-(1-methyl-1H-pyrazol-5-yl)phenyl)ethynyl)benzamido)butanoate

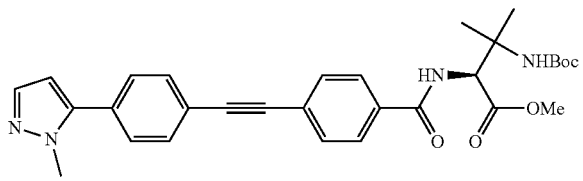 [SMILES: COC(=O)[C@@H](NC(=O)c1ccc(C#Cc2ccc(-c3ccnn3C)cc2)cc1)C(C)(C)NC(=O)OC(C)(C)C]

5-(4-iodophenyl)-1-methyl-1H-pyrazole (396 mg, 1.39 mmol), (S)-methyl 3-(tert-butoxycarbonylamino)-2-(4-ethynylbenzamido)-3-methylbutanoate (522 mg, 1.39 mmol), bis(triphenylphosphine)palladium dichloride (20 mg, 0.028 mmol), cuprous iodide (3 mg, 0.016 mmol) and triethylamine (423 mg, 4.18 mmol) were dissolved in acetonitrile (30 mL). Under the nitrogen protection, the mixture was reacted at room temperature for 3 hours, concentrated, and purified by silica column chromatography (petroleum ether:ethyl acetate=2:1) to give a white solid (689 mg) in a yield of 93.4%.

(9) Preparation of (S)-3-(tert-butoxycarbonylamino)-3-methyl-2-(4-((4-(1-methyl-H-pyrazol-5-yl)phenyl)ethynyl)benzamido)butanoic Acid

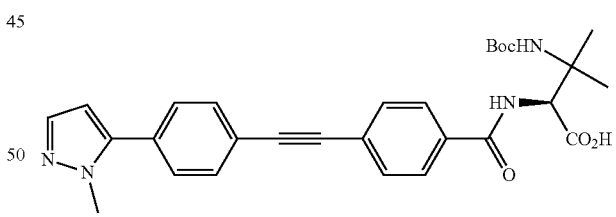

(S)-methyl 3-(tert-butoxycarbonylamino)-3-methyl-2-(4-((4-(1-methyl-1H-pyrazol-5-yl)phenyl)ethynyl)benzamido)butanoate (354 mg, 0.667 mmol) and lithium hydroxide monohydrate (84 mg, 2.0 mmol) were dissolved in a solvent mixture of tetrahydrofuran and water (30 mL, v/v=4:1). The mixture was reacted at room temperature for 8 hours. The reaction mixture was adjusted with a diluted hydrochloric acid to a pH value of 6 under an ice-water bath, and a solid was separated. The mixture was filtered to give a white solid (317 mg) in a yield of 92.1%.

(10) Preparation of (3S)-tert-butyl 2-methyl-3-(4-((4-(1-methyl-1H-pyrazol-5-yl)phenyl)ethynyl)benzamido)-4-oxo-4-(tetrahydro-2H-pyran-2-yloxyamino)butan-2-ylcarbamate

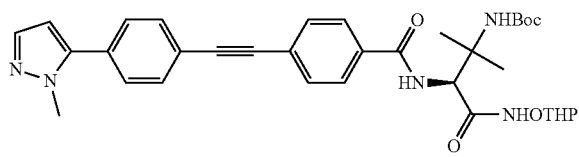

(S)-3-(tert-butoxycarbonylamino)-3-methyl-2-(4-((4-(1-methyl-1H-pyrazol-5-yl)phenyl)ethynyl)benzamido)butanoic acid (317 mg, 0.614 mmol), O-(tetrahydro-2H-pyran-2-yl)hydroxylamine (144 mg, 1.23 mmol), HATU(350 mg, 0.920 mmol) and triethylamine (187 mg, 1.84 mmol) were dissolved in DMA(30 mL). The mixture was stirred at room temperature for 6 hours and poured into water. The resulting mixture was extracted with ethyl acetate. The organic phase was concentrated and then purified by silica column chromatography (petroleum ether:ethyl acetate=1:1) to give a yellow solid (105 mg) in a yield of 27.9%.

(11) Preparation of (S)—N-(3-amino-1-(hydroxyamino)-3-methyl-1-oxobutan-2-yl)-4-((4-(1-methyl-1H-pyrazol-5-yl)phenyl)ethynyl)benzamide

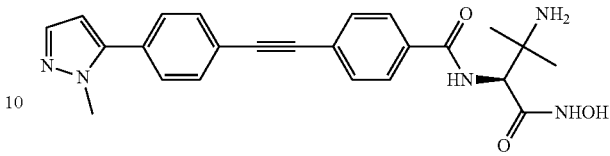

(3S)-tert-butyl 2-methyl-3-(4-((4-(1-methyl-1H-pyrazol-5-yl)phenyl)ethynyl)benzamido)-4-oxo-4-(tetrahydro-2H-pyran-2-yloxyamino)butan-2-ylcarbamate (105 mg, 0.171 mmol) was dissolved in dichloromethane (20 mL). In an ice bath, trifluoroacetic acid (5 mL) was added dropwisely. The mixture was reacted at room temperature for 2 hours, concentrated and then purified by preparative liquid phase chromatography to give a white solid (25 mg) in a yield of 33.9%.

Molecular Formula: $C_{24}H_{25}N_5O_3$; Molecular Weight: 431.2; Mass Spectrum (M+H): 432.1

$^1$H-NMR (d$_6$-DMSO, 400 MHz) δ 8.42-8.25 (3H, m), 7.93 (2H, d), 7.74-7.65 (4H, m), 7.62 (2H, d), 7.48 (1H, d), 6.49 (1H, d), 4.35 (1H, s), 3.89 (3H, s), 1.13 (3H, s), 1.05 (3H, s).

Example 30: Preparation of N-((2S,3R)-3-hydroxy-1-(hydroxyamino)-1-oxobutan-2-yl)-4-((4-(1-methyl-1H-pyrazol-5-yl)phenyl)ethynyl)benzamide (Compound 36)

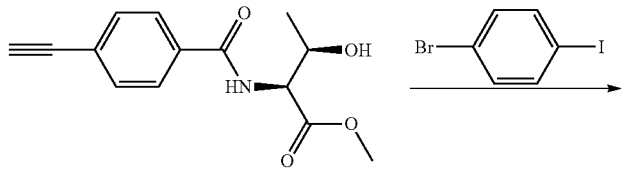

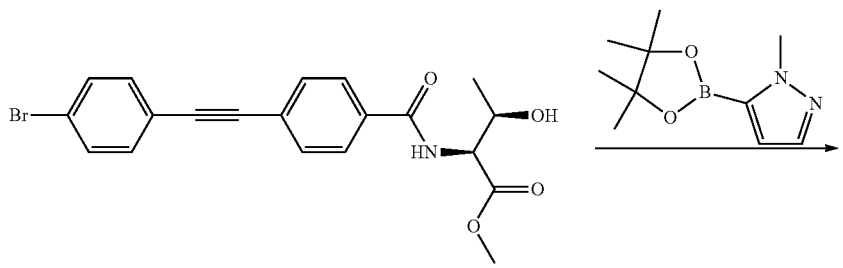

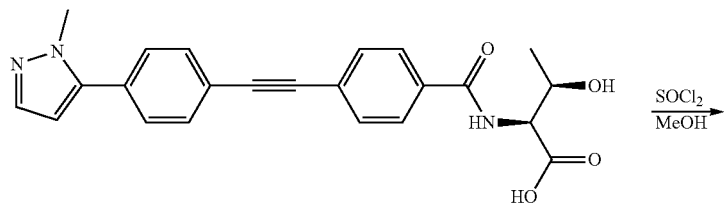

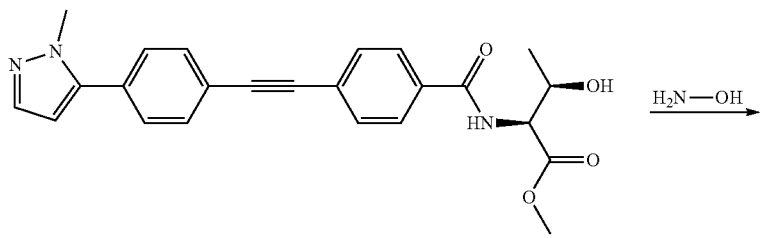

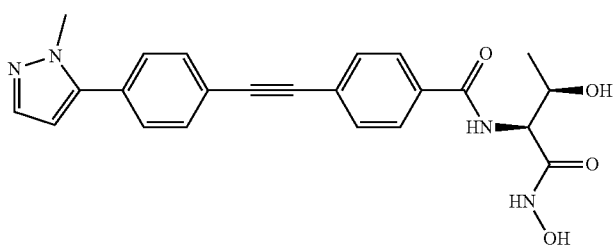

(1) Preparation of (2S,3R)-methyl 2-(4-((4-bromophenyl)ethynyl)benzamido)-3-hydroxybutanoate

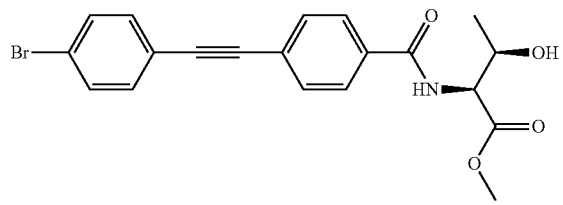 [SMILES: COC(=O)[C@@H](NC(=O)c1ccc(C#Cc2ccc(Br)cc2)cc1)[C@@H](C)O]

(2S,3R)-methyl 2-(4-ethynylbenzamido)-3-hydroxybutanoate (1.00 g, 3.83 mmol), para-bromoiodobenzene (1.48 g, 5.23 mmol), triethylamine (0.893 g, 8.82 mmol), Pd(PPh$_3$)$_2$Cl$_2$ (0.094 g, 0.134 mmol) and CuI (0.047 g, 0.247 mmol) were dissolved in THF (20 mL). The atmosphere was replaced with nitrogen gas three times. The mixture was stirred at normal temperature for 18 hours, rotary-evaporated to dryness, and purified by silica column chromatography (100% petroleum ether→petroleum ether:ethyl acetate=1:2) to give a white solid (1.1 g) in a yield of 68.9%.

(2) Preparation of (2S,3R)-3-hydroxy-2-(4-((4-(1-methyl-1H-pyrazol-5-yl)phenyl)ethynyl)benzamido)butanoic Acid

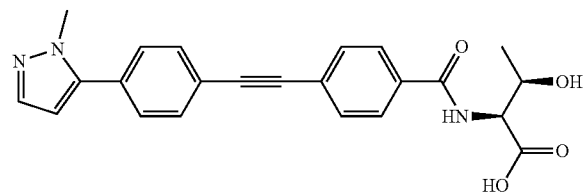 [SMILES: C[C@@H](O)[C@H](NC(=O)c1ccc(C#Cc2ccc(-c3ccnn3C)cc2)cc1)C(=O)O]

(2S,3R)-methyl 2-(4-((4-bromophenyl)ethynyl)benzamido)-3-hydroxybutanoate (1.10 g, 2.64 mmol), 1-methyl-1H-pyrazol-5-boronic acid pinacol ester (0.66 g, 3.17 mmol), sodium carbonate (0.421 g, 3.97 mmol) and Pd(PPh$_3$)$_4$ (0.306 g, 0.265 mmol) were dissolved in 1,4-dioxane (20 mL) and water (1 mL). The atmosphere was replaced with nitrogen gas three times. The mixture was stirred under reflux for 18 hours, rotary-evaporated to dryness, and purified by silica column chromatography (100% dichloromethane→dichloromethane:methanol=10:1) to give a colorless oily product (0.821 g) in a yield of 77.1%.

(3) Preparation of (2S,3R)-methyl 3-hydroxy-2-(4-((4-(1-methyl-1H-pyrazol-5-yl)phenyl)ethynyl)benzamido)butanoate

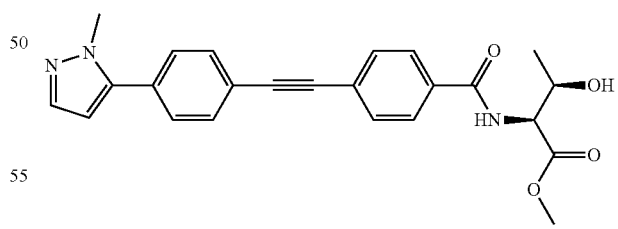

(2S,3R)-3-hydroxy-2-(4-((4-(1-methyl-1H-pyrazol-5-yl)phenyl)ethynyl)benzamido)butanoic acid (0.452 g, 1.12 mmol) was dissolved in methanol (15 mL). Then thionyl chloride (3 mL) was added at 0° C. The resulting mixture was stirred for 2 hours, and rotary-evaporated to dryness to give a white solid, which was directly used in the next step.

(4) Preparation of N-((2S,3R)-3-hydroxy-1-(hydroxyamino)-1-oxobutan-2-yl)-4-((4-(1-methyl-1H-pyrazol-5-yl)phenyl)ethynyl)benzamide

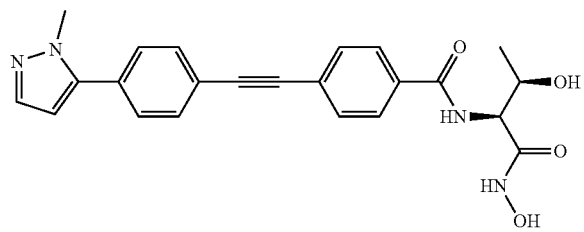 [SMILES: C[C@@H](O)[C@H](NC(=O)c1ccc(C#Cc2ccc(-c3ccnn3C)cc2)cc1)C(=O)NO]

The solid obtained in the previous step was dissolved in methanol (10 mL). An aqueous hydroxylamine solution (50%, 8 mL) and lithium hydroxide monohydrate (0.032 g, 0.762 mmol) were added. The mixture was reacted under stirring for 3 hours, and a white solid was separated. The mixture was filtered. The filter cake was washed with methanol and water respectively to give a white solid (0.096 g) in a yield of 20.4% in two steps.

Molecular Formula: $C_{23}H_{22}N_4O_4$; Molecular Weight: 418.2; Mass Spectrum (M+H): 419.2

$^1$H-NMR (d$_6$-DMSO, 400 MHz) δ 10.72 (1H, s), 8.85 (1H, s), 8.17 (1H, d), 7.96 (2H, d), 7.80-7.60 (6H, m), 7.49 (1H, d), 6.49 (1H, d), 5.15-4.80 (1H, br), 4.26 (1H, q), 4.03 (1H, t), 3.89 (3H, s), 1.07 (3H, d).

Example 31: Preparation of (S)—N-(3-amino-1-(hydroxyamino)-3-methyl-1-oxobutan-2-yl)-4-((4-(3-(hydroxymethyl)-1-methyl-1H-pyrazol-5-yl)phenyl)ethynyl)benzamide (Compound 37)

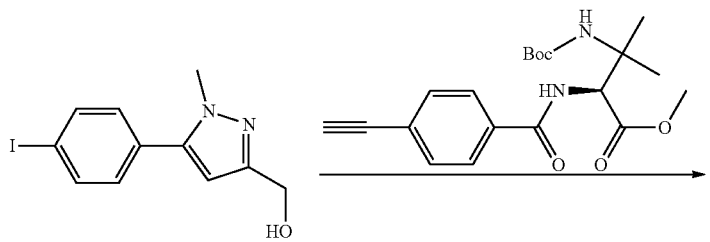

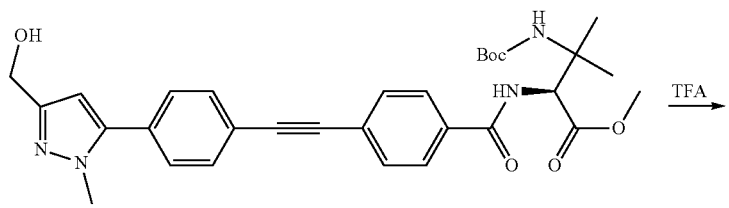

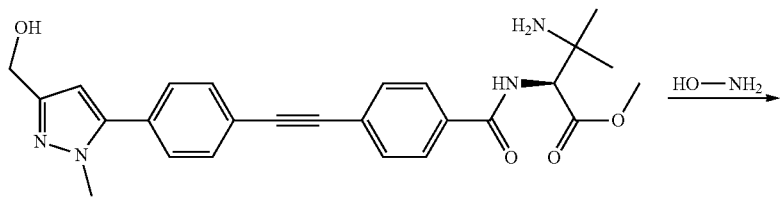

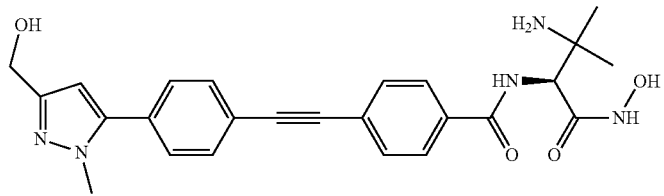

(1) Preparation of (S)-methyl 3-(tert-butoxycarbonylamino)-2-(4-((4-(3-(hydroxymethyl)-1-methyl-1H-pyrazol-5-yl)phenyl)ethynyl)benzamido)-3-methylbutanoate

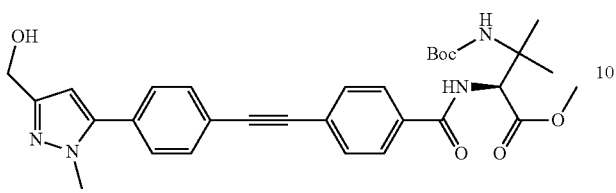

(S)-methyl 3-(tert-butoxycarbonylamino)-2-(4-ethynylbenzamido)-3-methylbutanoate (0.30 g, 0.801 mmol), (5-(4-iodophenyl)-1-methyl-1H-pyrazol-3-yl)methanol (0.252 g, 0.801 mmol), triethylamine (0.242 g, 2.40 mmol), Pd(PPh₃)₂Cl₂ (0.022 g, 0.031 mmol) and CuI(3 mg, 0.016 mmol) were dissolved in acetonitrile (20 mL). The atmosphere was replaced with nitrogen gas for three times. The mixture was stirred at room temperature for 17 hours, rotary-evaporated to dryness, and purified by silica column chromatography (100% dichloromethane→dichloromethane:methanol=20:1) to give a white solid (0.320 g) in a yield of 71.3%.

(2) Preparation of (S)-methyl 3-amino-2-(4-((4-(3-(hydroxymethyl)-1-methyl-1H-pyrazol-5-yl)phenyl)ethynyl)benzamido)-3-methylbutanoate

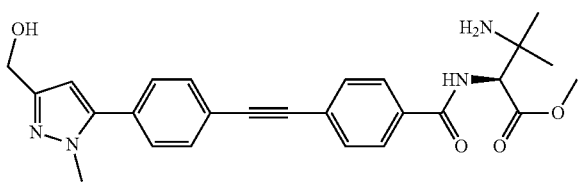 [SMILES: COC(=O)[C@@H](NC(=O)c1ccc(C#Cc2ccc(-c3cc(CO)nn3C)cc2)cc1)C(C)(C)N]

(S)-methyl 3-(tert-butoxycarbonylamino)-2-(4-((4-(3-(hydroxymethyl)-1-methyl-1H-pyrazol-5-yl)phenyl)ethynyl)benzamido)-3-methylbutanoate (0.30 g, 0.535 mmol) was dissolved in dichloromethane (10 mL). TFA (1 mL) was added. The mixture was reacted under stirring for 2 hours, and rotary-evaporated to dryness to give a crude reddish-brown oily product (0.36 g), which was directly used in the next step.

(3) Preparation of (S)—N-(3-amino-1-(hydroxyamino)-3-methyl-1-oxobutan-2-yl)-4-((4-(3-(hydroxymethyl)-1-methyl-1H-pyrazol-5-yl)phenyl)ethynyl)benzamide

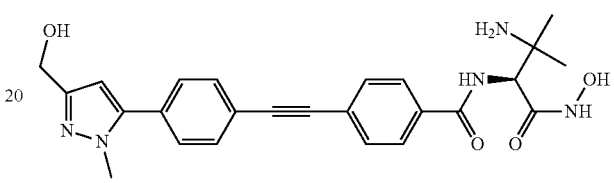

The oily substance obtained in the previous step was dissolved in methanol (10 mL). An aqueous hydroxylamine solution (50%, 2 mL) and lithium hydroxide monohydrate (0.013 g, 0.31 mmol) were added. The mixture was reacted under stirring for 70 hours, rotary-evaporated to dryness, and purified by preparative liquid phase chromatography (100% water→water:methanol=100:62) to give a white solid (0.066 g) in a yield of 26.7% (in two steps).

Molecular Formula: $C_{25}H_{27}N_5O_4$; Molecular Weight: 461.2; Mass Spectrum (M+H): 462.2

¹H-NMR (d-DMSO, 600 MHz) δ 8.12 (1H, s), 7.88 (2H, d), 7.79 (2H, d), 7.62 (2H, d), 7.56 (2H, d), 6.66 (1H, s), 5.31 (1H, m), 5.15-4.68 (2H, br), 4.50 (2H, d), 4.17 (1H, s), 3.82 (3H, s), 1.07 (3H, s), 0.99 (3H, s).

Example 32: Preparation of N-hydroxy-2-methyl-4-(4-(4-((4-(1-methyl-1H-pyrazol-5-yl)phenyl)ethynyl)phenyl)-2-oxopyridin-1(2H)-yl)-2-(methylsulfonyl)butanamide (Compound 38)

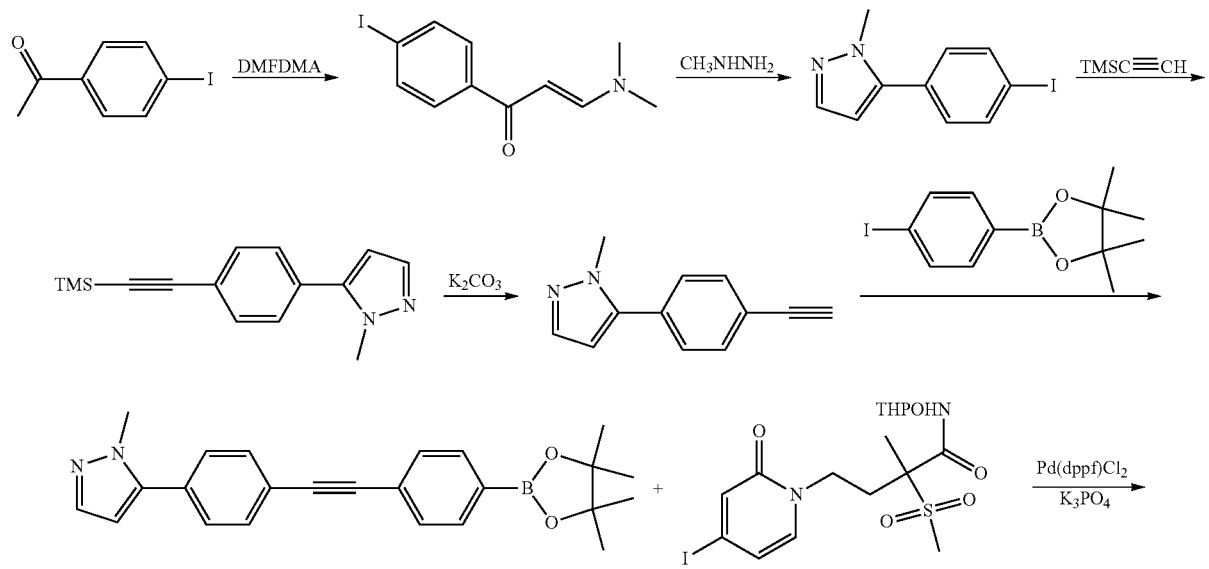

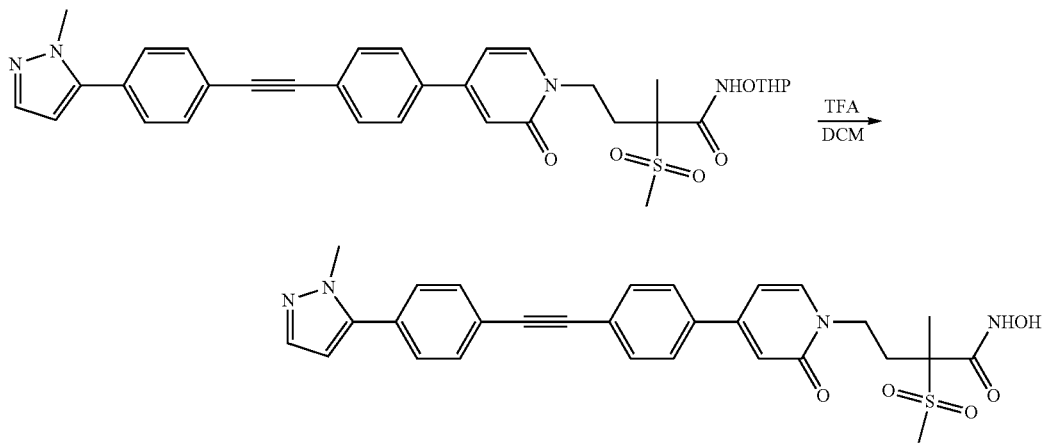

(1) Preparation of 3-(dimethylamino)-1-(4-iodophenyl)prop-2-en-1-one

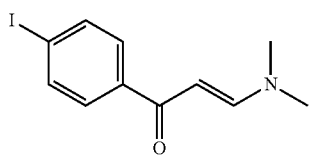

4-iodophenylethanone (4.92 g, 20.00 mmol) and N,N-dimethylformamide dimethylacetal (4.77 g, 40.00 mmol) were dissolved in N,N-dimethylformamide (15.00 mL). The mixture was reacted at 125° C. for 3 hours and concentrated under reduced pressure to give a red oily substance (6.02 g), which was directly used in the next step.

(2) Preparation of 5-(4-iodophenyl)-1-methyl-1H-pyrazole

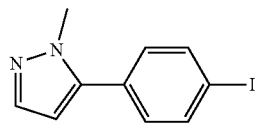

3-(dimethylamino)-1-(4-iodophenyl)prop-2-en-1-one (6.02 g, 20.00 mmol) was dissolved in N,N-dimethylformamide (10.00 mL). Methylhydrazine (2.76 g, 60.00 mmol) was added. The mixture was reacted at room temperature for 1 hour and then at 75° C. for 4 hours, concentrated under reduced pressure, purified by silica column chromatography (petroleum ether:ethyl acetate=5:1) to give a solid (3.35 g) in a yield of 58.9%.

(3) Preparation of 1-methyl-5-(4-((trimethylsilyl)ethynyl)phenyl)-1H-pyrazole

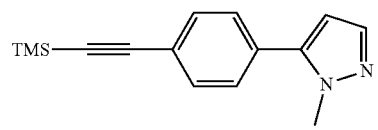

5-(4-iodophenyl)-1-methyl-H-pyrazole(2.60 g, 9.15 mmol), trimethylsilylethyne (1.79 g, 18.30 mmol), bis(triphenylphosphine)palladium dichloride (323 mg, 0.46 mmol), cuprous iodide (88 mg, 0.46 mmol) and triethylamine (2.78 g, 27.45 mmol) were dissolved in 1,4-dioxane (40 mL). In the nitrogen protection, the mixture was reacted under reflux for 3 hours, cooled, and concentrated to give a crude solid (2.33 g), which was directly used in the next step.

(4) Preparation of 5-(4-ethynylphenyl)-1-methyl-1H-pyrazole

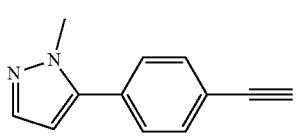

The crude product obtained in the previous step (2.33 g, 9.15 mmol) was dissolved in methanol (50 mL). Potassium carbonate (2.53 g, 18.30 mmol) was added. The mixture was reacted at room temperature for 4 hours. After the completion of the reaction, water (100 mL) was added to the reaction system. The reaction mixture was extracted with ethyl acetate three times. The organic phases were combined. The organic phase was washed with water, washed with saturated brine, dried over anhydrous sodium sulphate, rotary-evaporated to dryness, and purified by column chromatography (PE:EA=5:1) to give a white solid (1.47 g) in a yield of 88.5%.

(5) Preparation of 1-methyl-5-(4-((4-(4,4,5,5-tetramethyl-1,3,2-dioxaborolan-2-yl)phenyl)ethynyl)phenyl)-1H-pyrazole

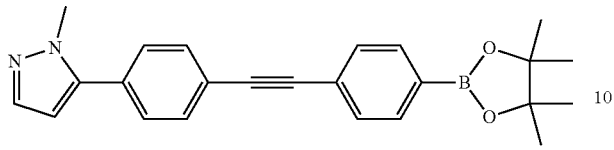

5-(4-ethynylphenyl)-1-methyl-H-pyrazole (273 mg, 1.50 mmol), 4-iodophenyl boronic acid pinacol ester (495 mg, 1.50 mmol), bis(triphenylphosphine)palladium dichloride (21 mg, 0.030 mmol), cuprous iodide (3 mg, 0.016 mmol) and triethylamine (455 mg, 4.50 mmol) were dissolved in acetonitrile (15 mL). Under the nitrogen protection, the mixture was reacted at room temperature for 6 hours, cooled, concentrated, and purified by silica column chromatography (petroleum ether:ethyl acetate=3:1) to give a white solid (424 mg) in a yield of 73.6%.

(6) Preparation of 2-methyl-4-(4-(4-((4-(1-methyl-1H-pyrazol-5-yl)phenyl)ethynyl)phenyl)-2-oxopyridin-1(2H)-yl)-2-(methylsulfonyl)-N-(tetrahydro-2H-pyran-2-yloxy)butanamide

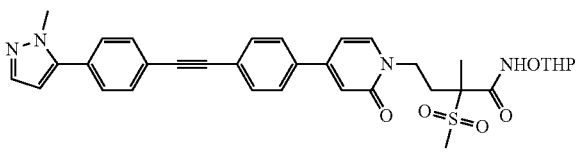

1-methyl-5-(4-((4-(4,4,5,5-tetramethyl-1,3,2-dioxaborolan-2-yl)phenyl)ethynyl)phenyl)-1H-pyrazole (234 mg, 0.61 mmol), 4-(4-iodo-2-oxopyridin-1(2H)-yl)-2-methyl-2-(methylsulfonyl)-N-(tetrahydro-2H-pyran-2-yloxy)butanamide (304 mg, 0.61 mmol), [1,1'-bis(diphenylphosphine)ferrocene] palladium(II) dichloride dichloromethane complex (50 mg, 0.061 mmol) and potassium phosphate (388 mg, 1.83 mmol) were added to 1,4-dioxane (20 mmol) and water (1 mL). In the nitrogen protection, the mixture was reacted at 90° C. for 16 hours, cooled, concentrated, dissolved in ethyl acetate, and washed with water. The organic phases were dried over anhydrous sodium sulphate, concentrated, and purified by silica column chromatography (petroleum ether:ethyl acetate=1:1) to give a solid (177 mg) in a yield of 46.3%.

(7) Preparation of N-hydroxy-2-methyl-4-(4-(4-((4-(1-methyl-1H-pyrazol-5-yl)phenyl)ethynyl)phenyl)-2-oxopyridin-1(2H)-yl)-2-(methylsulfonyl)butanamide

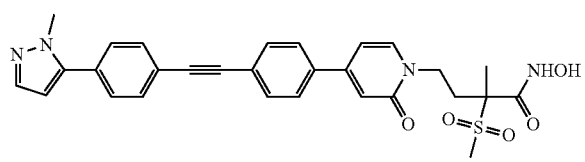

2-methyl-4-(4-(4-((4-(1-methyl-1H-pyrazol-5-yl)phenyl)ethynyl)phenyl)-2-oxopyridin-1(2H)-yl)-2-(methylsulfonyl)-N-(tetrahydro-2H-pyran-2-yloxy)butanamide (177 mg, 0.28 mmol) was dissolved in dichloromethane (20 mL). In an ice bath, trifluoroacetic acid (3 mL) was added dropwisely. The mixture was reacted at room temperature for 5 hours. TLC (petroleum ether:ethyl acetate=1:1) indicated the completion of the reaction. The reaction mixture was concentrated under reduced pressure and washed with a small amount of diethyl ether and acetonitrile to give a white solid (58 mg) in a yield of 38.1%.

Molecular Formula: $C_{29}H_{28}N_4O_5S$; Molecular Weight: 544.2; Mass Spectrum (M+H): 545.2

$^1$H-NMR (d-DMSO, 400 MHz) δ 7.82 (2H, d), 7.77 (1H, d), 7.73-7.67 (4H, m), 7.63 (2H, d), 7.50 (1H, d), 6.79-6.73 (1H, m), 6.69 (1H, d), 6.50 (1H, d), 4.18-4.10 (1H, m), 3.90 (3H, s), 3.77-3.71 (1H, m), 3.10 (3H, s), 2.46-2.37 (1H, m), 2.18-2.10 (1H, m), 1.52 (3H, s).

Example 33: Preparation of 4-((4-(1H-pyrazol-5-yl)phenyl)ethynyl)-N-((2S,3R)-3-hydroxy-1-(hydroxyamino)-1-oxobutan-2-yl)benzamide (Compound 39)

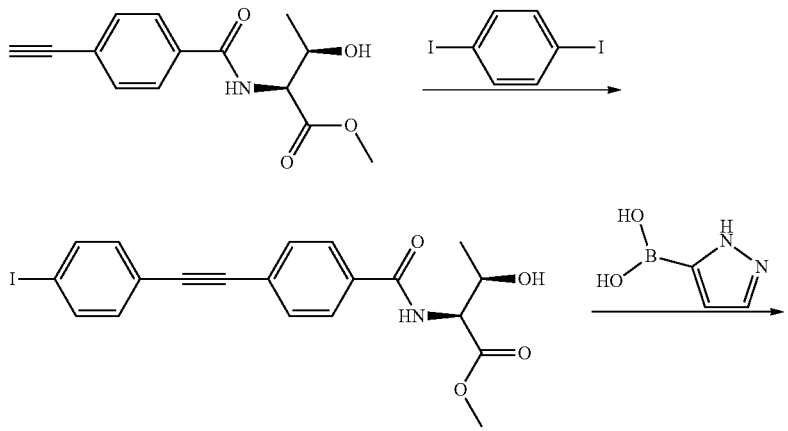

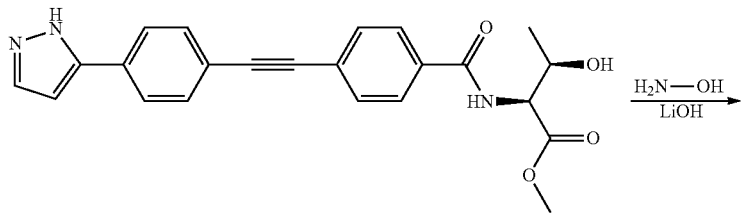

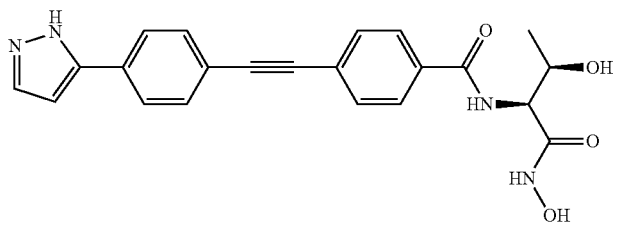

(1) Preparation of (2S,3R)-methyl 3-hydroxy-2-(4-((4-iodophenyl)ethynyl)benzamido)butanoate

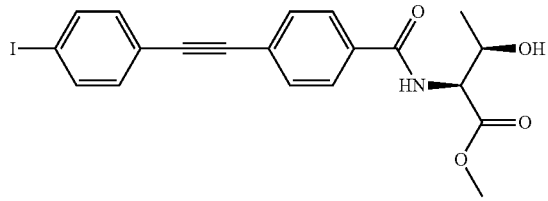 [SMILES: COC(=O)[C@@H](NC(=O)c1ccc(C#Cc2ccc(I)cc2)cc1)[C@@H](C)O]

(2S,3R)-methyl 2-(4-ethynylbenzamido)-3-hydroxybutanoate (1.00 g, 3.83 mmol), 1,4-diiodobenzene (1.726 g, 5.23 mmol), triethylamine (0.893 g, 8.82 mmol), Pd(PPh$_3$)$_2$Cl$_2$ (0.094 g, 0.134 mmol) and CuI (0.047 g, 0.247 mmol) were dissolved in THF (20 mL). The atmosphere was replaced with nitrogen gas three times. The mixture was stirred at normal temperature for 18 hours, rotary-evaporated to dryness, and purified by silica column chromatography (100% petroleum ether→petroleum ether:ethyl acetate=1:2) to give a white solid (1.3 g) in a yield of 73.4%.

(2) Preparation of (2S,3R)-methyl 2-(4-((4-(1H-pyrazol-5-yl)phenyl)ethynyl)benzamido)-3-hydroxybutanoate

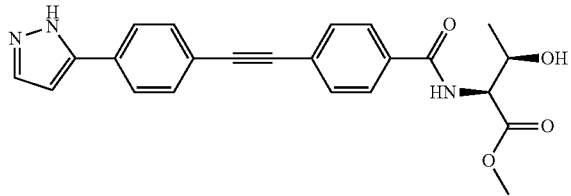 [SMILES: COC(=O)[C@@H](NC(=O)c1ccc(C#Cc2ccc(-c3ccn[nH]3)cc2)cc1)[C@@H](C)O]

(2S,3R)-methyl 3-hydroxy-2-(4-((4-iodophenyl)ethynyl)benzamido)butanoate (0.334 g, 0.721 mmol), 1H-pyrazol-5-boronic acid (0.097 g, 0.867 mmol), sodium carbonate (0.115 g, 1.085 mmol) and Pd(PPh$_3$)$_4$ (0.041 g, 0.035 mmol) were dissolved in 1,4-dioxane (10 mL) and 2 drops of water. The atmosphere was replaced with nitrogen gas three times. The mixture was stirred under reflux for 18 hours, rotary-evaporated to dryness, and purified by silica column chromatography (100% dichloromethane→dichloromethane:methanol=10:1) to give a colorless oily product (0.12 g) in a yield of 41.2%.

(3) Preparation of 4-((4-(1H-pyrazol-5-yl)phenyl)ethynyl)-N-((2S,3R)-3-hydroxy-1-(hydroxyamino)-1-oxobutan-2-yl)benzamide

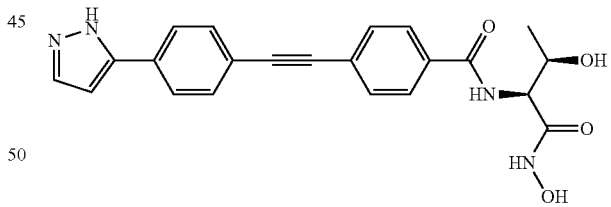

(2S,3R)-methyl 2-(4-((4-(1H-pyrazol-5-yl)phenyl)ethynyl)benzamido)-3-hydroxybutanoate (0.12 g, 0.297 mmol) was dissolved in methanol (10 mL). An aqueous hydroxylamine solution (50%, 8 mL) and lithium hydroxide monohydrate (0.008 g, 0.19 mmol) were added. The mixture was reacted at room temperature under stirring for 3 hours, rotary-evaporated to dryness, and purified by silica gel column to give Compound 39 (0.056 g) in a yield of 46.5%.

Molecular Formula: C$_{22}$H$_{20}$N$_4$O$_4$; Molecular Weight: 404.1; Mass Spectrum (M+H): 405.2

$^1$H-NMR (d$_6$-DMSO, 400 MHz) δ 13.01 (1H, s), 10.69 (1H, s), 8.86 (1H, s), 8.15 (1H, d), 7.95 (2H, d), 7.89 (2H, d), 7.81 (1H, m), 7.66 (2H, d), 7.60 (2H, d), 6.80 (1H, m), 4.90 (1H, d), 4.25 (1H, dd), 4.02 (1H, q), 1.08 (3H, d).

Example 34: Preparation of N-((2S,3R)-3-hydroxy-1-(hydroxyamino)-1-oxobutan-2-yl)-4-((6-(1-methyl-1H-pyrazol-5-yl)pyridin-3-yl)ethynyl)benzamide (Compound 40)

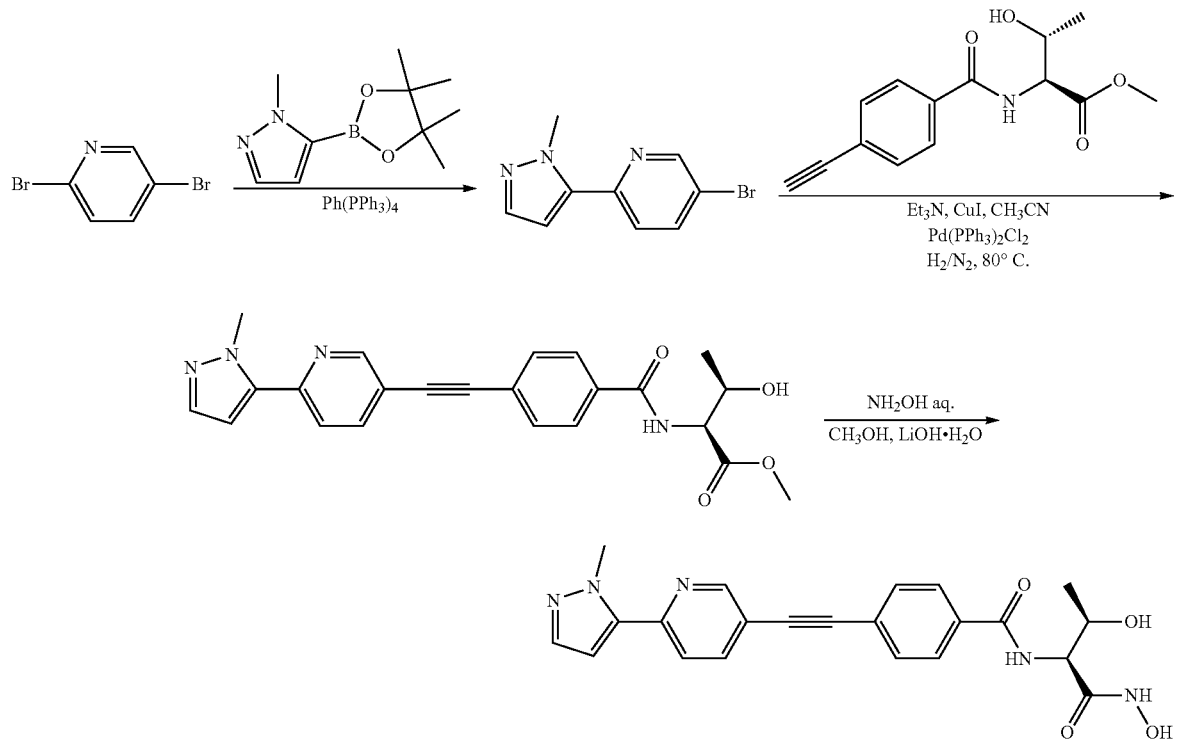

(1) Preparation of 5-bromo-2-(1-methyl-H-pyrazol-5-yl)pyridine

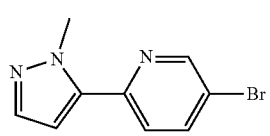

(2) Preparation of (2S,3R)-methyl 3-hydroxy-2-(4-((6-(1-methyl-1H-pyrazol-5-yl)pyridin-3-yl)ethynyl)benzamido)butanoate

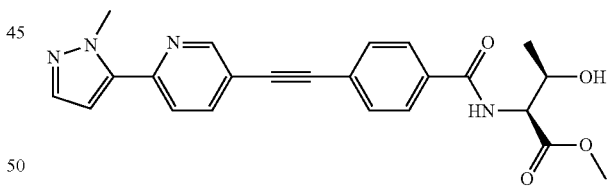

In a dry reaction flask, 2,5-dibromopyridine (521 mg, 2.2 mmol) and 1-methyl-5-(4,4,5,5-tetramethyl-1,3,2-dioxaborolan-2-yl)-1H-pyrazole (416 mg, 2.0 mmol) was dissolved in a mixed solvent of toluene (8 mL) and ethanol (8 mL). A solution of sodium carbonate (636 mg, 6.0 mmol) in water (4 mL) and Pd(PPh$_3$)$_4$ (69 mg, 0.06 mmol) was added. After the completion of the addition, the atmosphere was replaced with nitrogen gas. The mixture was reacted at 60° C. under stirring for 12 hours. The reaction mixture was cooled to room temperature. The organic phase was concentrated under reduced pressure and purified by column chromatography (PE:EA=20:1) to give a pale-yellow solid (400 mg) in a yield of 84%.

In a dry reaction flask, 5-bromo-2-(1-methyl-1H-pyrazol-5-yl)pyridine (66 mg, 0.277 mmol) and (2S,3R)-methyl 2-(4-ethynylbenzamido)-3-hydroxybutanoate (72 mg, 0.277 mmol) were added. The mixture was dissolved by adding acetonitrile (5 mL) and triethylamine (3 mL). Copper(I) iodide (0.5 mg, 0.0027 mmol) and Pd(PPh$_3$)$_2$Cl$_2$ (4 mg, 0.0054 mmol) were added. The air atmosphere was replaced with a small amount of the mixed gas of hydrogen gas and nitrogen gas. The mixture was stirred at 80° C. for 2.5 hours and cooled to room temperature. The organic phase was concentrated under reduced pressure and purified by column chromatography (PE:EA=1:2) to give a pale-yellow solid (85 mg) in a yield of 73.3%.

(3) Preparation of N-((2S,3R)-3-hydroxy-1-(hydroxyamino)-1-oxobutan-2-yl)-4-((6-(1-methyl-1H-pyrazol-5-yl)pyridin-3-yl)ethynyl)benzamide

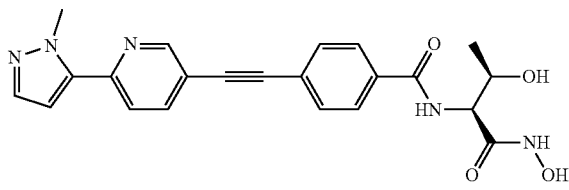 [SMILES: C[C@@H](O)[C@H](NC(=O)c1ccc(C#Cc2ccc(-c3ccnn3C)nc2)cc1)C(=O)NO]

In a dry reaction flask, (2S,3R)-methyl 3-hydroxy-2-(4-((6-(1-methyl-1H-pyrazol-5-yl)pyridin-3-yl)ethynyl)benzamido)butanoate (85 mg, 0.203 mmol) was added, and dissolved by adding methanol (4 mL). Then an aqueous hydroxylamine solution (50%, 2 mL) was added. The mixture was stirred at room temperature for 1 hour. Lithium hydroxide monohydrate (10 mg, 0.238 mmol) was added. After the completion of the addition, the mixture was stirred at room temperature for 12 hours. Water was added, and a solid was separated. The mixture was filtered by suction. The solid was washed with water and dried to give a white solid (68 mg) in a yield of 79.9%.

Molecular Formula: $CH_{21}N_5O_4$; Molecular Weight: 419.2; Mass Spectrum (M+H): 420.2

$^1$H-NMR ($d_6$-DMSO, 400 MHz): δ 8.87 (1H, s), 8.10 (1H, d), 7.96-7.82 (4H, m), 7.69 (2H, d), 7.51 (1H, d), 6.90 (1H, s), 6.41 (1H, s), 5.16 (1H, br s), 4.28-4.22 (1H, m), 4.17 (3H, s), 4.02-3.88 (1H, m), 1.01 (3H, d).

Example 35: Preparation of N-((2S,3R)-3-hydroxy-1-(hydroxyamino)-1-oxobutan-2-yl)-4-((5-(hydroxymethyl)thienyl-2-yl)buta-1,3-diynyl)benzamide (Compound 41)

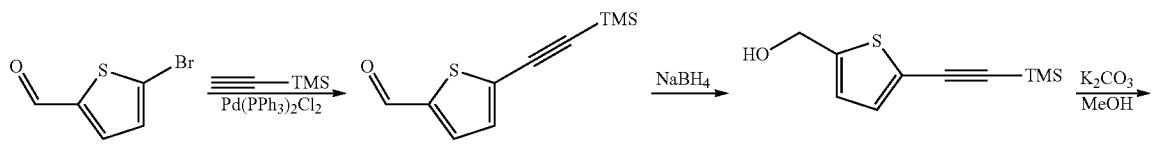

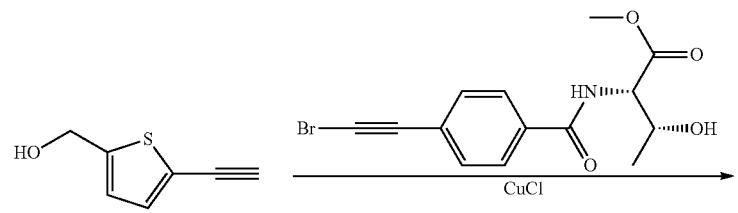

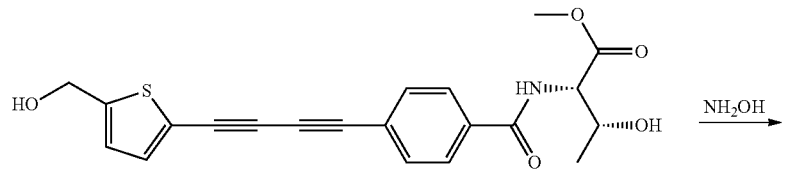

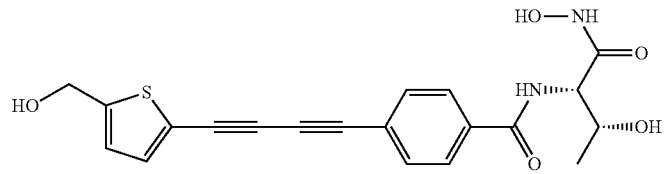

(1) Preparation of 5-((trimethylsilyl)ethynyl)thienyl-2-carbaldehyde

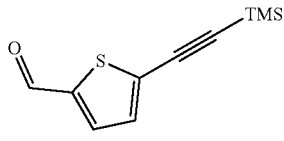 [SMILES: C[Si](C)(C)C#Cc1ccc(C=O)s1]

5-bromothienyl-2-carbaldehyde (2.7 g, 14.1 mmol), trimethylsilylethyne (2.1 g, 21.4 mmol), triethylamine (2.88 g, 28.6 mmol), Pd(PPh$_3$)$_2$Cl$_2$ (100 mg, 0.14 mmol) and CuI (27 mg, 0.14 mmol) were dissolved in THF (20 mL). The atmosphere was replaced with nitrogen gas three times. The mixture was stirred at normal temperature for 3 hours, extracted with ethyl acetate, separated into phases, rotary-evaporated to dryness, and purified by silica column chromatography (100% petroleum ether→petroleum ether:ethyl acetate=20:1) to give a pale-yellow solid (2.0 g) in a yield of 68.1%.

(2) Preparation of (5-((trimethylsilyl)ethynyl)thienyl-2-yl)methanol

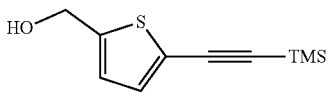 [SMILES: C[Si](C)(C)C#Cc1ccc(CO)s1]

5-((trimethylsilyl)ethynyl)thienyl-2-carbaldehyde (624 mg, 2.99 mmol) was dissolved in THF (10 mL). NaBH$_4$ (228 mg, 6.0 mmol) was added. The mixture was reacted under stirring for 0.5 hours, rotary-evaporated to dryness, and directly used in the next step reaction.

(3) Preparation of (5-ethynylthienyl-2-yl)methanol

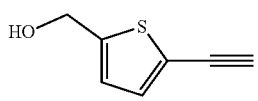

The crude product obtained in the previous step was added to anhydrous methanol (10 mL). K$_2$CO$_3$ (828 mg, 6.0 mmol) was added. The mixture was reacted at normal temperature under stirring for 16 hours. The reaction system was filtered by suction. The filtrate was rotary-evaporated to dryness and purified by silica column chromatography (PE:EA=10:1-5:1) to give an oily substance (280 mg) in a yield of 67.9% (in two steps).

(4) Preparation of (2S,3R)-methyl 3-hydroxy-2-(4-((5-(hydroxymethyl)thienyl-2-yl)buta-1,3-diynyl)benzamido)butanoate

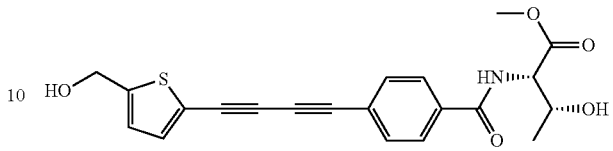

CuCl (4 mg, 0.04 mmol) and hydroxylamine hydrochloride (14 mg, 0.2 mmol) were dissolved in an aqueous n-butylamine solution (5 mL, 23%). (5-ethynylthienyl-2-yl)methanol (280 mg, 2.03 mmol) dissolved in an aqueous n-butylamine solution (2.5 mL, 23%) was added, and then a solution of (2S,3R)-methyl 2-(4-(bromoethynyl)benzamido)-3-hydroxybutanoate (400 mg, 1.18 mmol) dissolved in methanol (2.5 mL) and tetrahydrofuran (1.0 mL) was added to the above reaction solution. The resulting mixture was stirred for 5 minutes, and ethyl acetate (20 mL) and water (20 mL) were added. The mixture was extracted, and the organic phase was dried over anhydrous sodium sulphate, rotary-evaporated to dryness, and purified by silica column chromatography (PE:EA=10:1→2:3) to give a product (200 mg) in a yield of 42.6%.

(5) Preparation of N-((2S,3R)-3-hydroxy-1-(hydroxyamino)-1-oxobutan-2-yl)-4-((5-(hydroxymethyl)thienyl-2-yl)buta-1,3-diynyl)benzamide

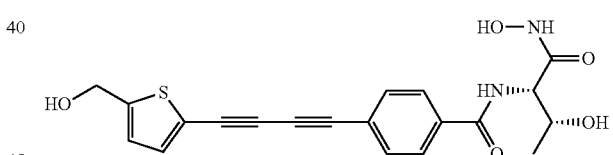

(2S,3R)-methyl 3-hydroxy-2-(4-((5-(hydroxymethyl)thienyl-2-yl)buta-1,3-diynyl)benzamido)butanoate (200 mg, 0.503 mmol) was dissolved in methanol (2 mL). An aqueous hydroxylamine solution (50%, 2 mL) and lithium hydroxide monohydrate (9 mg, 0.214 mmol) were added. The mixture was reacted under stirring for 72 hours, rotary-evaporated to remove methanol, and filtered. The filter cake was dissolved in DMSO. The resulting mixture was purified by preparative liquid phase chromatography to give a product (40 mg) in a yield of 19.9%.

Molecular Formula: C$_{20}$H$_{18}$N$_2$O$_5$S; Molecular Weight: 398.1; Mass Spectrum: (M+H): 398.9

$^1$H-NMR (d-DMSO, 400 MHz) δ 10.66 (1H, s), 8.84 (1H, s), 8.18 (1H, d), 7.93 (2H, d), 7.70 (2H, d), 7.44 (1H, d), 6.95 (1H, d), 5.71 (1H, t), 4.93-4.84 (1H, m), 4.65 (2H, d), 4.24 (1H, dd), 4.06-3.96 (1H, m), 1.07 (3H, d).

Example 36: Preparation of N-((2S,3R)-3-hydroxy-1-(hydroxyamino)-1-oxobutan-2-yl)-4-((5-((2-(2-hydroxyethoxy)ethylamino)methyl)thienyl-2-yl)buta-1,3-diynyl)benzamide (Compound 42)

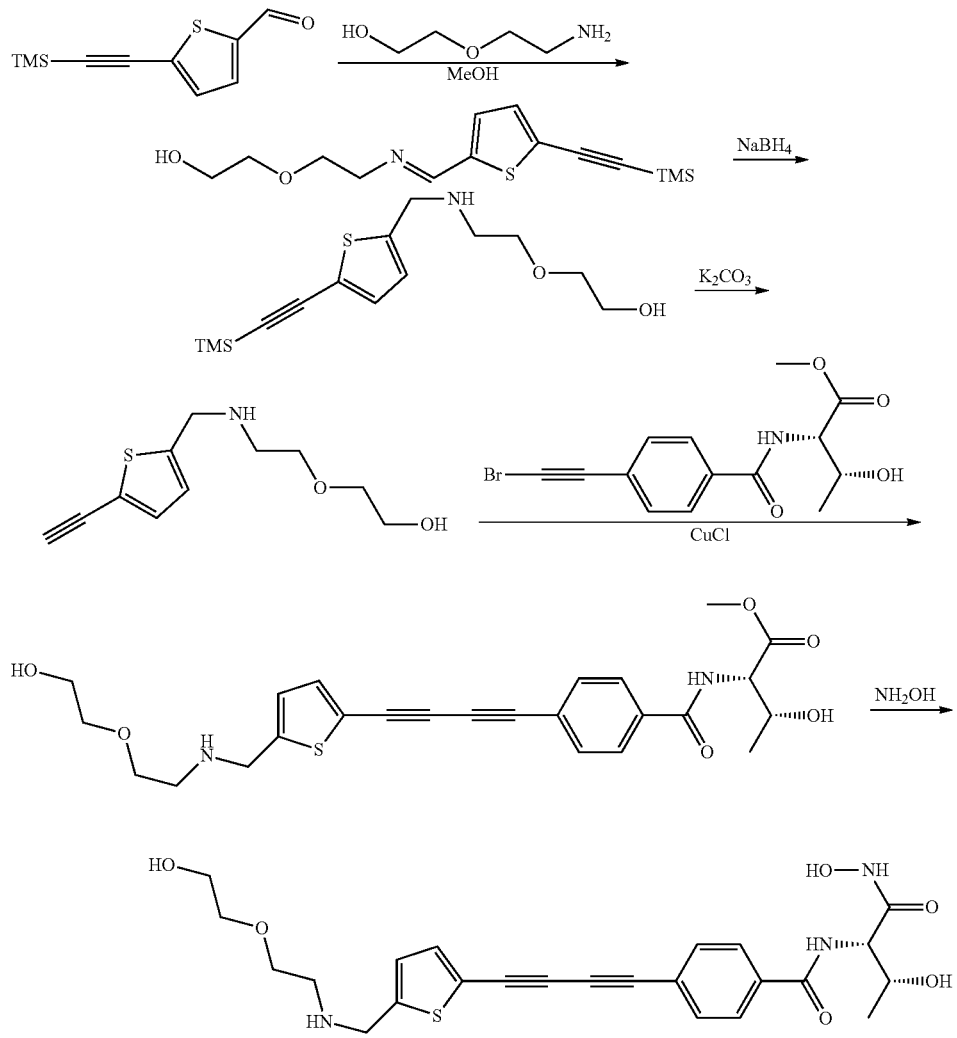

(1) Preparation of 2-(2-((5-((trimethylsilyl)ethynyl)thienyl-2-yl)methyleneamino)ethoxy)ethanol

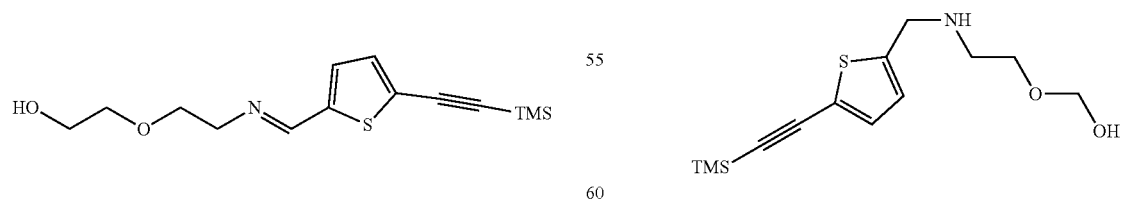

5-((trimethylsilyl)ethynyl)thienyl-2-carbaldehyde (0.433 g, 2.08 mmol) was dissolved in methanol (10 mL). 2-(2-aminoethoxy)ethanol (0.218 g, 2.08 mmol) was added. One drop of acetic acid was added. The mixture was stirred at room temperature overnight, which was directly used in the next step.

(2) Preparation of 2-(2-((5-((trimethylsilyl)ethynyl)thienyl-2-yl)methylamino)ethoxy)ethanol To the reaction system from the previous step sodium borohydride (0.236 g, 6.24 mmol) was added. The mixture was stirred at room temperature for 1 hour. LC-MS indicated the completion of the reaction. The product was directly used in the next reaction without the need for further treatment.

(3) Preparation of 2-(2-((5-ethynylthienyl-2-yl)methylamino)ethoxy)ethanol

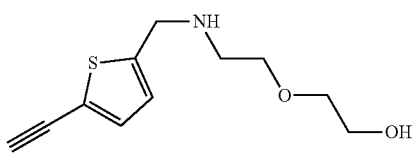

To the reaction system from the previous step potassium carbonate (0.862 g, 6.24 mmol) was added. The mixture was reacted at room temperature for 4 hours. After the completion of the reaction, water (100 mL) was added to the reaction system. The resulting mixture was extracted with ethyl acetate three times. The organic phases were combined. The combined organic phase was washed with water, wash with saturated brine, dried over anhydrous sodium sulphate, rotary-evaporated to dryness, and purified by column chromatography (PE:EA=5:1→DCM:MeOH=20:1) to give a brown oily substance (0.25 g) in a yield of 53.4% (in three steps).

(4) Preparation of methyl (2S,3R)-3-hydroxy-2-(4-((5-((2-(2-hydroxyethoxy)ethylamino)methyl)thienyl-2-yl)buta-1,3-diynyl)benzamido)butanoate

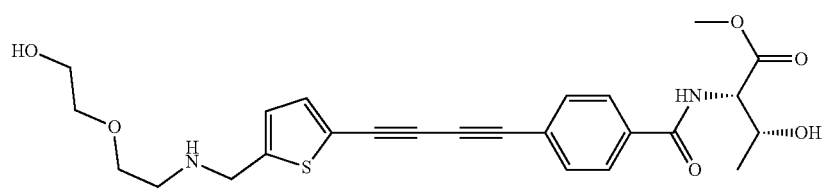 [SMILES: COC(=O)[C@@H](NC(=O)c1ccc(C#CC#Cc2ccc(CNCCOCCO)s2)cc1)[C@@H](C)O]

CuCl (6 mg, 0.06 mmol) and hydroxylamine hydrochloride (14 mg, 0.2 mmol) were dissolved in an aqueous n-butylamine solution (6 mL, 23%). A solution of 2-(2-((5-ethynylthienyl-2-yl)methylamino)ethoxy)ethanol (0.25 g, 1.11 mmol) in methanol and tetrahydrofuran (5 mL, V:V, 1:1), and a solution of (2S,3R)-methyl 2-(4-(bromoethynyl)benzamido)-3-hydroxybutanoate (0.377 g, 1.11 mmol) in methanol and tetrahydrofuran (5 mL, V:V, 1:1) were successively added to the above reaction solution. The mixture was stirred for 2 minutes. Ethyl acetate (20 mL) and water (20 mL) were added. The mixture was extracted three times. The organic phase was dried over anhydrous sodium sulphate, rotary-evaporated to dryness, and purified by silica column chromatography (petroleum ether:ethyl acetate=5:1→dichloromethane:methanol=20:1) to give a yellow solid (0.22 g) in a yield of 40.9%.

(5) Preparation of N-((2S,3R)-3-hydroxy-1-(hydroxyamino)-1-oxobutan-2-yl)-4-((5-((2-(2-hydroxyethoxy)ethylamino)methyl)thienyl-2-yl)buta-1,3-diynyl)benzamide

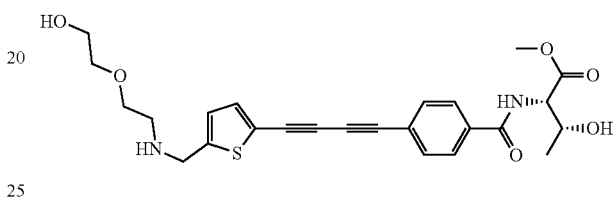

(2S,3R)-methyl 3-hydroxy-2-(4-((5-((2-(2-hydroxyethoxy)ethylamino)methyl)thienyl-2-yl)buta-1,3-diynyl)benzamido)butanoate (0.22 g, 0.454 mmol) was dissolved in methanol (1 mL). An aqueous hydroxylamine solution (50%, 4 mL) was added. The mixture was reacted under stirring for 1 hour, and directly purified by preparative liquid phase chromatography (methanol:water=40:100) to give a yellow solid (69 mg) in a yield of 31.3%.

Molecular Formula: $C_{24}H_{27}N_3O_6S$; Molecular Weight: 485.2; Mass Spectrum: (M+H): 486.2

$^1$H-NMR (DMSO-$d_6$, 600 MHz) δ 10.67 (1H, s), 8.84 (1H, s), 8.18 (1H, d), 7.92 (2H, d), 7.68 (2H, d), 7.42 (1H, d), 6.95 (1H, d), 4.87 (1H, d), 4.63-4.52 (1H, m), 4.22 (1H, dd), 4.03-3.96 (1H, m), 3.90 (2H, s), 3.49-3.41 (4H, m), 3.38 (2H, t), 2.66 (2H, t), 1.06 (3H, d).

Example 37: Preparation of N-((2S,3R)-3-hydroxy-1-(hydroxyamino)-1-oxobutan-2-yl)-4-((5-(morpholinomethyl)thienyl-2-yl)buta-1,3-diynyl)benzamide (Compound 43)

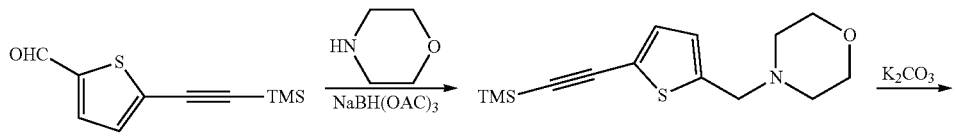

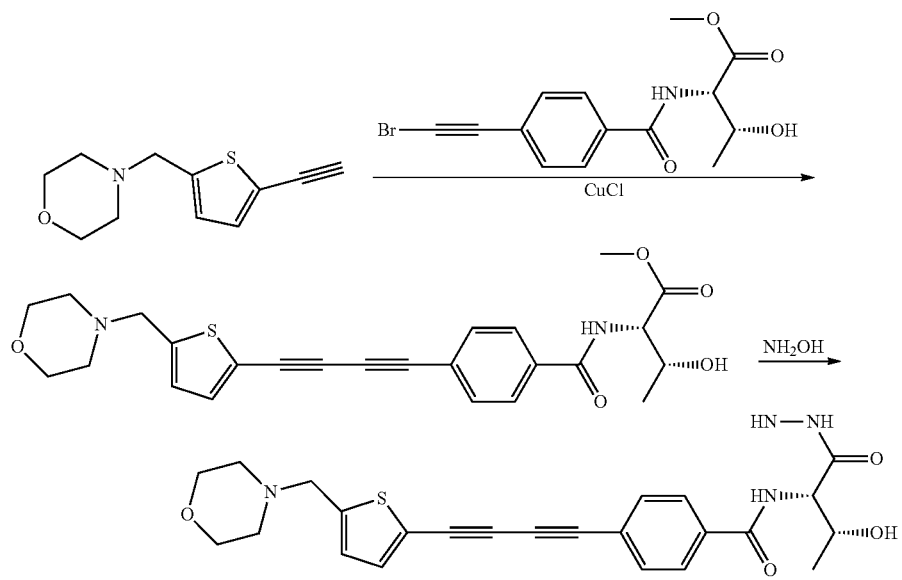

(1) Preparation of 4-((5-((trimethylsilyl)ethynyl)thienyl-2-yl)methyl)morpholine

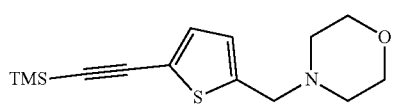 [SMILES: C[Si](C)(C)C#Cc1ccc(CN2CCOCC2)s1]

5-((trimethylsilyl)ethynyl)thienyl-2-carbaldehyde (458 mg, 2.2 mmol) and morpholine (174 mg, 2.0 mmol) were dissolved in DCM (10 mL). Sodium triacetoxyhydroborate (730 mg, 3.4 mmol) was added. The mixture was reacted at room temperature under stirring for 4 days (sodium triacetoxyhydroborate (80 mg) was supplemented every day), and rotary-evaporated to dryness. The product was directly used in the next reaction.

(2) Preparation of 4-((5-ethynylthienyl-2-yl)methyl)morpholine

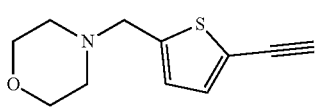

The crude product obtained in the previous step was added to anhydrous methanol (10 mL). K$_2$CO$_3$ (828 mg, 6.0 mmol) was added. The mixture was reacted at normal temperature under stirring for 16 hours. The reaction system was filtered by suction. The filtrate was rotary-evaporated to dryness and purified by silica column chromatography (PE:EA=10:1→1:1) to give an oily substance (200 mg) in a yield of 48.2% (in two steps).

(3) Preparation of (2S,3R)-methyl 3-hydroxy-2-(4-((5-(morpholinomethyl)thienyl-2-yl)buta-1,3-diynyl)benzamido)butanoate

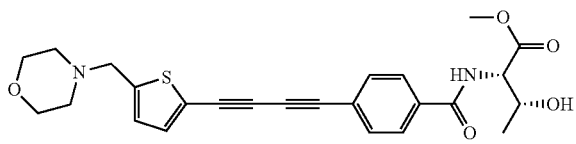 [SMILES: COC(=O)[C@@H](NC(=O)c1ccc(C#CC#Cc2ccc(CN3CCOCC3)s2)cc1)[C@@H](C)O]

CuCl (2 mg, 0.02 mmol) and hydroxylamine hydrochloride (7 mg, 0.1 mmol) were dissolved in an aqueous n-butylamine solution (1.5 mL, 23%). 4-((5-ethynylthienyl-2-yl)methyl)morpholine (200 mg, 0.965 mmol) dissolved in an aqueous n-butylamine solution (0.5 mL, 23%) was added, and then a solution of (2S,3R)-methyl 2-(4-(bromoethynyl)benzamido)-3-hydroxybutanoate (200 mg, 0.588 mmol) in methanol (1.5 mL) and tetrahydrofuran (0.75 mL) was added to the above reaction solution. The resulting mixture was stirred for 5 minutes. Ethyl acetate (20 mL) and water (20 mL) were added. The mixture was extracted. The organic phase was dried over anhydrous sodium sulphate, rotary-evaporated to dryness, and purified by silica column chromatography (DCM:MeOH=10:1) to give a product (148 mg) in a yield of 53.9%.

(4) Preparation of N-((2S,3R)-3-hydroxy-1-(hydroxyamino)-1-oxobutan-2-yl)-4-((5-(morpholinomethyl)thienyl-2-yl)buta-1,3-diynyl)benzamide

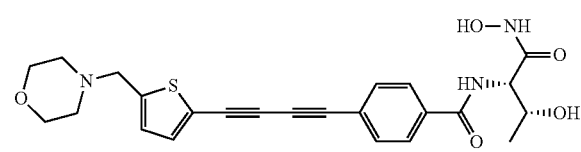 [SMILES: C[C@@H](O)[C@H](NC(=O)c1ccc(C#CC#Cc2ccc(CN3CCOCC3)s2)cc1)C(=O)NO]

(2S,3R)-methyl 3-hydroxy-2-(4-((5-(morpholinomethyl)thienyl-2-yl)buta-1,3-diynyl)benzamido)butanoate (148 mg, 0.317 mmol) was dissolved in methanol (1 mL). An aqueous hydroxylamine solution (50%, 3 mL) was added. The mixture was reacted at room temperature under stirring for 3 hours, and directly purified by preparative liquid phase chromatography (methanol:water=50:100) to give a product (90 mg) in a yield of 60.9%.

Molecular Formula: $C_{24}H_{25}N_3O_5S$; Molecular Weight: 467.2; Mass Spectrum: (M+H): 468.2

$^1$H-NMR (d$_6$-DMSO, 600 MHz) δ 10.66 (1H, s), 8.82 (1H, s), 8.17 (1H, d), 7.92 (2H, d), 7.69 (2H, d), 7.43 (1H, d), 6.98 (1H, d), 4.93-4.84 (1H, m), 4.22 (1H, dd), 4.00 (1H, quintet), 3.68 (2H, s), 3.56 (4H, t), 2.42-2.36 (4H, m), 1.06 (3H, d).

Example 38: Preparation of N-((2S,3R)-3-hydroxy-1-(hydroxyamino)-1-oxobutan-2-yl)-4-((5-(pyridin-2-yl)thienyl-2-yl)ethynyl)benzamide (Compound 44)

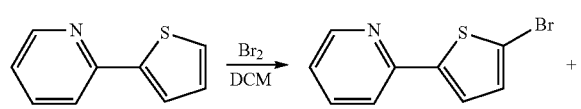

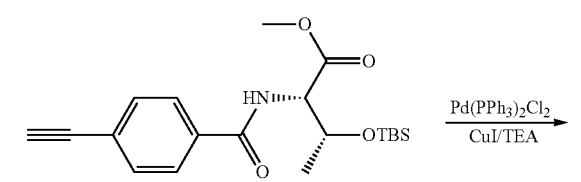

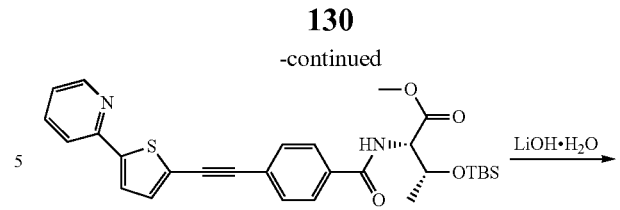

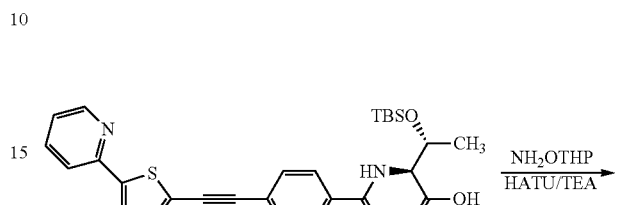

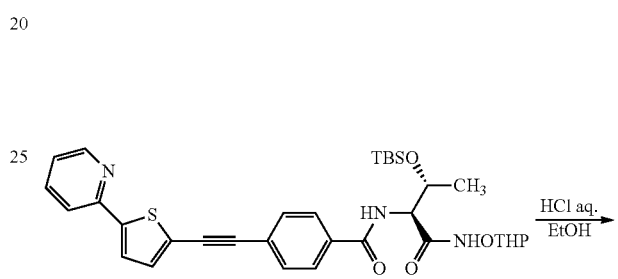

(1) Preparation of 2-(5-bromothienyl-2-yl)pyridine

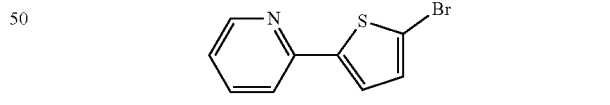

At 0° C. to a solution of 2-(thienyl-2-yl)pyridine (5 g, 31.0 mmol) in dichloromethane (50 mL) was slowly added dropwisely a solution of liquid bromine (5.45 g, 34.1 mmol) in dichloromethane (20 mL). After the dropwise addition, the mixture was transferred to room temperature and reacted under stirring for 6 hours. The reaction mixture was diluted with dichloromethane (200 mL) and successively washed with a sodium bicarbonate solution, a sodium sulphite solution, and a saturated brine solution. The organic phase was dried over anhydrous sodium sulphate and concentrated to give a red solid (7.16 g) in a yield of 96.2%.

(2) Preparation of (2S,3R)-methyl 3-(tert-butyldimethylsilyloxy)-2-(4-((5-(pyridin-2-yl)thienyl-2-yl)ethynyl)benzamido)butanoate

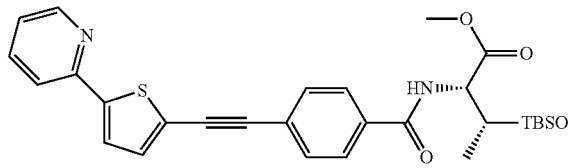 [SMILES: COC(=O)[C@@H](NC(=O)c1ccc(C#Cc2ccc(-c3ccccn3)s2)cc1)[C@@H](C)O[Si](C)(C)C(C)(C)C]

2-(5-bromothienyl-2-yl)pyridine (576 mg, 2.4 mmol), (2S,3R)-methyl 3-(tert-butyldimethylsilyloxy)-2-(4-ethynylbenzamido)butanoate (751 mg, 2.0 mmol), bis(triphenylphosphine)palladium dichloride (49 mg, 0.07 mmol), cuprous iodide (24 mg, 0.126 mmol) and triethylamine (607 mg, 6.0 mmol) were dissolved in tetrahydrofuran (60 mL). In the nitrogen protection, the mixture was reacted under reflux for 6 hours, cooled, concentrated, and purified by silica column chromatography (petroleum ether:ethyl acetate=2:1) to give a white solid (710 mg) in a yield of 66.4%.

(4) Preparation of (2S,3R)-3-(tert-butyldimethylsilyloxy)-2-(4-((5-(pyridin-2-yl)thienyl-2-yl)ethynyl)benzamido)butanoic Acid

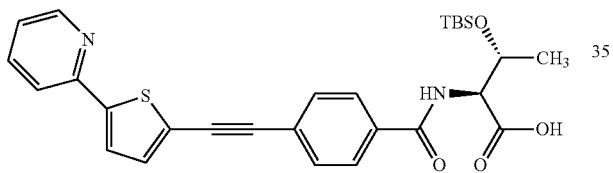

(2S,3R)-methyl 3-(tert-butyldimethylsilyloxy)-2-(4-((5-(pyridin-2-yl)thienyl-2-yl)ethynyl)benzamido)butanoate (710 mg, 1.33 mmol) and lithium hydroxide monohydrate (279 mg, 6.64 mmol) were added to a solvent mixture of tetrahydrofuran/methanol/water (33 mL, v/v/v=5:5:1). The mixture was reacted for 18 hours, and rotary-evaporated to dryness to remove the organic solvent. Water was added. The resulting mixture was adjusted with a diluted hydrochloric acid to a pH value of about 6, filtered by suction, and dried to give a white solid (660 mg) in a yield of 95.5%.

(5) Preparation of N-((2S,3R)-3-(tert-butyldimethylsilyloxy)-1-oxo-1-(tetrahydro-2H-pyran-2-yloxyamino)butan-2-yl)-4-((5-(pyridin-2-yl)thienyl-2-yl)ethynyl)benzamide

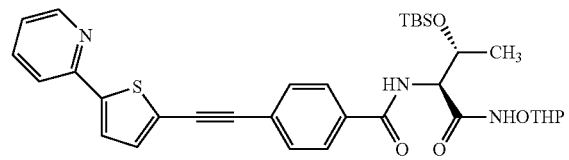

(2S,3R)-3-(tert-butyldimethylsilyloxy)-2-(4-((5-(pyridin-2-yl)thienyl-2-yl)ethynyl)benzamido)butanoic acid (660 mg, 1.27 mmol), O-(tetrahydro-2H-pyran-2-yl)hydroxylamine (223 mg, 1.90 mmol), 2-(7-azabenzotriazol-1-yl)-N,N,N',N'-tetramethyluronium hexafluorophosphate (867 mg, 2.28 mmol) and triethylamine (257 mg, 2.54 mmol) were dissolved in N,N-dimethylformamide (15 mL). The mixture was stirred at room temperature for 18 hours, diluted with ethyl acetate, and washed successively with water and saturated brine. The organic phase was dried over anhydrous sodium sulphate, and purified by silica column chromatography (petroleum ether:ethyl acetate=1:1) to give a white solid (354 mg) in a yield of 44.9%.

(6) Preparation of N-((2S,3R)-3-hydroxy-1-(hydroxyamino)-1-oxobutan-2-yl)-4-((5-(pyridin-2-yl)thienyl-2-yl)ethynyl)benzamide

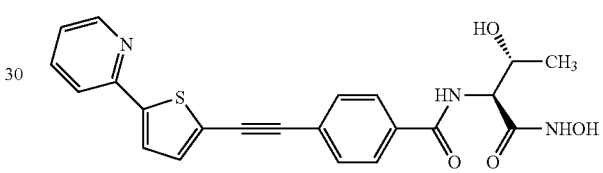

N-((2S,3R)-3-(tert-butyldimethylsilyloxy)-1-oxo-1-(tetrahydro-2H-pyran-2-yloxyamino)butan-2-yl)-4-((5-(pyridin-2-yl)thienyl-2-yl)ethynyl)benzamide (354 mg, 0.57 mmol) was dissolved in anhydrous ethanol (20 mL). A concentrated hydrochloric acid (5 mL) was slowly added dropwisely at room temperature. The mixture was reacted under stirring for 6 hours, concentrated under reduced pressure, and then purified by preparative liquid phase chromatography (methanol/water=20%) to give a white solid (180 mg) in a yield of 74.7%.

Molecular Formula: $C_{22}H_{19}N_3O_4S$; Molecular Weight: 421.1; Mass Spectrum (M+H): 422.1

$^1$H-NMR (d-DMSO, 400 MHz): δ 10.70 (1H, s), 8.87 (1H, s), 8.54 (1H, d), 8.17 (1H, d), 8.03-7.75 (5H, m), 7.67 (2H, d), 7.50 (1H, d), 7.33 (1H, m), 4.92 (1H, d), 4.25 (1H, dd), 4.02 (1H, q), 1.08 (3H, d).

With reference to the above preparation process, different intermediates D-allo-threonine methyl ester hydrochloride (2R,3R), L-allo-threonine methyl ester hydrochloride (2S,3S), D-threonine methyl ester hydrochloride (2R,3S) were used to prepare the final products having the corresponding configurations, and the racemic threonine methyl ester hydrochloride was used so that the racemic finish product could be prepared.

Example 39: Preparation of N-hydroxy-2-methyl-2-(methylsulfonyl)-4-(4-(4-((5-(morpholinomethyl)furan-2-yl)ethynyl)phenyl)-2-oxopyridin-1(2H)-yl)butanamide (Compound 45)
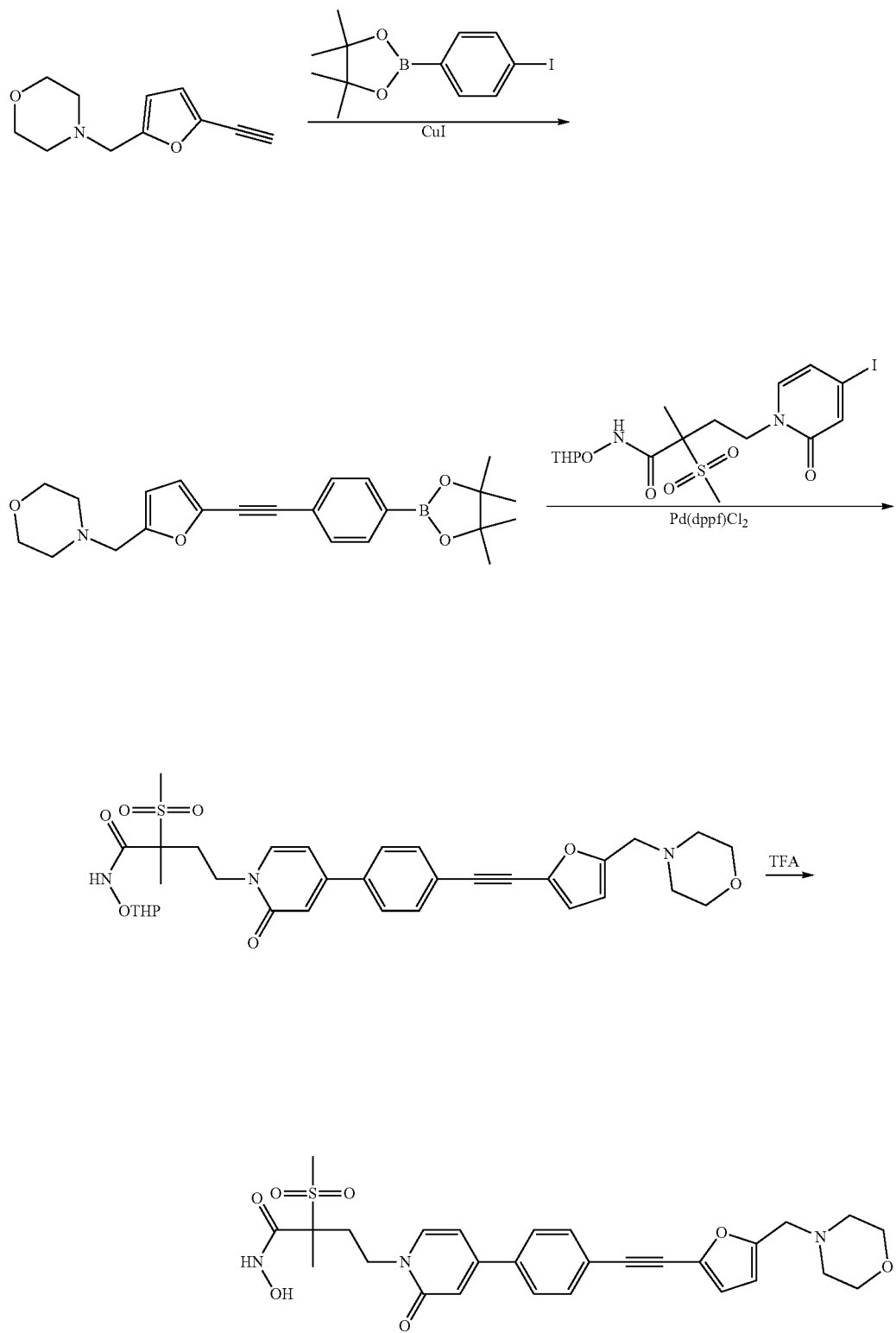

(1) Preparation of 4-((5-((4-(4,4,5,5-tetramethyl-1,3,2-dioxaborolan-2-yl)phenyl)ethynyl)furan-2-yl)methyl)morpholine

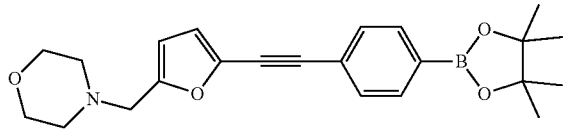 [SMILES: CC1(C)OB(c2ccc(C#Cc3ccc(CN4CCOCC4)o3)cc2)OC1(C)C]

4-((5-ethynylfuran-2-yl)methyl)morpholine(0.421 g, 2.20 mmol) was dissolved in acetonitrile (20 mL). Para-iodobenzeneboronic acid pinacol ester (0.800 g, 2.42 mmol), cuprous iodide (0.021 g, 0.11 mmol), triethylamine (0.511 g, 5.06 mmol), and Pd(Ph$_3$)$_2$Cl$_2$ (0.026 g, 0.037 mmol) were added. In the nitrogen protection, the mixture was reacted at 45° C. overnight. After the completion of the reaction, the reaction mixture was rotary-evaporated to dryness and purified by column chromatography (PE:EA=20:1→PE:EA=2:1) to give a brown solid (0.71 g) in a yield of 82.1%.

(2) Preparation of 2-methyl-2-(methylsulfonyl)-4-(4-(4-((5-(morpholinomethyl)furan-2-yl)ethynyl)phenyl)-2-oxopyridin-1(2H)-yl)-N-(tetrahydro-2H-pyran-2-yloxy)butanamide

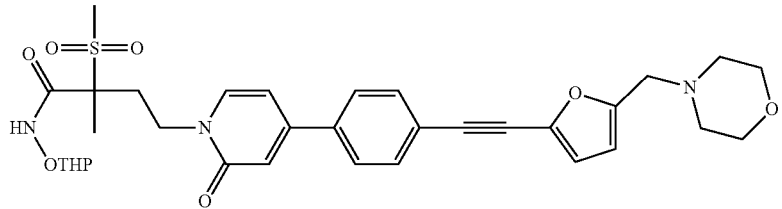

4-((5-((4-(4,4,5,5-tetramethyl-1,3,2-dioxaborolan-2-yl)phenyl)ethynyl)furan-2-yl)methyl)morpholine (0.359 g, 0.913 mmol) was dissolved in toluene (10 mL), ethanol (2 mL) and water (2 drops). Potassium phosphate (0.484 g, 2.283 mmol), and Pd(dppf)Cl$_2$ (0.056 g, 0.0761 mmol) were added. Then, 4-(4-iodo-2-oxopyridin-1(2H)-yl)-2-methyl-2-(methylsulfonyl)-N-(tetrahydro-2H-pyran-2-yloxy)butanamide (0.379 g, 0.761 mmol) was added. After the completion of the addition, the mixture was stirred at 80° C. in an oil bath overnight. The organic phase was concentrated under reduced pressure, and purified by column chromatography (PE:EA=10:1-EA) to give a yellow oily substance (0.15 g) in a yield of 30.9%.

(3) Preparation of N-hydroxy-2-methyl-2-(methylsulfonyl)-4-(4-(4-((5-(morpholinomethyl)furan-2-yl)ethynyl)phenyl)-2-oxopyridin-1(2H)-yl)butanamidae

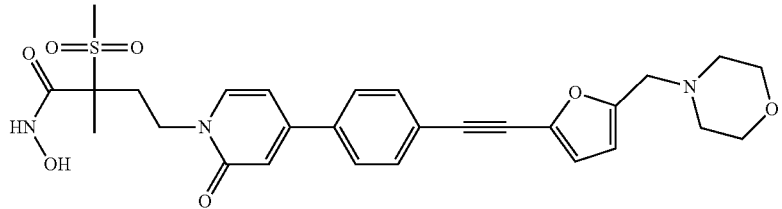 [SMILES: CC(CCn1ccc(-c2ccc(C#Cc3ccc(CN4CCOCC4)o3)cc2)cc1=O)(C(=O)NO)S(C)(=O)=O]

2-methyl-2-(methylsulfonyl)-4-(4-(4-((5-(morpholinomethyl)furan-2-yl)ethynyl)phenyl)-2-oxopyridin-1(2H)-yl)-N-(tetrahydro-2H-pyran-2-yloxy)butanamide (0.15 g, 0.235 mmol) was dissolved in dichloromethane (5 mL). Then trifluoroacetic acid (2 mL) was added. The mixture was stirred at room temperature for 1 hour, and a diluted ammonia water was added to adjust the pH value to about 3. The mixture was rotary-evaporated to dryness, and purified by preparative liquid phase chromatography (methanol:water=45:100) to give a white solid (78 mg) in a yield of 60.0%.

Molecular Formula: $C_{28}H_{31}N_3O_7S$; Molecular Weight: 553.2; Mass Spectrum (M+H): 554.2

$^1$H-NMR ($d_6$-DMSO, 400 MHz): δ 11.18 (1H, s), 9.30 (1H, s), 7.83-7.67 (3H, m), 7.66 (2H, d), 6.89 (1H, d), 6.76 (1H, s), 6.70 (1H, d), 6.46 (1H, d), 4.12 (1H, dt), 3.75 (1H, dt), 3.60-3.40 (10H, m), 3.11 (3H, s), 2.45-2.30 (1H, m), 2.20-2.05 (1H, m), 1.58 (3H, s)

Example 40: Preparation of N-hydroxy-4-{4-[4-(5-hydroxymethyl-furan-2-ethyl)-phenyl]-2-oxo-2H-pyridin-1-yl}-2-methylsulfonyl-2-methylbutylamine (Compound 46)

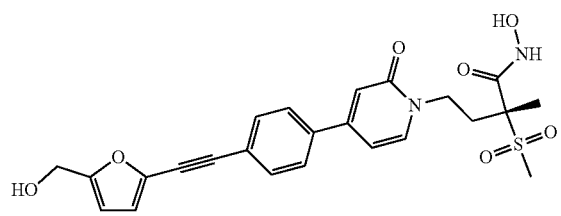 [SMILES: C[C@@](CCn1ccc(-c2ccc(C#Cc3ccc(CO)o3)cc2)cc1=O)(C(=O)NO)S(C)(=O)=O]

With reference to Example 39, Compound 46 was synthesized.

Molecular Formula: $C_{24}H_{24}N_2O_7S$; Molecular Weight: 484.1; Mass Spectrum (M+H): 485.2

$^1$H-NMR ($d_6$-DMSO, 400 MHz): $δ_{ppm}$ 11.2 (brs, 1H), 7.78 (m, 3H), 7.63 (d, 2H), 6.87 (d, 1H), 6.75 (s, 1H), 6.68 (t, 1H), 6.42 (s, 1H), 4.41 (s, 2H), 4.1 (m, 1H), 3.76 (m, 2H), 3.10 (s, 3H), 2.39-2.49 (m, 1H), 2.14-2.20 (m, 1H), 1.57 (m, 3H).

Example 41: Preparation of N-hydroxy-4-(4-{4-[4-(5-hydroxymethyl-furan-2-yl)-buta-1,3-diynyl]-phenyl}-2-oxo-2H-pyridin-1-yl)-2-methylsulfonyl-2-methylbutylamine (Compound 47)

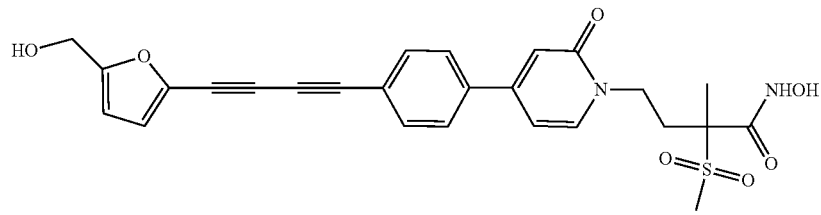

With reference to Example 39, Compound 47 was synthesized.

Molecular Formula: $C_{26}H_{24}N_2O_7S$; Molecular Weight: 508.13; Mass Spectrum (M+H): 509.1

$^1$H-NMR ($d_6$-DMSO, 400 MHz): $δ_{ppm}$ 11.15 (1H, s), 7.83-7.79 (3H, m), 7.73 (2H, d), 7.07 (1H, d), 6.77 (1H, d), 6.69 (1H, dd), 6.45 (1H, d), 4.42 (2H, s), 4.14-4.09 (1H, m), 3.7.8-3.74 (1H, m), 3.11 (3H, s), 2.46-2.41 (1H, m), 2.19-2.15 (1H, m), 1.57 (3H, s).

Example 42: Preparation of N-1-hydroxy-2-methylsulfonyl-4-[4-[4-(5-methoxymethylfuran-2-ethyl)phenyl]-2-oxo-2H-pyridin-1-yl}-2-methylbutanediamine (Compound 48)

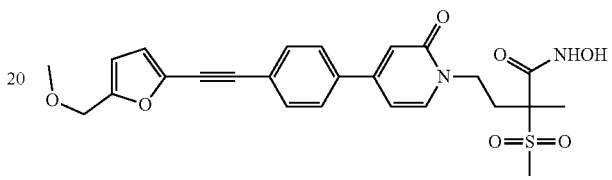

With reference to Example 39, Compound 48 was synthesized.

Molecular Formula: $C_{25}H_{26}N_2O_7S$; Molecular Weight: 498.1; Mass Spectrum (M+H): 499.5

INDUSTRIAL UTILITY

The present invention provides an antibacterial, which shows excellent antibacterial activity against bacteria, particularly against Gram bacteria, as the LpxC inhibitor.

Moreover, the compounds of the present invention are excellent in metabolism stability in vivo.

The invention claimed is:
1. A compound represented by the general formula (I), a pharmaceutically acceptable salt thereof, an ester thereof, a prodrug thereof, a solvate thereof, or a deuterated analog thereof, or a stereoisomer thereof:

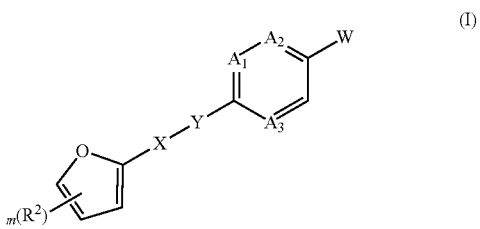

wherein,
W represents

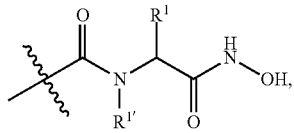

R$^1$ is selected from a group consisting of —(CH$_2$)$_{0-4}$C(R$^{1a}$, R$^{1b}$)(CH$_2$)$_{0-4}$OR$^3$, and —(CH$_2$)$_{0-4}$C(R$^{1a}$,R$^{1b}$)(CH$_2$)$_{0-4}$S(O)$_{0-2}$R$^6$, wherein, R$^{1a}$, R$^{1b}$, R$^3$, and R$^6$ are each independently selected from a group consisting of H, C$_{1-6}$ alkyl and OH;

R$^{1'}$ is selected from a group consisting of hydrogen and C$_{1-6}$alkyl;

A$_1$, A$_2$, and A$_3$ are each independently selected from a group consisting of CH and N;

X and Y are each independently selected from a group consisting of a benzene ring group, an alkenyl group, an alkynyl group and

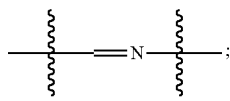 [SMILES: *C=N*]

R$^2$ is

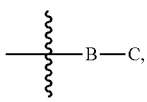

B represents —(C$_{1-8}$alkyl)-, wherein 0-2 carbon atoms in said —(C$_{1-8}$alkyl)- are replaced with —O— or —NR$^8$—, C is selected from a group consisting of —OR$^9$, —NR$^9$R$^{9'}$, and

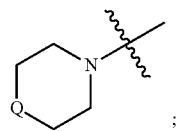

Q is a group selected from a group consisting of NR$^c$ and O;

R$^8$, R$^9$ and R$^{9'}$ are each independently selected from hydrogen atom, and C$_{1-6}$alkyl; and m is 1, 2 or 3.

2. The compound according to claim 1, a pharmaceutically acceptable salt thereof, an ester thereof, a prodrug thereof, a solvate thereof, or a deuterated analog thereof, or a stereoisomer thereof:

wherein,
W represents

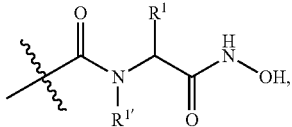

R$^1$ is —C(R$^{1a}$,R$^{1b}$)OR$^3$, wherein, R$^{1a}$, R$^{1b}$ and R$^3$ are each independently selected from a group consisting of hydrogen atom, methyl and hydroxyl;

R$^{1'}$ is selected from a group consisting of hydrogen and C$_{1-4}$alkyl;

A$_1$, A$_2$, and A$_3$ are each independently selected from a group consisting of CH and N;

X and Y are each independently selected from a group consisting of a benzene ring group, an alkenyl group, an alkynyl group and

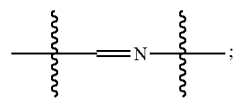 [SMILES: *C=N*]

R$^2$ is

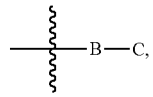

B represents —(C$_{1-4}$alkyl)-,

C is selected from a group consisting of —OR$^9$ and —NR$^9$R$^{9'}$,

R$^9$ and R$^{9'}$ are each independently selected from hydrogen atom, methyl, ethyl, isopropyl; and m is 1 or 2.

3. The compound according to claim 1, a pharmaceutically acceptable salt thereof, an ester thereof, a prodrug thereof, a solvate thereof, or a deuterated analog thereof, or a stereoisomer thereof:

wherein,
W represents

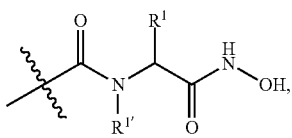

R$^1$ is —C(H,CH$_3$)OH;

R$^{1'}$ is selected from a group consisting of H, methyl, and ethyl;

A$_1$, A$_2$, and A$_3$ are each independently selected from a group consisting of CH and N;

X and Y are each independently selected from a group consisting of a benzene ring group, an alkenyl group, an alkynyl group, and

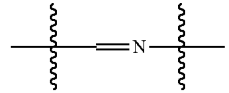 [SMILES: *C=N*]

$R^2$ is —CH$_2$OH; and m is 1.

4. A compound represented by the general formula (III), a pharmaceutically acceptable salt thereof, an ester thereof, a prodrug thereof, a solvate thereof, or a deuterated analog thereof, or a stereoisomer thereof:

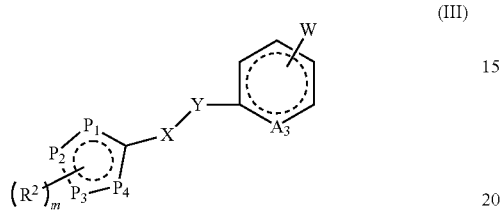

(III)

wherein,

W represents —(C$_{0-8}$alkyl)-C(O)—N(R$^{1'}$)—(C$_{1-8}$alkyl optionally substituted by R$^1$)—C(O)—N(H)—OH;

R$^1$ is each independently selected from a group consisting of C$_{1-8}$alkyl optionally substituted by OH and —(C$_{0-8}$alkyl)S(O)$_{1-2}$R$^3$, wherein, R$^3$ is selected from a group consisting of hydrogen atom and C$_{1-8}$alkyl optionally substituted by a substituent group;

R$^{1'}$ is selected from a group consisting of hydrogen atom, hydroxyl, methyl, ethyl, propyl, isopropyl, butyl, sec-butyl and tert-butyl, or R$^{1'}$ and the carbon atom in the C$_{0-8}$alkyl in the group W, together with the groups N and C(O), form a 6-membered unsaturated heterocyclic group;

A$_3$ is selected from a group consisting of CR$^a$R$^a$ and NR$^c$;

X and Y are each independently selected from a group consisting of a benzene ring group optionally substituted by a substituent group, —(C=C)—, —(C≡C)—, =N—, and —C(O)—NR$^c$—, wherein X and Y are not simultaneously each a benzene ring group optionally substituted by a substituent group;

the five-membered ring moiety containing P$_1$, P$_2$, P$_3$, and P$_4$ as shown in general formula (III) is selected from a group consisting of a furan group, a pyrrole group, a pyrazole group, a triazole group and a thiophene group;

m represents 1, 2 or 3;

in each occurrence, R$^2$ each independently represents

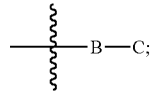

in each occurrence, B independently represents a bond, or is each independently selected from a group consisting of C$_{1-8}$alkyl optionally in which at least one carbon atom is replaced with at least one group of O and NR$^c$;

in each occurrence, C independently represents —OR$^c$, —NR$^c$R$^c$, or

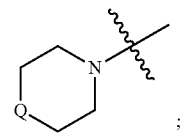

Q is a group selected from a group consisting of NR$^c$ and O;

R$^a$ either is absent or in each occurrence are each independently selected from a group consisting of hydrogen atom and;

R$^c$ either is absent or in each occurrence are each independently selected from a group consisting of hydrogen atom and said substituent group in "optionally substituted by a substituent group" is each independently selected from a group consisting of hydroxyl and

in the five-membered ring and the six-membered ring represents a double bond optionally present in the ring;

provided that:

when R$^1$ represents the C$_{1-8}$alkyl substituted by a substituent, and the substituent contains hydroxyl, each carbon atom of the C$_{1-8}$alkyl carries at least one hydrogen;

when R$^1$ represents the C$_{1-8}$alkyl substituted by a substituent, and the substituent contains amino, C$_{1-8}$alkylamino or (C$_{1-8}$ alkyl)$_2$amino, at least one of X and Y represents a benzene ring group optionally substituted by a substituent group; and when the five-membered ring contains one nitrogen atom, the five-membered ring is bonded to X through a non-nitrogen atom.

5. The compound according to claim 4, a pharmaceutically acceptable salt thereof, an ester thereof, a prodrug thereof, a solvate thereof, or a deuterated analog thereof, or a stereoisomer thereof, which compound is a compound represented by the following general formula (IV):

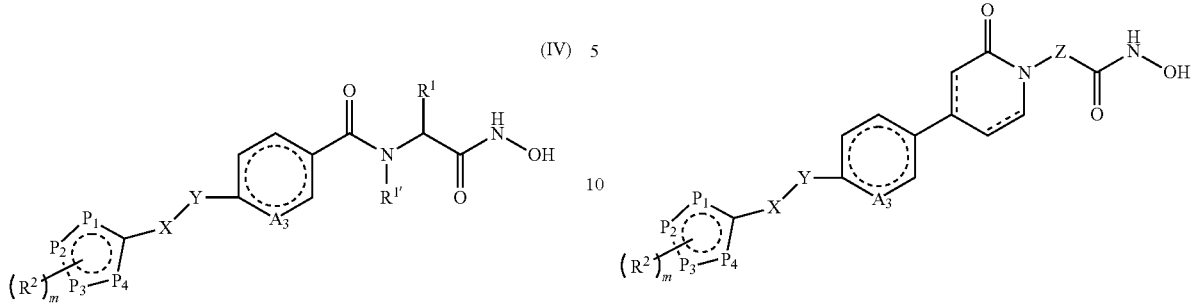

wherein each group is defined as in claim 4.

6. The compound according to claim 4, a pharmaceutically acceptable salt thereof, an ester thereof, a prodrug thereof, a solvate thereof, or a deuterated analog thereof, or a stereoisomer thereof, which compound is a compound represented by the following general formula (V):

wherein each group is defined as in claim 4, Z represents $C_{1-8}$alkyl optionally substituted by $R^1$, represents a double bond.

7. A compound, a pharmaceutically acceptable salt thereof, an ester thereof, a prodrug thereof, a solvate thereof, or a deuterated analog thereof, or a stereoisomer thereof, which compound is selected from a group consisting of the following compounds:

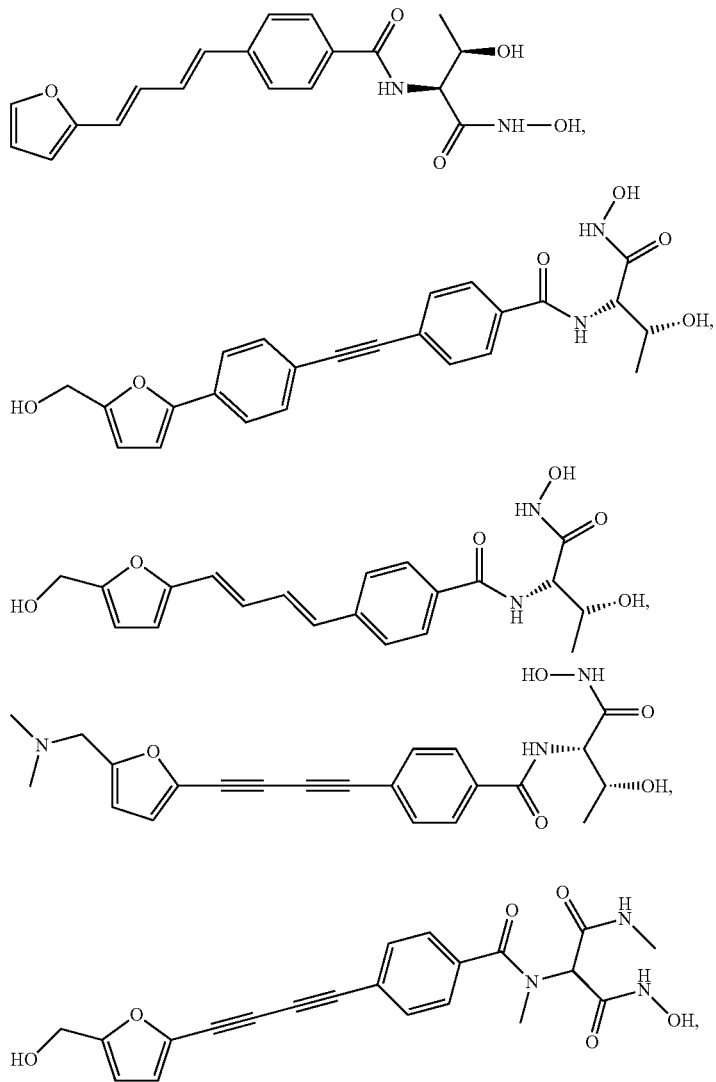

-continued
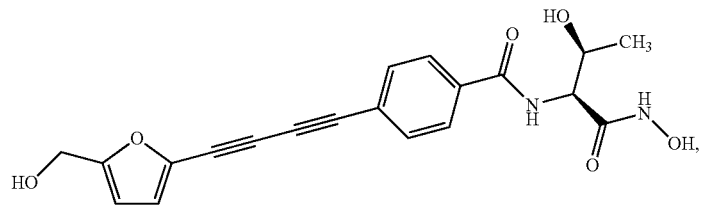
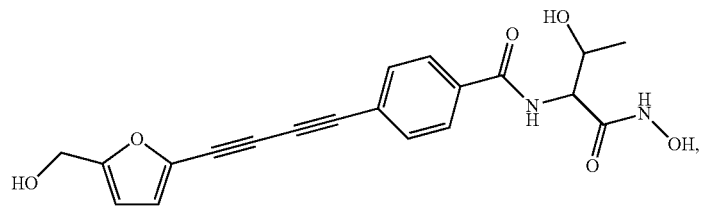
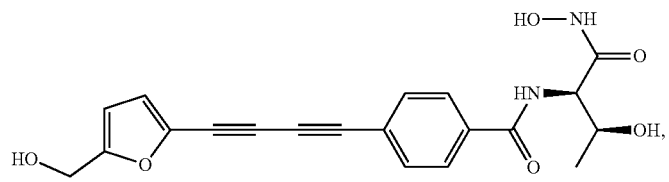
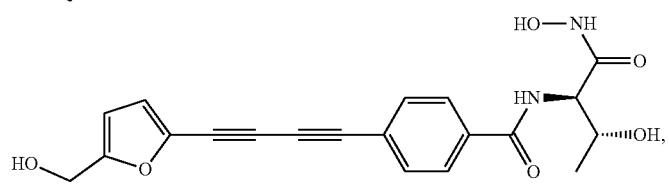
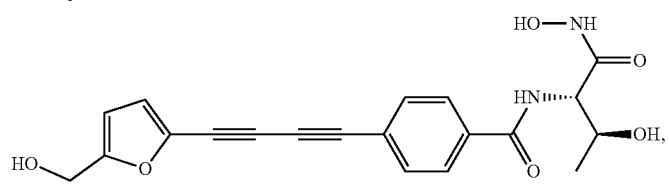
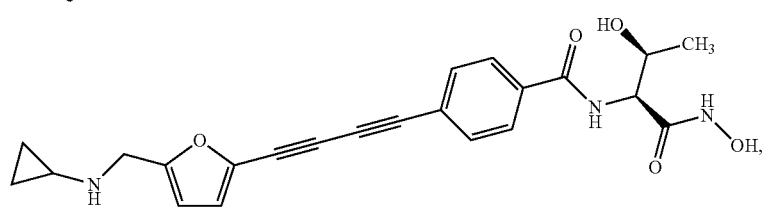
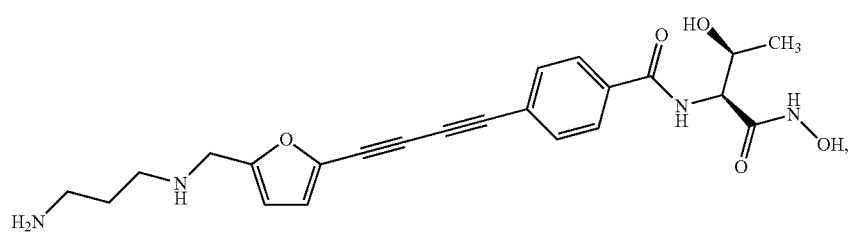
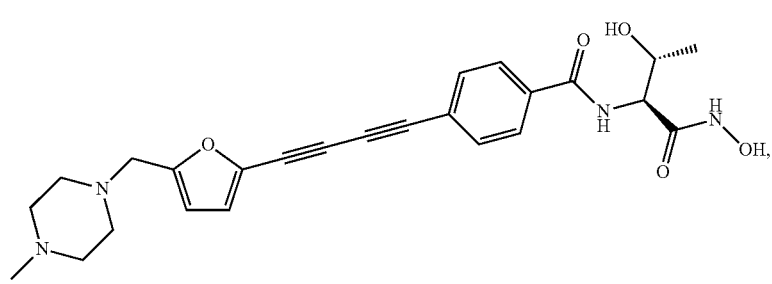

-continued
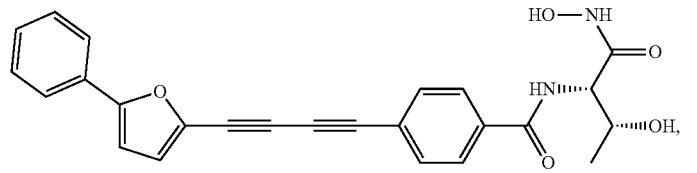
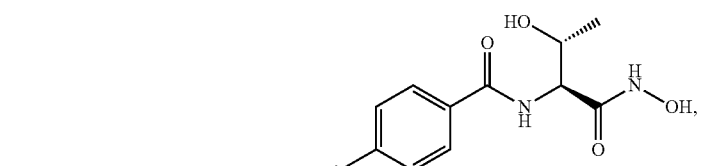
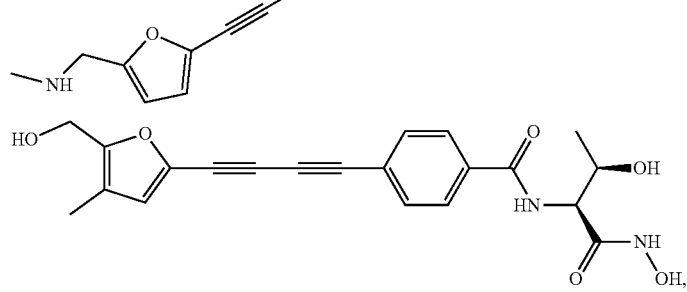
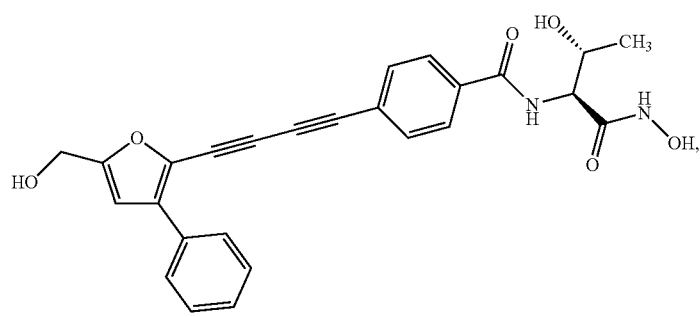
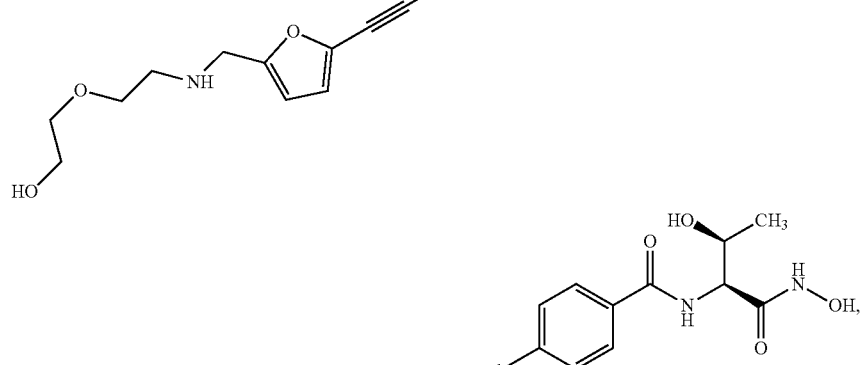

-continued
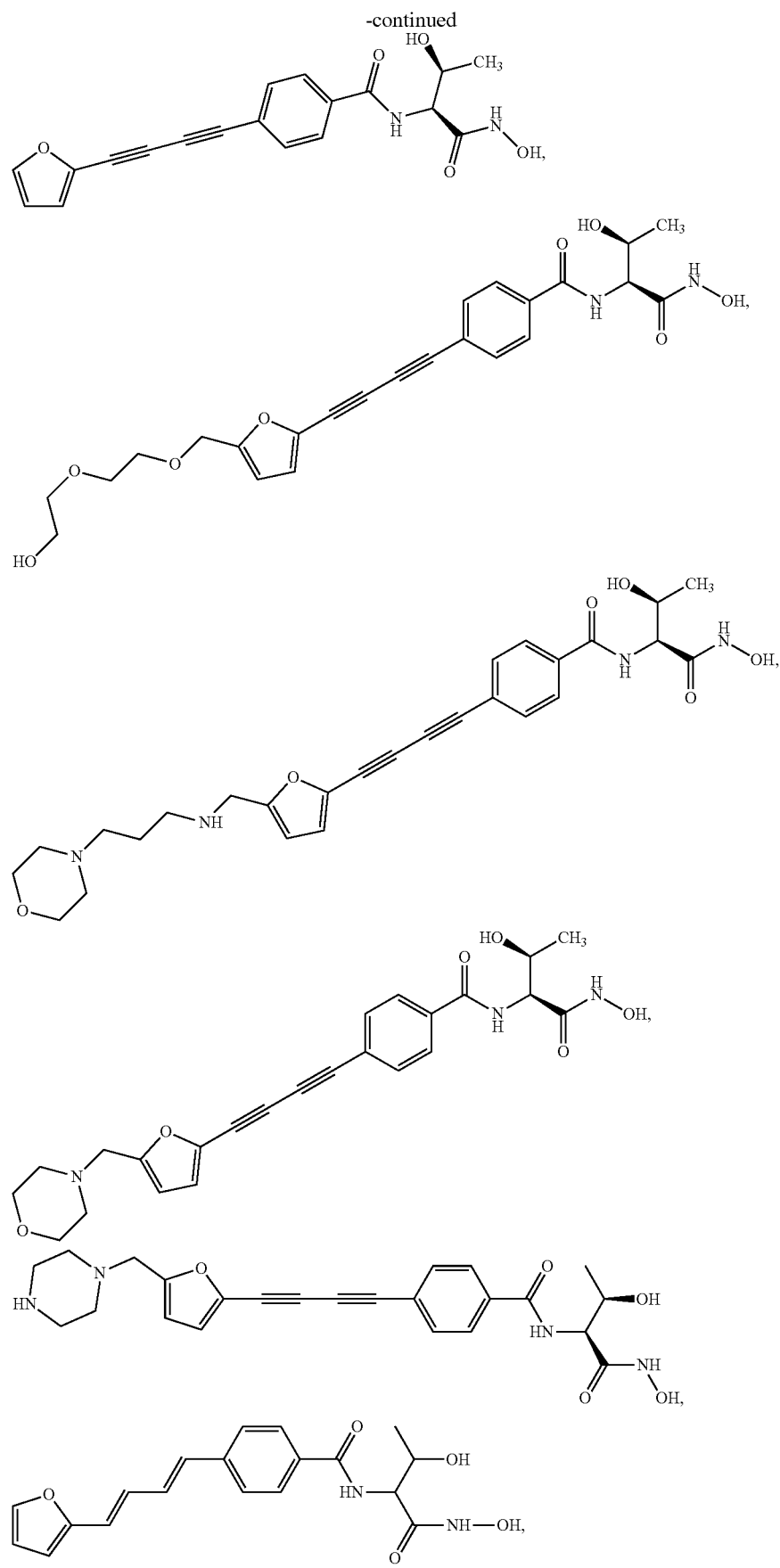

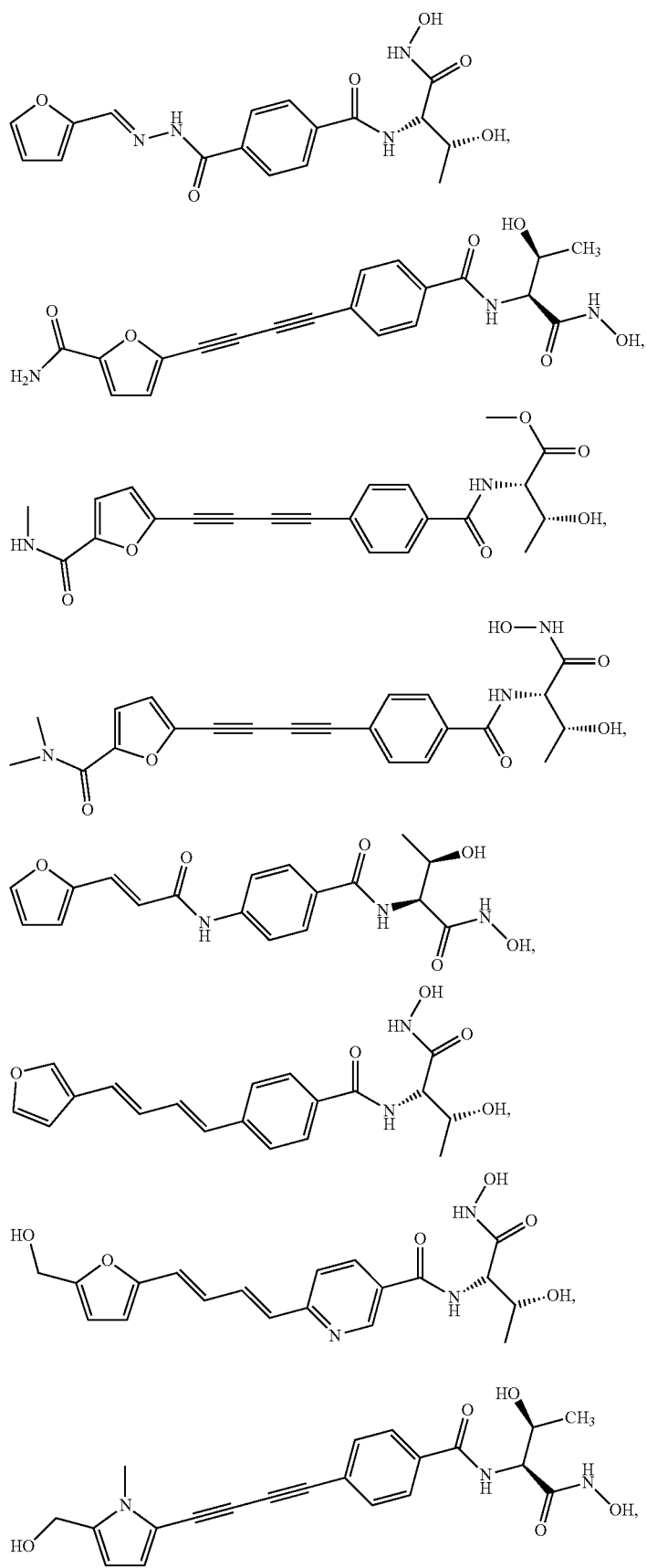

-continued
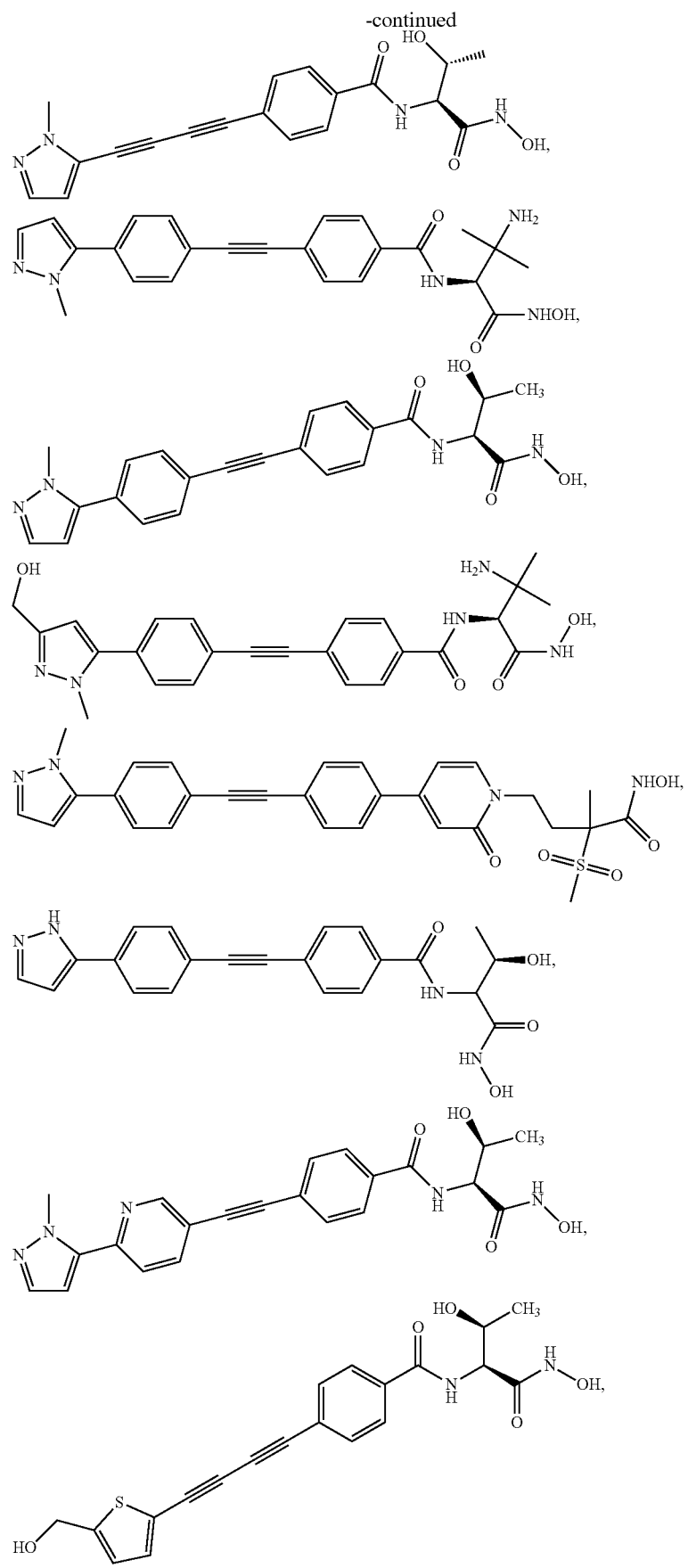

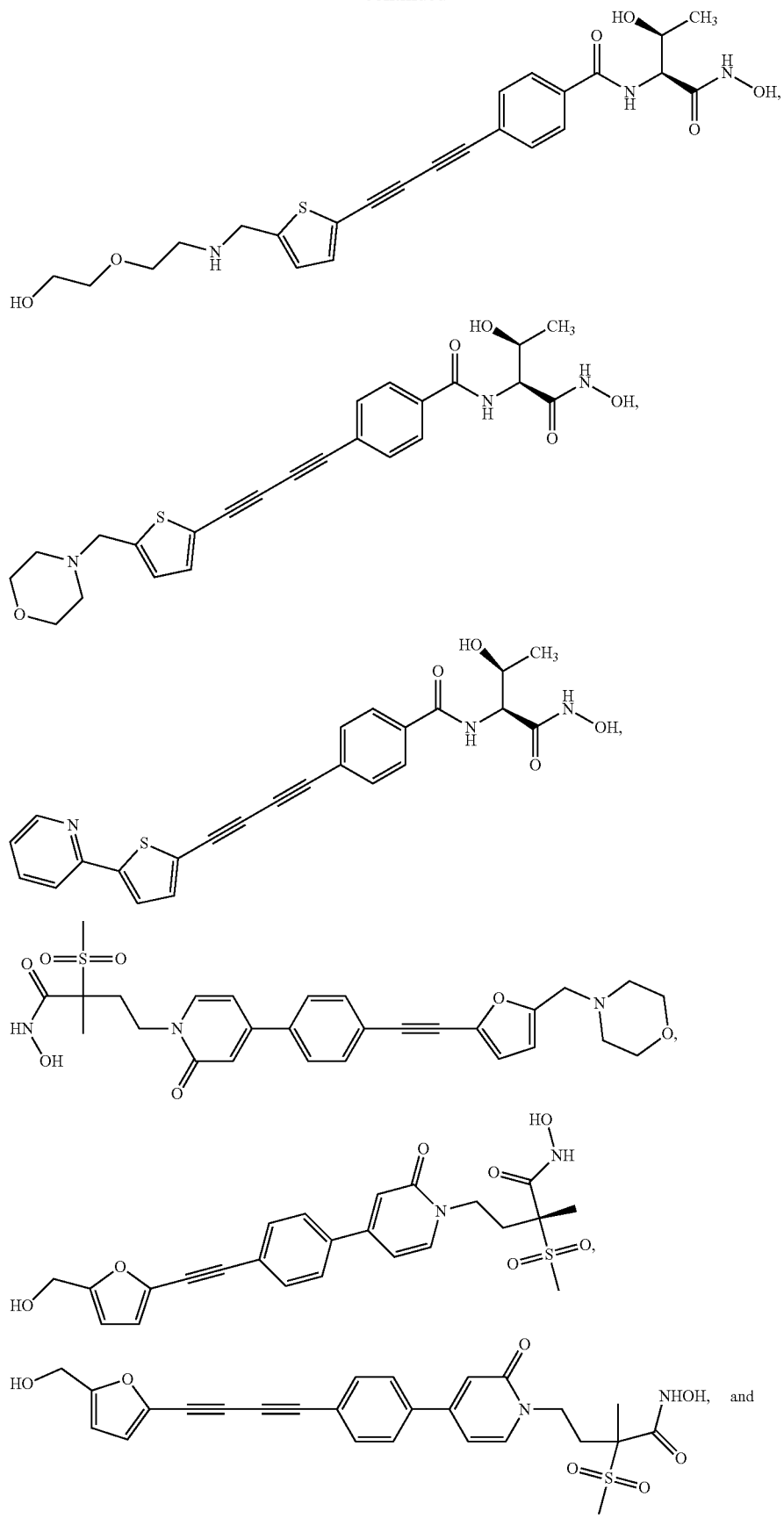

-continued

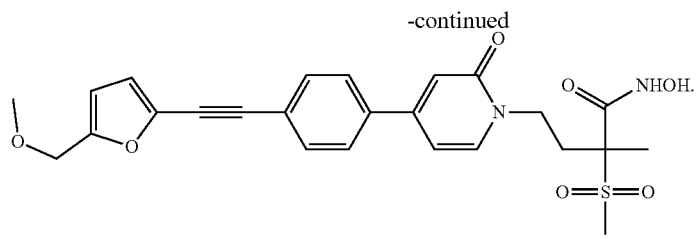

8. A pharmaceutical composition, comprising the compound according to claim 1, a pharmaceutically acceptable salt thereof, an ester thereof, a prodrug thereof, a solvate thereof, or a deuterated analog thereof, or a stereoisomer thereof.

9. A method of treating infectious diseases caused by Gram-negative bacteria, comprising administering to the subject the compound according to claim 1, or a pharmaceutically acceptable salt thereof, an ester thereof, a prodrug thereof, a solvate thereof, or a deuterated analog thereof, or a stereoisomer thereof, or a pharmaceutical composition comprising the compound according to claim 1.

10. A pharmaceutical composition, comprising the compound according to claim 4, a pharmaceutically acceptable salt thereof, an ester thereof, a prodrug thereof, a solvate thereof, or a deuterated analog thereof, or a stereoisomer thereof.

11. A method of treating infectious diseases caused by Gram-negative bacteria, comprising administering to the subject the compound according to claim 4, or a pharmaceutically acceptable salt thereof, an ester thereof, a prodrug thereof, a solvate thereof, or a deuterated analog thereof, or a stereoisomer thereof, or a pharmaceutical composition comprising the compound according to claim 4.

12. A pharmaceutical composition, comprising the compound according to claim 7, a pharmaceutically acceptable salt thereof, an ester thereof, a prodrug thereof, a solvate thereof, or a deuterated analog thereof, or a stereoisomer thereof.

13. A method of treating infectious diseases caused by Gram-negative bacteria, comprising administering to the subject the compound according to claim 7, or a pharmaceutically acceptable salt thereof, an ester thereof, a prodrug thereof, a solvate thereof, or a deuterated analog thereof, or a stereoisomer thereof, or a pharmaceutical composition comprising the compound according to claim 7.

* * * * *

UNITED STATES PATENT AND TRADEMARK OFFICE
CERTIFICATE OF CORRECTION

PATENT NO. : 11,498,909 B2
APPLICATION NO. : 16/968390
DATED : November 15, 2022
INVENTOR(S) : Zhenhua Huang et al.

It is certified that error appears in the above-identified patent and that said Letters Patent is hereby corrected as shown below:

In the Claims

At Column 142, Claim number 4, Line number 33, please add "$C_{1-8}$ alkyl;" after "and".

At Column 144, Claim number 6, Line number 17, please add "═" after "$R^1$,".

Signed and Sealed this
Twenty-first Day of February, 2023

Katherine Kelly Vidal
*Director of the United States Patent and Trademark Office*